US007825667B2

(12) United States Patent
Fang et al.

(10) Patent No.: US 7,825,667 B2
(45) Date of Patent: Nov. 2, 2010

(54) MICROWAVE IMAGING SYSTEM AND PROCESSES, AND ASSOCIATED SOFTWARE PRODUCTS

(75) Inventors: Qianqian Fang, Somerville, MA (US); Paul M. Meaney, Hanover, NH (US); Keith D. Paulsen, Hanover, NH (US)

(73) Assignee: Microwave Imaging Systems Technologies, Inc., Hanover, NH (US)

( * ) Notice: Subject to any disclaimer, the term of this patent is extended or adjusted under 35 U.S.C. 154(b) by 1337 days.

(21) Appl. No.: 11/316,641

(22) Filed: Dec. 21, 2005

(65) Prior Publication Data

US 2006/0241410 A1   Oct. 26, 2006

Related U.S. Application Data

(63) Continuation-in-part of application No. 10/407,886, filed on Apr. 4, 2003, now abandoned.

(60) Provisional application No. 60/638,005, filed on Dec. 21, 2004.

(51) Int. Cl.
*G01N 23/02* (2006.01)
*A61B 5/05* (2006.01)

(52) U.S. Cl. ........................ 324/637; 324/638; 600/430; 378/8

(58) Field of Classification Search .................. 324/638, 324/637; 600/430; 378/8
See application file for complete search history.

(56) References Cited

U.S. PATENT DOCUMENTS 5,715,819 A * 2/1998 Svenson et al. ............. 600/425
5,841,288 A * 11/1998 Meaney et al. ............... 324/639
6,005,916 A * 12/1999 Johnson et al. ................ 378/87
6,421,550 B1 * 7/2002 Bridges et al. ............... 600/407
2004/0077943 A1   4/2004 Meaney et al.
2004/0167399 A1   8/2004 Li
2004/0234113 A1 * 11/2004 Miga .......................... 382/128

FOREIGN PATENT DOCUMENTS

WO   WO 2004/052169 A2   6/2004

* cited by examiner

*Primary Examiner*—Timothy J Dole
*Assistant Examiner*—John Zhu
(74) *Attorney, Agent, or Firm*—Lathrop & Gage LLP

(57) ABSTRACT

A microwave imaging process, and a system controlled by an associated software product, illuminate a target with microwaves from a transmitting antenna. Receiving antennas receive microwaves scattered by the target, and form microwave data. The illumination and receiving repeat over multiple transmitting antennas and multiple microwave frequencies. The microwave data is processed to form permittivity and conductivity images by selecting a background dispersion model for permittivity and conductivity. Permittivity and conductivity dispersion coefficients are determined, and permittivity and conductivity distributions are calculated, for each of the microwave frequencies. Forward solutions at multiple frequencies are determined from property distributions, and a dispersion coefficient based Jacobian matrix is determined. Dispersion coefficient updates are determined using the microwave data, and the dispersion coefficients are updated. Permittivity and conductivity distributions are recalculated for each of the frequencies, and the forward solutions are determined at multiple frequencies from property distributions.

40 Claims, 24 Drawing Sheets

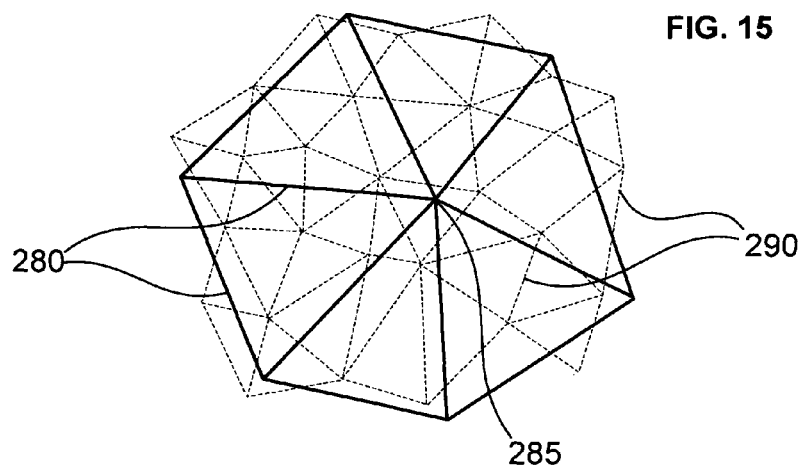
FIG. 15
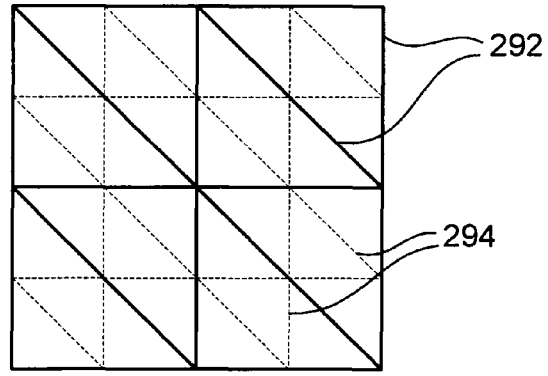
FIG. 16
FIG. 17

MICROWAVE IMAGING SYSTEM AND PROCESSES, AND ASSOCIATED SOFTWARE PRODUCTS

CROSS-REFERENCE TO RELATED APPLICATIONS

This application claims priority to U.S. Provisional Patent Application No. 60/638,005 filed 21 Dec. 2004. This application is also a continuation-in-part of U.S. patent application Ser. No. 10/407,886 filed 4 Apr. 2003 now abandoned. Both of the above-identified patent applications are incorporated herein by reference. U.S. Pat. Nos. 5,841,288 and 6,448,788 are also incorporated herein by reference.

U.S. GOVERNMENT RIGHTS

This invention was made with Government support under NIH Grant No. CA80139 awarded by the National Institutes of Health. The Government has certain rights in this invention.

BACKGROUND

Microwave imaging technology has seen rapid advances in the last few years. However, gathering and analyzing data for microwave imaging may take significant time, making three-dimensional image reconstruction difficult.

SUMMARY

In one embodiment, a microwave imaging process illuminates a target with microwaves from a transmitting antenna. Receiving antennas receive microwaves scattered by the target, and form microwave data. The illumination and receiving repeat over multiple transmitting antennas and multiple microwave frequencies. The microwave data is processed to form permittivity and conductivity images by selecting a background dispersion model for permittivity and conductivity. Permittivity and conductivity dispersion coefficients are determined, and permittivity and conductivity distributions are calculated, for each of the microwave frequencies. Forward solutions at multiple frequencies are determined from property distributions, and a dispersion coefficient based Jacobian matrix is determined. Dispersion coefficient updates are determined using the microwave data, and the dispersion coefficients are updated. Permittivity and conductivity distributions are recalculated for each of the frequencies, and the forward solutions are determined at multiple frequencies from property distributions.

In one embodiment, a microwave imaging process generates microwave data and estimates initial $\epsilon_r$ and $\sigma$ distributions to form current $\epsilon_r$ and $\sigma$ distributions. A forward solution is determined based on the current $\epsilon_r$ and $\sigma$ distributions, utilizing a finite difference time domain method. Computed field values are extracted, and a tolerance metric is determined. If the tolerance metric does not meet a preselected limit, a Jacobian matrix is calculated, $\epsilon_r$ and $\sigma$ distributions are recalculated to form current $\epsilon_r$ and $\sigma$ distributions, and iterating until the tolerance metric meets the preselected limit.

In one embodiment, a microwave imaging process reconstructs a permittivity and conductivity image utilizing microwave data of a target. Forward solutions are determined from property distributions, utilizing forward field solutions from one iteration as a starting point for a subsequent iteration. A Jacobian matrix is determined and dispersion coefficient updates are determined using the microwave data. The determination of forward solutions, determination of a Jacobian matrix, and determination of dispersion coefficient updates iterate until the image converges.

In one embodiment, a microwave imaging system has a microwave frequency signal source and at least one transmitting antenna that illuminates a target within an illumination tank with microwaves. Receiving antennas receive microwaves scattered by the target, and form microwave data. A signal processor processes the microwave data into images of the target.

In one embodiment, a software product includes instructions that, when executed by a processor, generate an image of a target using microwaves, including: instructions for controlling illumination of the target with microwaves sequentially from one or more transmitting antennas and over one or more frequencies; instructions for storing microwave data from microwaves scattered by the target and received at a plurality of receiving antennas; instructions for selecting a background dispersion model for permittivity and conductivity; instructions for determining dispersion coefficients for the background dispersion model; instructions for determining permittivity and conductivity distributions for each frequency; instructions for determining forward solutions at multiple frequencies from property distributions; instructions for determining a dispersion coefficient based Jacobian matrix and instructions for determining dispersion coefficient updates using the microwave data; instructions for updating the dispersion coefficients; instructions for determining permittivity and conductivity distributions for each of the frequencies; and instructions for determining the forward solutions at multiple frequencies from property distributions.

In one embodiment, a software product includes instructions that, when executed by a processor, reconstructing images of a target, including: instructions for generating microwave data; instructions for estimating initial $\epsilon_r$ and $\sigma$ distributions to form current $\epsilon_r$ and $\sigma$ distributions; instructions for determining a forward solution that is based on the current $\epsilon_r$ and $\sigma$ distributions and utilizes a finite difference time domain method; instructions for extracting computed field values; instructions for determining a tolerance metric, instructions for calculating a Jacobian matrix; instructions for recalculating $\epsilon_r$ and $\sigma$ distributions to form current $\epsilon_r$ and $\sigma$ distributions; and instructions for repeating the steps of determining a forward solution, extracting, determining a tolerance metric, calculating a Jacobian matrix, and recalculating until the tolerance metric meets the preselected limit.

BRIEF DESCRIPTION OF DRAWINGS

FIG. 15 illustrates a case in which boundaries of forward elements do not precisely match those of parameter elements.

FIG. 16 shows plots of a segment of an original parameter mesh superimposed on a refined forward mesh.

FIG. 17 shows a plot of maximum relative error between a nodal adjoint calculation and an adjoint calculation of the Jacobian matrix.

DETAILED DESCRIPTION OF DRAWINGS

Certain microwave imaging systems illuminate a target to be imaged by radiating microwaves in the vicinity of the target, capturing microwaves that have interacted with the target, and reconstructing images based on internal, point-to-point variations of electrical properties of the target. Reconstruction techniques generally create a matrix of data points that models phenomena at points of a "mesh." A typical reconstruction may include modeling, at each point of the mesh: (1) electrical field distributions (as transmitted by one or more microwave source antennas, and as scattered by the target and by a "coupling medium" through which the microwaves pass to and from the target); and (2) electrical permittivity and conductivity distributions (e.g., properties of the target and the coupling medium). In certain cases, one mesh (a "forward mesh") is used to calculate electrical fields (this calculation is designated the "forward problem") and a different mesh (a "parametric mesh"), encompassing at least part of the area or volume of the forward mesh, is used to calculate parameter distributions. The parametric mesh may only encompass an area or volume of the target being imaged, while the forward mesh may encompass the area or volume of the parametric mesh plus a surrounding area or volume in order to account for propagation of electromagnetic fields about transmitting and receiving antennas. The modeling calculations may start with no a priori information about the target and/or the coupling medium, and may iterate until they converge on a solution that is consistent with microwave signals captured by one or more receiving antennas.

Three-dimensional ("3D") calculations involve building three-dimensional forward and parametric meshes that encompass a volume, each having many more elements than corresponding two-dimensional ("2D") meshes that encompass an area. Additionally, data associated with each element in a 3D calculation may be more complex than an element in a corresponding 2D calculation (e.g., an electric field value of each element may be represented by a 3D vector instead of a 2D vector or scalar). Furthermore, certain microwave imaging systems utilize a single frequency. The frequency is generally chosen to be as high as possible, to achieve the best possible image resolution, since resolution is related to wavelength (higher frequency corresponding to shorter wavelength). However, in some cases the image reconstruction algorithm diverges. This can be caused, for example, by high contrast between dielectric properties of the imaging target and the background, which can lead to large phase projections and/or complex nulls that make the phase distribution nonunique and, consequently, unusable for imaging.

Figure 1:
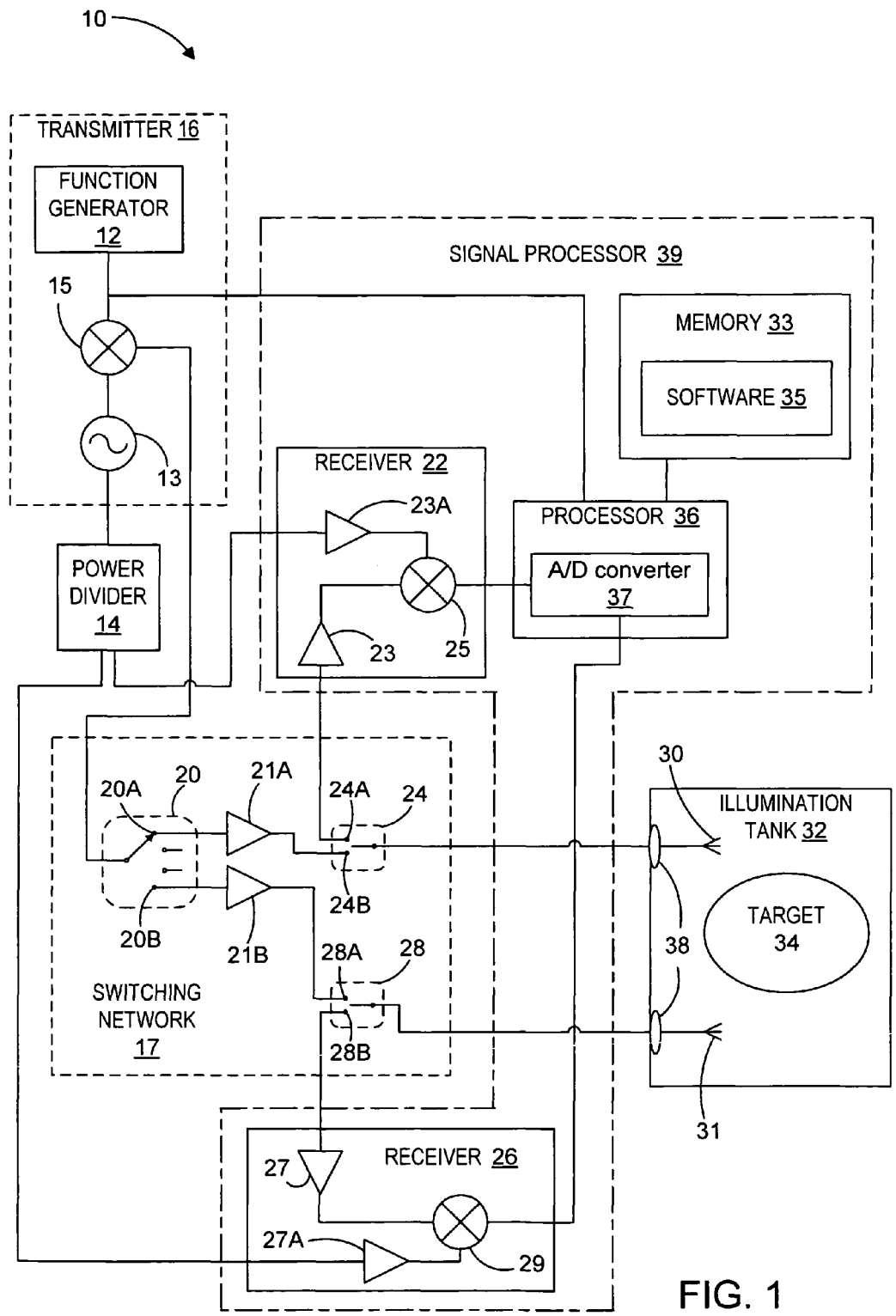
FIG. 1 shows a block diagram of a microwave imaging system, in accord with one embodiment.

FIG. 1 shows a block diagram of a microwave imaging system 10. System 10 is configured for examining a target 34 in an illumination tank 32. Target 34 may include biological tissue; in one embodiment, system 10 is particularly useful in determining whether target 34 contains sections of abnormal tissue, such as malignant or cancerous tissue.

System 10 includes receivers 22 and 26. Receivers 22, 26 represent a plurality of receivers configured for receiving RF signals from antennas 30 and 31, respectively; these RF signals may be microwave signals that may be in a frequency range of 3 MHz to 30 GHz; a range of 300 MHz to 3 GHz may be a preferred range. Antennas 30, 31 are examples of antennas that may number more than two to form an array of antennas (see FIG. 2-FIG. 4), may be coupled through seals 38 (e.g., hydraulic seals, see FIG. 6) in illumination tank 32 and may transmit and receive microwave signals. Each of antennas 30 and 31 has a respectively coupled receiver (e.g., receivers 22 and 26) configured for receiving and for demodulating the signals. Demodulated signals produced by receivers (e.g., produced by receivers 22 and 26) may be IF (intermediate frequency) signals ranging in frequency from 1 KHz to 20 MHz, but may include other frequencies as a matter of design choice.

System 10 also has a signal processor 39 that includes processor 36 memory 33 for storing data and for storing software 35 and one or more receivers (e.g., receivers 22, 26). Processor 36 may load and execute software 35 and thereby control all functions of system 10. Processor 36 also couples with, and processes a digital representation of the demodulated signals from, receivers 22, 26.

In one embodiment, processor 36 includes an analog to digital ("A/D") converter 37 which digitizes the demodulated signals from each of the receivers. In one embodiment, A/D converter 37 is a single integrated circuit or circuit board with a plurality of A/D samplers, each sampler being dedicated to a signal from one receiver. Alternatively, processor 36 may multiplex signals from a plurality of receivers, feeding the result to a single channel A/D converter 37 which samples the signals sequentially. Processor 36 then processes the digitized signals to determine phase differences between digital representations of a modulating waveform of the transmitted signal and the demodulated signals. As used herein, the transmitted signal includes a carrier signal modulated by a modulating signal.

To illustrate, if two receivers receive signals from their respectively coupled antennas, then each of the two receivers demodulates a received signal from their respective antenna to extract a demodulated signal. A/D converter 37 digitizes each of the two demodulated signals and processor 36 processes those two demodulated signals by comparing each demodulated signal to a digital representation of the modulating waveform of the transmitted signal.

In signal processor 39 processor 36 (executing software 35 in memory 33) may examine phase differences between a particular received demodulated signal and the modulating waveform of the transmitted signal, producing scattered magnitude and phase signal projections due to the presence of target 34. The projections may be used to reconstruct electrical property images for use in identifying tissue types, such as healthy tissue versus malignant or cancerous tissue. For example, software 35 may configure signal processor 39 to implement a log-magnitude/phase format ("LMPF") Gauss-Newton reconstruction algorithm as described in "Microwave image reconstruction utilizing log-magnitude and unwrapped phase to improve high-contrast object recovery" by P. M. Meaney, K. D. Paulsen, B. W. Pogue, and M. I. Miga, IEEE Trans. MI, Volume MI-20, 104-116 (2001), incorporated herein by reference. The scattered signals from each of the antennas configured to receive the signals may then be used to reconstruct a conductivity and permittivity image of target 34. The term "scattered" refers to the difference in phase and magnitude between imaging situations when target 34 is present in tank 32 and when target 34 is not present. The differences may be computed in log format for the magnitude and phase angle for the phase (e.g., as a log-magnitude phase format, herein designated "LMPF").

In one embodiment, processor 36 digitally low pass filters the signal from A/D converter 37 such that processor 36 may examine a frequency-isolated (e.g., filtered) version of the demodulated signal. In other embodiments, an analog Low Pass Filter (LPF) is coupled between receivers 22, 26 and A/D converter 37 to perform similar functionality, as is known in the art. While this illustration describes system 10 with two receivers and two antennas, the embodiment is not intended to be limited to the number of receivers and antennas of the illustration; nor is the embodiment intended to be limited to the number of receivers and antennas shown in FIG. 1.

Each of receivers 22 and 26 in one embodiment, includes two amplifiers (e.g., 23, 23A, 27 and 27A, respectively) and a signal multiplier (e.g., 25 and 29 respectively). Amplifiers 23, 27 are configured for amplifying RF signals received from antennas 30, 31; amplifiers 23A and 27A are configured for amplifying the reference carrier signal from a power divider 14. Once amplified, signal multipliers 25, 29 demodulate their respectively received signals by multiplying the signals with the amplified carrier signal.

System 10 includes, in one embodiment, transmitter 16 configured for generating the transmitted signal constructed from the carrier signal and the modulating waveform. Transmitter 16 includes RF signal generator 13 configured for generating the carrier signal. Transmitter 16 also includes signal multiplier 15 and function generator 12. Function generator 12 is coupled to signal multiplier 15, as is RF signal generator 13. Function generator 12 is configured for generating a modulating waveform used to modulate the carrier signal as applied by signal multiplier 15. In another embodiment, function generator 12 is coupled to processor 36 for comparison of the original modulating waveform to that of the extracted demodulated signal. It should be further noted that the transmitter 16 and the associated components may be consolidated into a single transmitter unit, such as Agilent model ESG4432 Signal Generator, to provide the RF, carrier signal and the modulating waveform.

In one embodiment, system 10 includes a power divider 14 that splits the carrier signal from RF signal generator 13 into multiple same signals, typically of lesser magnitude or gain. These signals are applied to signal multipliers 25 and 29 through associated amplifiers 23A and 27A such that receivers 22 and 26 may demodulate received signals.

A switching network 17 applies the transmitted signal to one or more of antennas 30, 31, in one embodiment. For example, switching network 17 may apply the transmitted signal to antenna 30 such that the transmitted signal passes through target 34. Switching network 17, during transmission of the signal via antenna 30, is also configured to receive the transmitted signal via antenna 31 through a switch selection, as described below.

Switching network 17 includes an N-connection switch 20 having an RF input terminal coupled to an output of signal multiplier 15. N-connection switch 20 also has "N" number of RF output terminals selectively coupling antennas 30 and 31 to signal multiplier 15, where N is an integer greater than 1. Switching network 17 also includes transmit/receive switches 24 and 28 respectively coupled for selectively switching between either a receive mode or a transmit mode of antennas 30 and 31. To illustrate, as N-connection switch 20 is selected (e.g., closed) at node 20A to transmit the signal from signal multiplier 15 amplified by amplifier 21A, transmit/receive switch 24 is selected (e.g., "closed") to node 24B for conducting the signal to antenna 30. Accordingly, N-connection switch 20 is "open" at node 20B. Transmit/receive switch 28 is selected (e.g., closed) at node 28B to receive, via antenna 31, the signal transmitted through antenna 30. While this embodiment illustrates one manner in which an antenna transmits one signal and other antennas receive the transmitted signal by means of switching network 17, this embodiment is not intended to be limited to the selection of transmit and receive antennas described herein. For example, multiple transmitters, each generating a transmitted signal with a unique carrier frequency, may be employed such that switching network 17 selectively transmits through a plurality of antennas and selectively receives through a plurality of antennas.

Figure 2:
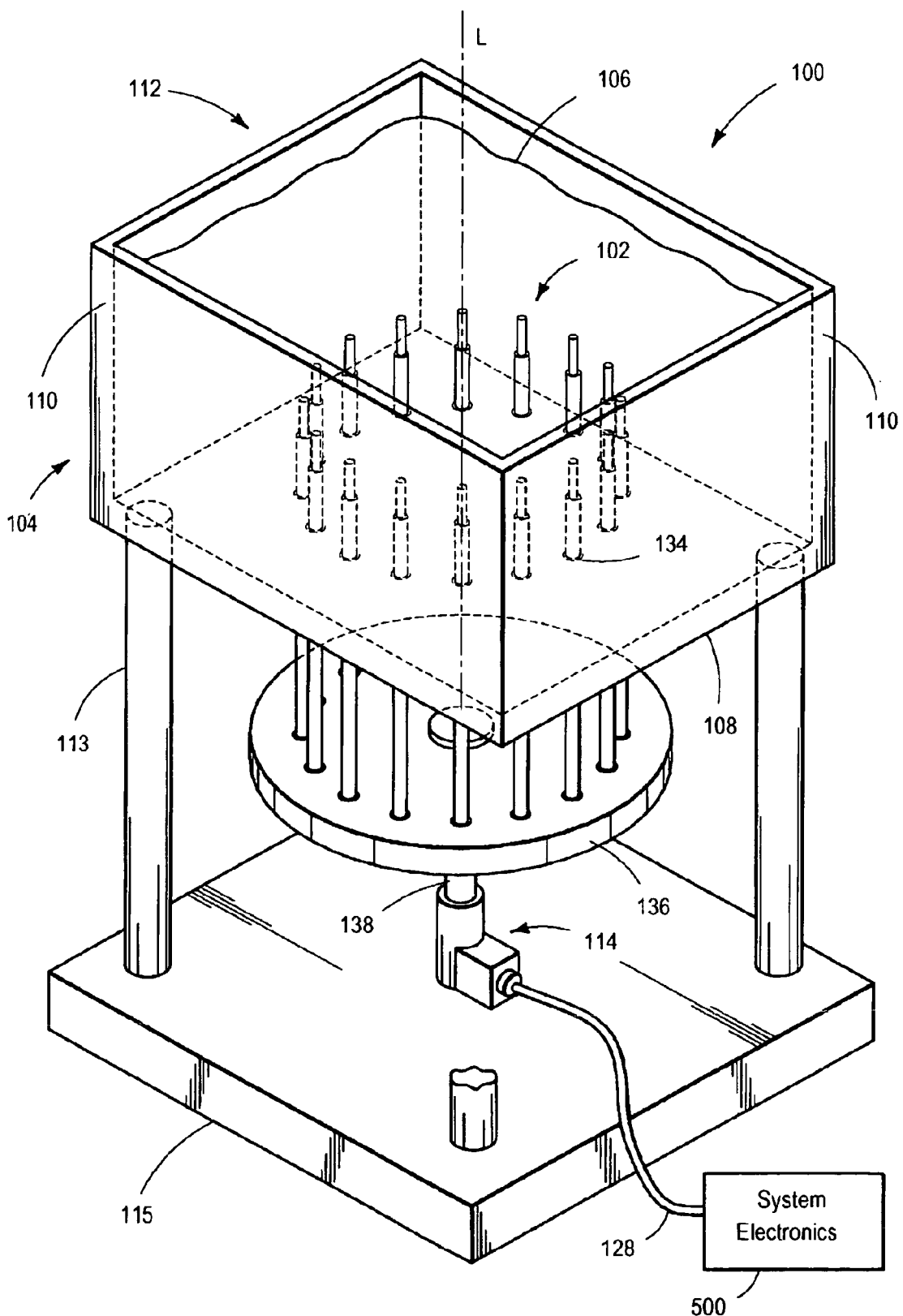
FIG. 2 is a perspective view of one illumination tank assembly for the microwave imaging system of FIG. 1, in accord with one embodiment.
Figure 3:
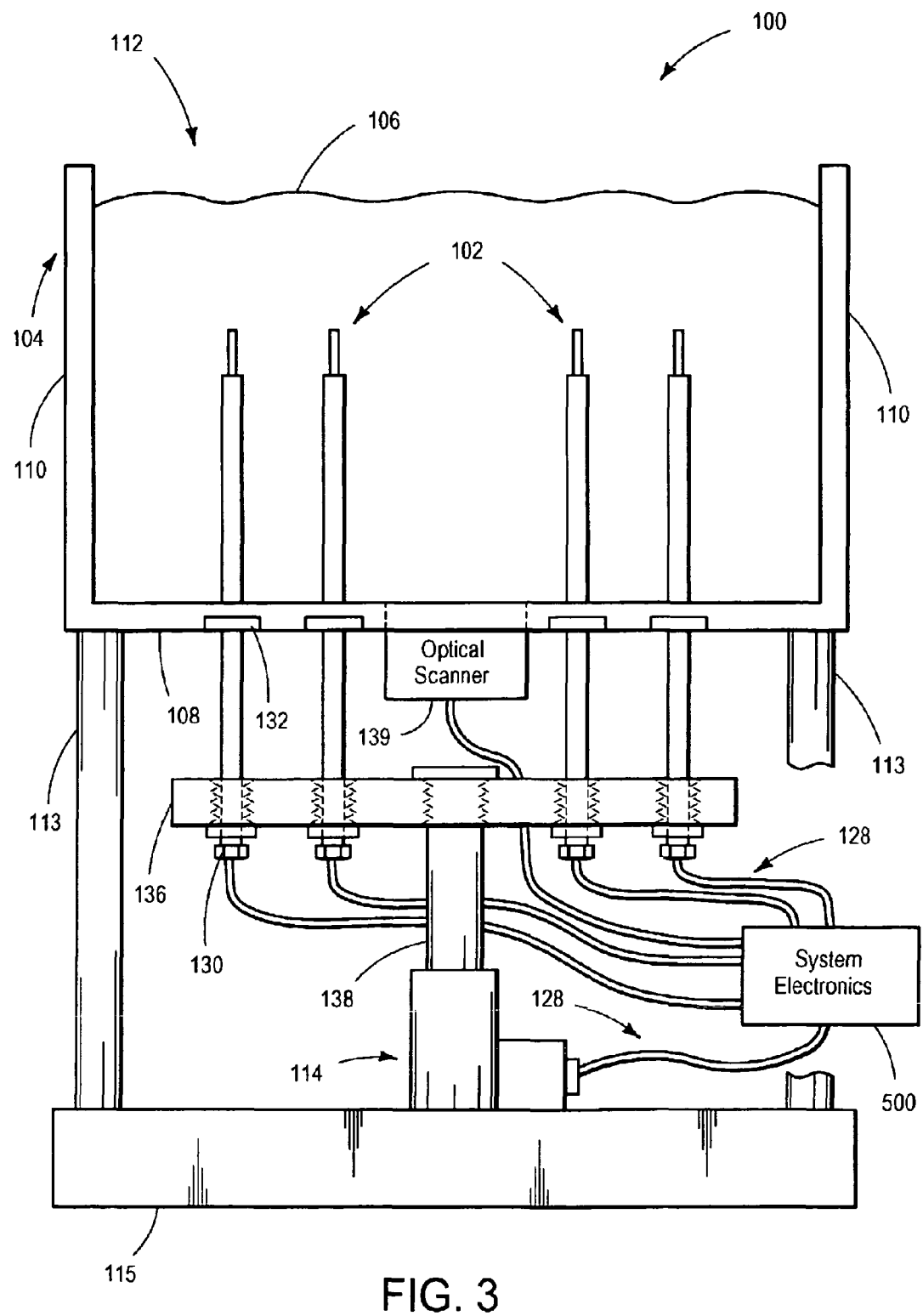
FIG. 3 is a side elevational view of the illumination tank assembly of FIG. 2.

FIGS. 2 and 3 show one illumination tank assembly 100 for microwave illumination of a target. Array of antennas 102 extends into an illumination tank 104 holding a volume of a liquid coupling medium 106. Liquid coupling medium 106 facilitates the transmission of microwave-frequency RF signals from the antennas 102 to and through the target (e.g., target 34, FIG. 1, which may be biological tissue) and back to antennas 102. The specific physical properties of liquid coupling medium 106 will be discussed more fully herein. Illumination tank 104 may have a base 108 and one or more sidewalls 110 depending on the shape of the tank (e.g., one sidewall if the tank is cylindrical in shape, multiple sidewalls if another shape). The array of antennas 102 preferably surrounds a target to be imaged (e.g., target 34, FIG. 1, which may be human in vivo tissue, such as breast tissue) that extends into liquid coupling medium 106 through an open end 112 of illumination tank 104. Array of antennas 102 illuminates the target with microwave-frequency RF signals. In one embodiment, array of antennas 102 includes 16 individual antennas; however, any number of antennas may be used depending on the desired amount of imaging detail. In FIG. 3, only 4 antennas are depicted for clarity of assembly 100 and the components thereof. An actuator 114, for example a computer-controlled linear actuator (not shown), may drive the movement of the array of antennas 102 vertically along a longitudinal axis L of illumination tank 104 such that microwave-frequency RF signals may be transmitted and received by antennas 102 at varying transverse, or horizontal, imaging planes orthogonal to the longitudinal axis L and through the target. Actuator 114, and other components of assembly 100, including illumination tank 104, may be supported by a base support 115; a series of legs 113 may extend downward from illumination tank 104 to the base to support tank 104. Base support 115 may be provided with wheels (not shown) such that at least a portion of assembly 100 supported by base support 115 is portable and may be easily moved across a surface.

Figure 4:
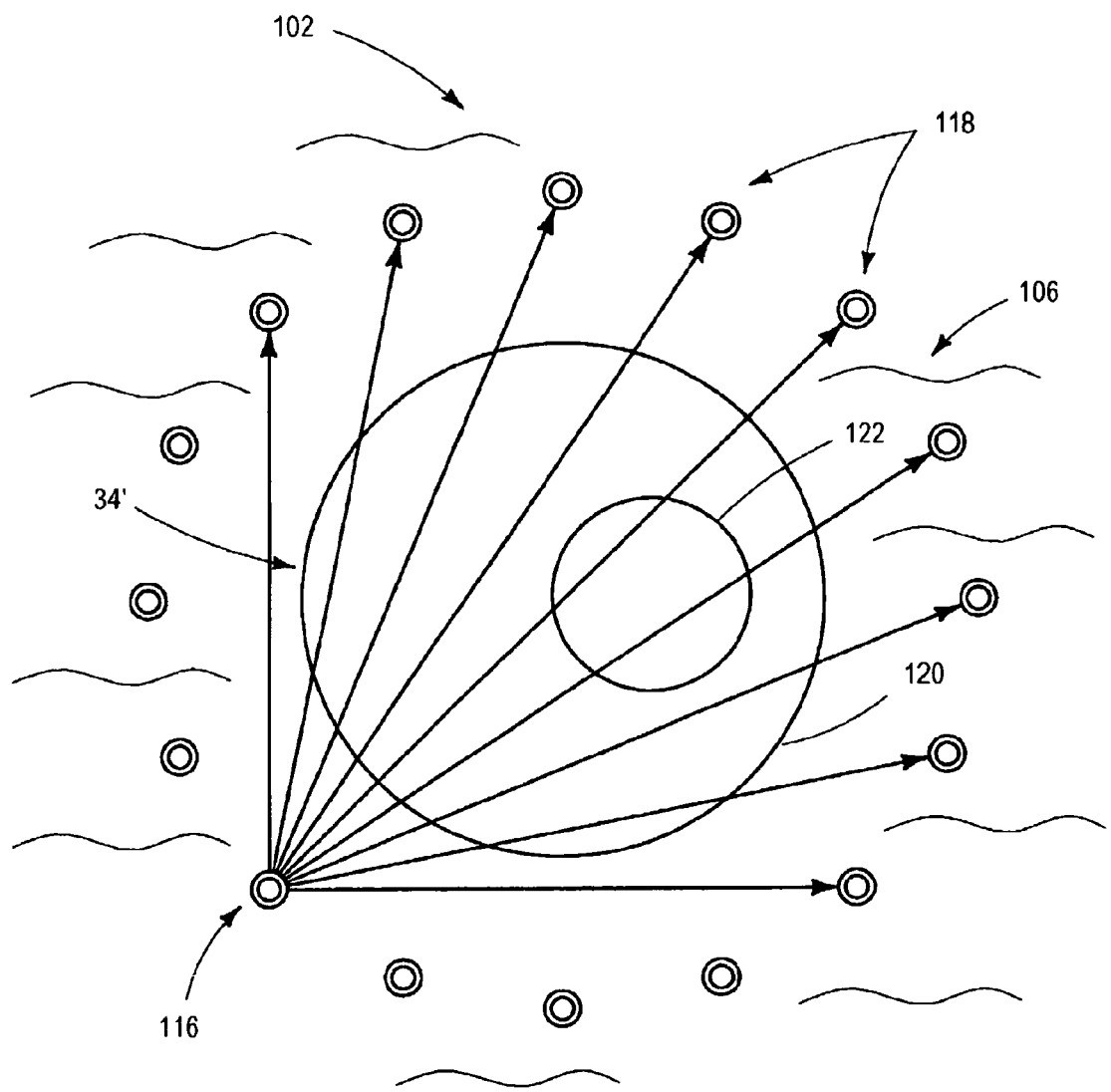
FIG. 4 is a schematic diagram of an array of antennas and straight line signal projections propagated through a target having regions of varying conductivity and permittivity.

FIG. 4 shows one antenna 116 of the array of antennas 102 transmitting microwave-frequency RF signals that are received by other antennas 118 of the array of antennas 102. A portion of these transmitted signals are propagated through a first portion 120 of target 34' (e.g., target 34, FIG. 1), and another portion of such signals are propagated through both first portion 120 and a second portion 122 of target 34', each portion having a unique set of conductivity and permittivity characteristics. It should be noted that the target 34' and antenna array 102 are submerged in liquid coupling medium 106 in illumination tank 104. It is the varying conductivity and permittivity characteristics, or electrical properties, of the first and second portions 120, 122 that may be mapped for each chosen transverse imaging plane through target 34'. This mapping shows where non-uniform regions exists in target 34' which may correspond to tissue abnormalities, such as malignancy. For example, when imaging breast tissue, first portion 120 may correspond to healthy tissue and second portion 122 may correspond to otherwise abnormal and/or malignant tissue.

System electronics 500 (e.g., transmitter 16, power divider 14, switching network 17, receivers 22, 26, memory 33 and processor 36 executing software 35, FIG. 1) provide control over the operation of actuator 114 and the generation and reception of microwave signals through the array of antennas 102. As shown in FIG. 3, coupling of system electronics 500 to the array of antennas 102 and actuator 114 may be through communication cables 128 (e.g., coaxial electrical cables, fiber optic cables or digital electronic ribbon cables) as a matter of design choice. Communication cables 128 coupling the array of antennas 102 and system electronics 500 are omitted from FIG. 2 for clarity. Each antenna 102 has a connector 130 formed therewith to which one communication cable 128 is attached. Upon generation of a microwave-frequency RF signal by system electronics 500, such signal is carried by one or more of communication cables 128 to the respective antenna 102 for transmission. As with system 10 of FIG. 1, the microwave-frequency RF signals are, for example, signals ranging in frequency from 300 MHz to 3 GHz. Other frequencies may also be used as a matter of design choice depending on the electrical properties of liquid coupling medium 106 and target 34'. Since the electrical properties of the various portions of target 34' vary depending on the frequency of microwave transmission, a more complete mapping of non-uniform regions in target 34' may be realized by imaging at a number of transmission frequencies. Transmitting antenna 116 of the array of antennas 102 then transmits the microwave signal through target 34', as shown in FIG. 4. Receiving antennas 118 then detect the microwave signals propagated through target 34', and send the detected signals through the respective communication cables 128 back to system electronics 500. Each antenna that may act as a receiving antenna 118 has a receiver (e.g., receivers 22, 26, FIG. 1) associated therewith. System electronics 500 may then store the signal information received and reconstruct maps of the conductivity and permittivity characteristics of target 34'. The array of antennas 102 may all be positioned in the same transverse plane through target 34' so that the conductivity and permittivity characteristics of target 34' (representative of signals that traveled in the transverse plane from transmitting antenna 116 to receiving antenna 118) may be mapped at specific vertical elevations of target 34'.

Once data acquisition is completed at a specified transverse plane through target 34', actuator 114 may move the array of antennas 102 vertically up or down to select imaging at another vertical elevation of target 34' (i.e., another transverse plane). The vertical movement of the array of antennas 102 with actuator 114 positioned outside of illumination tank 104 is facilitated by extending antennas 102 through a series of seals 132 (e.g., Teflon hydraulic seals) disposed within bores 134 formed into base 108 of illumination tank 104, as shown in FIG. 2. Seals 132 facilitate relatively low-friction translation of antennas 102 while preventing liquid coupling medium 106 from leaking out of illumination tank 104. The array of antennas 102 may be mounted onto a mounting platform 136 that is moved vertically by a drive shaft 138 connected with actuator 114. By the arrangement of assembly 100, system electronics 500 are fully positioned outside of illumination tank 104; this is advantageous because of the vulnerability of electronics to being compromised by liquid coupling medium 106 in tank 104. In another arrangement, an actuator 114 may be provided for each individual antenna of the array of antennas 102 such that each antenna may be positioned vertically and independently.

After a series of digital acquisitions at differing transverse planes through target 34' vertically adjusted by actuator 114, target 34' may be optically scanned. An optical scanner 139 may be mounted with illumination tank base 108 either within illumination tank 104 or just below tank 104 scanning through an optically clear portion of base 108. The reconstruction of the microwave images, knowing the vertical elevation of each transverse plane with respect to target 34', may then be spatially co-registered with a 3-D rendering of the exterior of the target 34' (e.g., breast tissue) that has been optically scanned such that non-uniform regions or other abnormalities imaged may be located with a specific visual reference to target 34'. Alternatively, optical scanning of target 34' may take place transversely through optically clear portions of illumination tank sidewalls 110, or the external dimensions of target 34' may be determined using ultrasound or mechanical measuring devices without optical scanning.

Figure 5A:
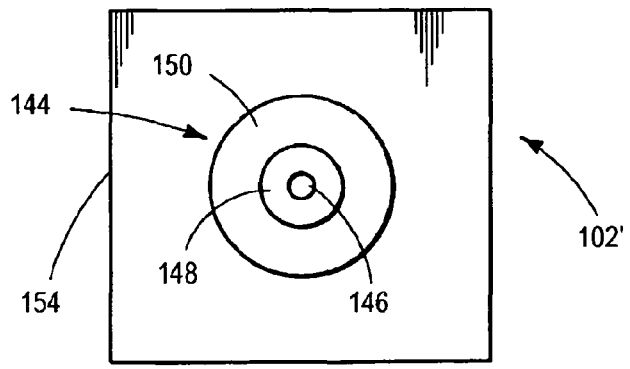
FIG. 5A is a top plan view of a monopole antenna.
Figure 5B:
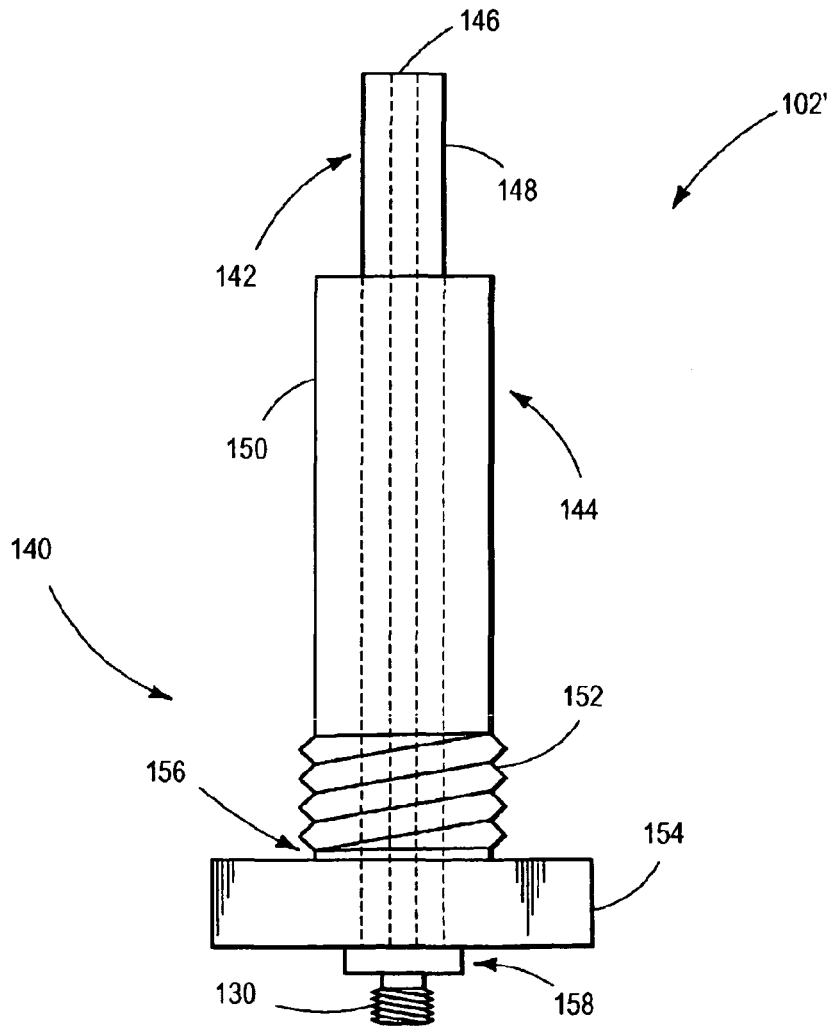
FIG. 5B is a side elevational view of the monopole antenna of FIG. 5A.

The array of antennas 102 of FIGS. 2 and 3 may be formed as monopole antennas 102', as shown in FIGS. 5A and 5B. Each monopole antenna 102' has a base region 140 and a tip region 142 extending therefrom. Base region 140 may be formed of a rigid coaxial cable 144 with a center conductor 146, a cylindrical insulator 148, such as a Teflon insulator, and a rigid, cylindrical outer conductor 150. Base region 140 may also have threads 152 formed onto the outer conductor 150 for securing antenna 102' into a threaded bore of mounting platform 136, and a mounting flange 154 disposed at a terminating end 156 of the outer conductor 150 to abut mounting platform 136. Tip region 142 is formed of coaxial cable 144 without outer conductor 150, and is the portion of monopole antenna 102' responsible for direct transmission and reception of microwave-frequency RF signals with liquid coupling medium 106. In this arrangement, base region 140, having center conductor 146 and cylindrical insulator 148 contiguous with tip region 142, acts as a transmission line for signals traveling between tip region 142 and connector 130. Connector 130 may be of any type connector for coupling coaxial cable 144 with communications cable 128, such as a N-connector, SMA, SMB, etc., the particular connector depending on the type of cable 128 (e.g., electrical or fiber optic cable). Connector 130 may also be formed onto a lower end 158 of center conductor 146 and cylindrical insulator 148 below mounting flange 154.

Figure 6:
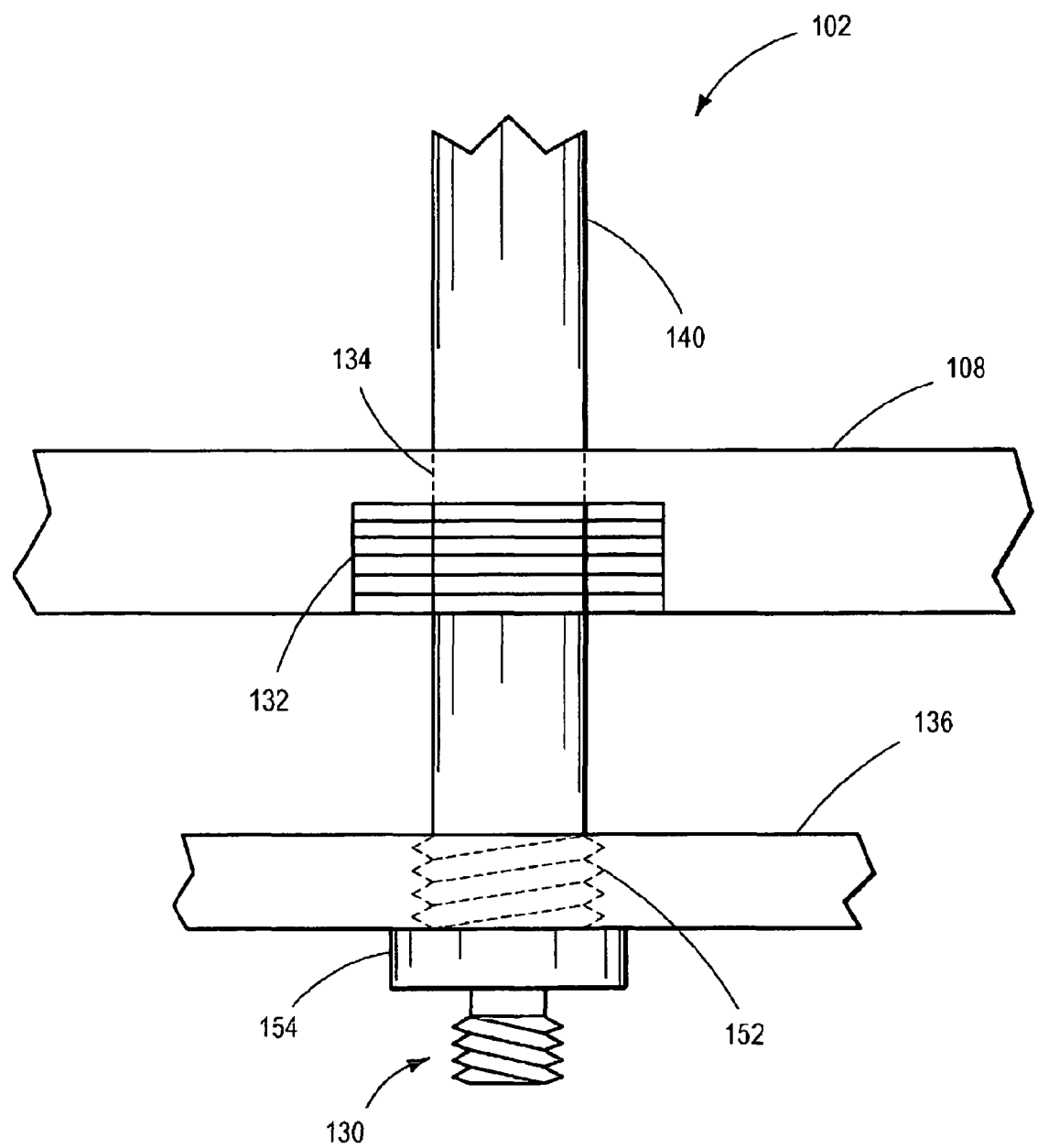
FIG. 6 shows details of the illumination tank assembly of FIG. 2.

FIG. 6 shows the details of one of the array of antennas 102 extending through bores 134 of illumination tank base 108 and mounted onto mounting platform 136. Base region 140 of each antenna 102 is surrounded by one or more seals 132 stacked within bore 134 and is shown with threads 152 threadingly received into the threaded bore of mounting platform 136. The number of seals 132 and tolerance with the diameter of base region 140 should be sufficient to withstand the forces induced by the antennas 102 sliding therethrough under the influence of actuator 114 without leakage of liquid coupling medium 106 through seals 132.

Figure 7:
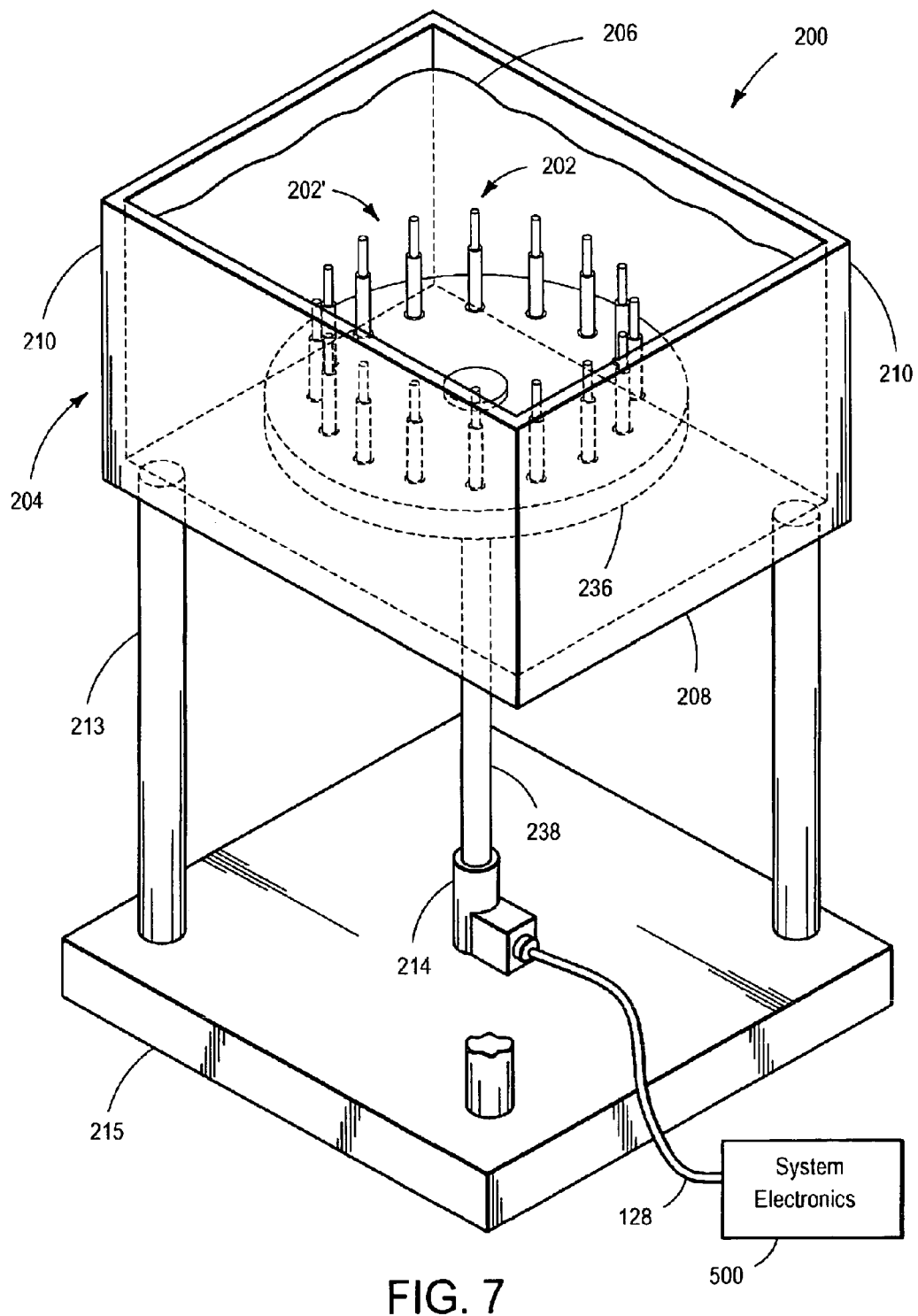
FIG. 7 is a perspective view of another illumination tank assembly utilizing monopole antennas.
Figure 8:
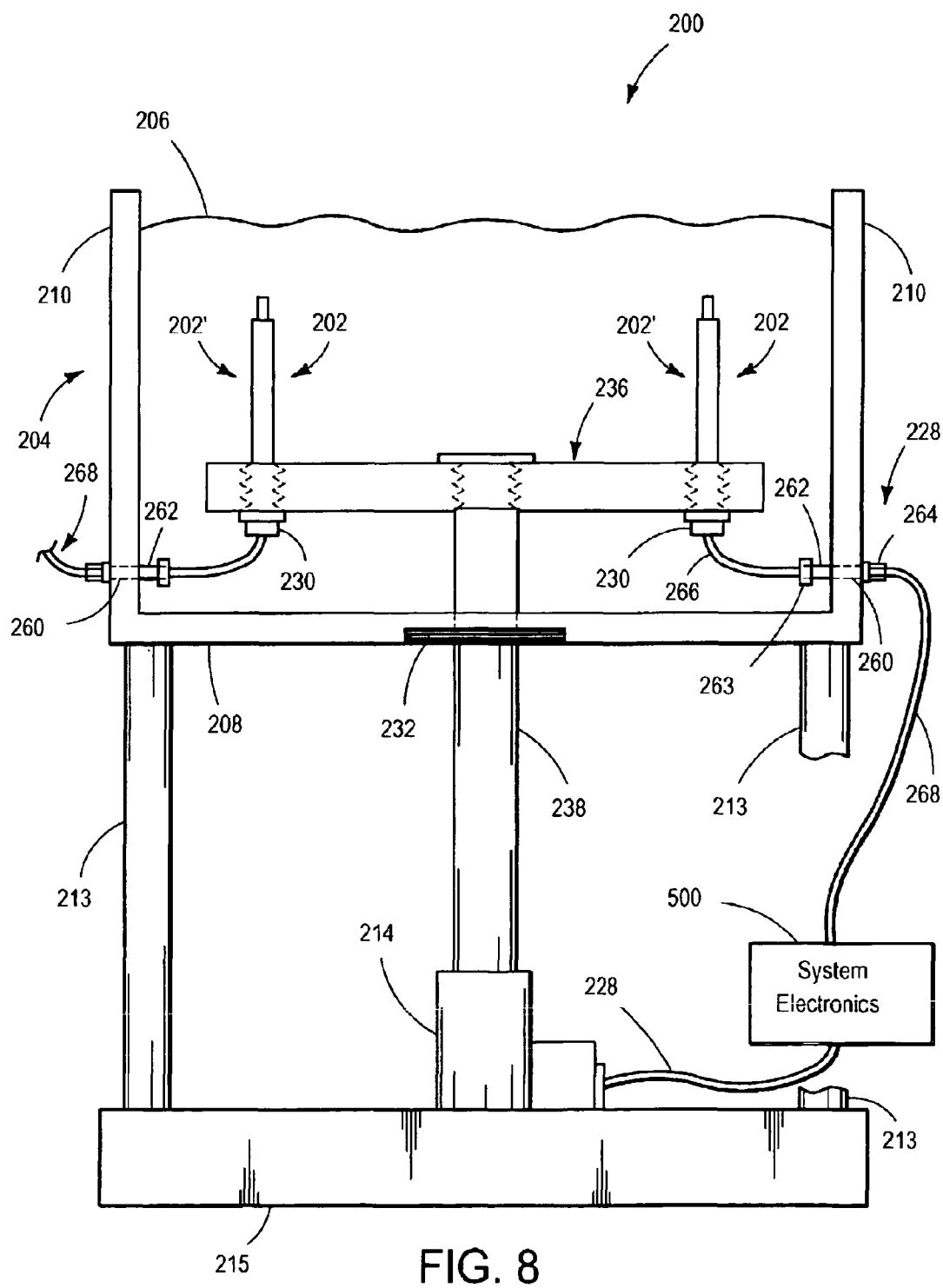
FIG. 8 is a side elevational view of the illumination tank assembly of FIG. 7.

FIGS. 7 and 8 show another illumination tank assembly 200 having similar components to assembly 100 of FIGS. 2 and 3. Assembly 200 has all regions of an array of antennas 202 and a mounting platform 236 disposed within an illumination tank 204. Drive shaft 238 extends through seals 232 into illumination tank 204, as opposed to assembly 100 of FIGS. 2, 3 and 6, where the array of antennas 102 extend through seals 132. The array of antennas 202 may surround a target in the same arrangement as assembly 100 of FIGS. 2 and 3. In FIG. 8, only 2 antennas are depicted for clarity of assembly 200 and the components thereof, but any number of antennas may be implemented (e.g., 16 antennas). Antennas 202 may also be monopole antennas 202' having the arrangement shown for monopole antenna 102' of FIGS. 5A and 5B. Communications cables 228, connected with a connector 230 of each antenna 202, may be routed through a liquid coupling medium 206 upward and out of illumination tank 204 over a sidewall 210 to system electronics 500. Communications cables 228 extending from antennas 202 to system electronics 500 are omitted from FIG. 7 for clarity. Alternatively, bores 260 may be extended through any of the illumination tank sidewalls 210 or base 208 such that each communication cable 228 may exit illumination tank 204 proximal to illumination tank base 208 to communicatively couple antennas 202 with system electronics 500. In this arrangement, communications cables 228 are less likely to interfere with any target placed in illumination tank 204. One configuration for preventing liquid coupling medium 206 from leaking out of illumination tank 204 through the tolerance space between communications cables 228 and associated bores 260 is to use a coaxial bulkhead feed through adapter 262. Bulkhead adapter 262 may be, for example, a female-to-female SMA type adapter, with male connectors 263, 264 (e.g., SMA type connectors) secured to opposing ends thereof. Bulkhead adapter 262 thus facilitates improved communications cable management in assembly 200 by positioning cables so as to provide minimal spatial interference with operation of the system. A first communications cable section 266 may be attached to connector 230 on one end and to bulkhead adapter 262 via male connector 263 disposed within illumination tank 204 on the opposing end, and a second communications cable section 268 may be attached to bulkhead adapter 262 via male connector 264 disposed outside of tank 204 on one end, and to the system electronics 500 on the opposing end. Enough length of first communications cable section 266 should be provided to allow for a range of vertical movements of the attached array of antennas 202 by actuator 214. Similar to assembly 100 of FIGS. 2 and 3, actuator 214, and other components of assembly 200, including illumination tank 204, may be supported by a base support 215, and legs 213 may support tank 204 above base support 215.

Figure 9:
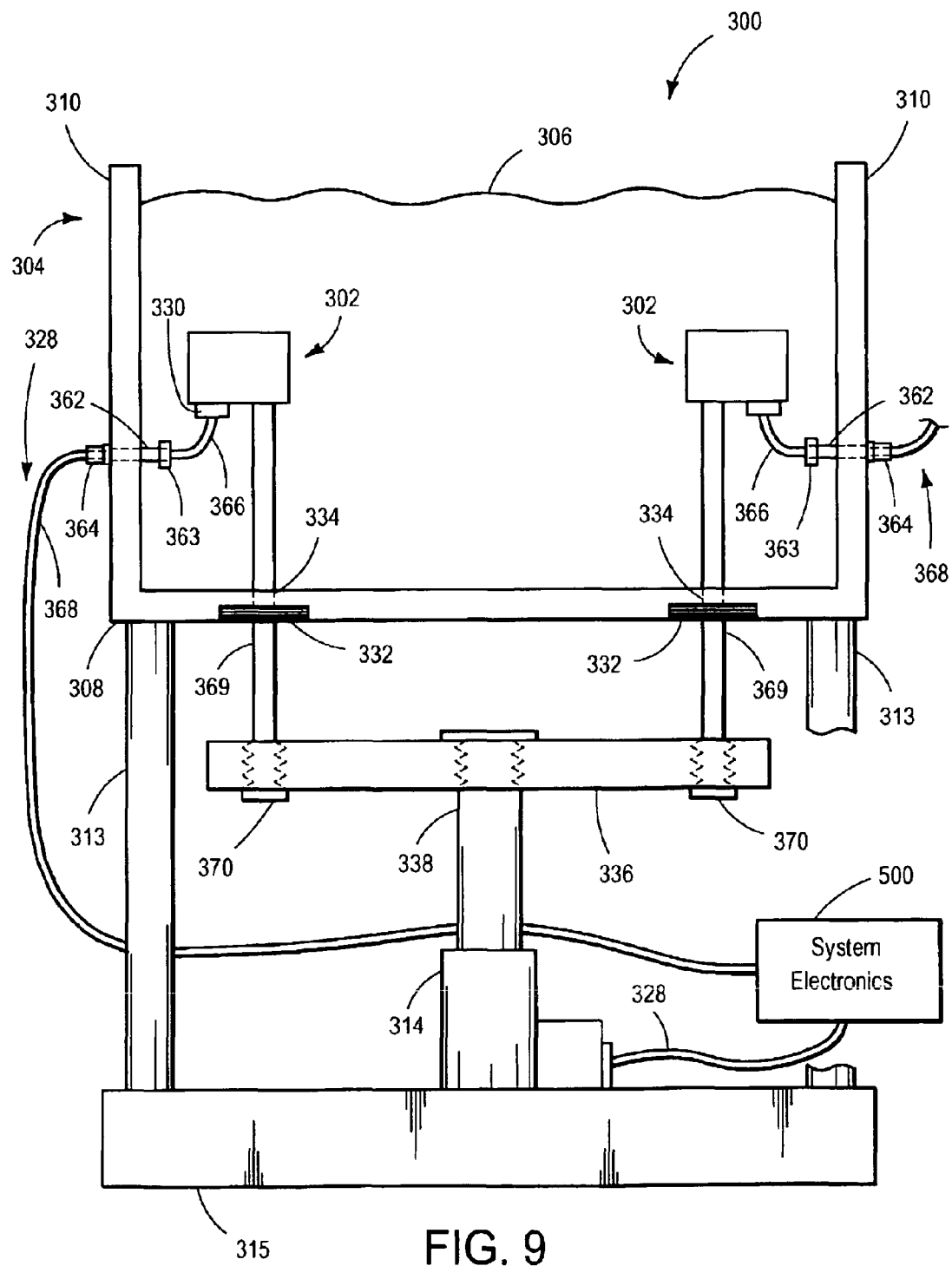
FIG. 9 shows another microwave imaging assembly.

Another microwave imaging assembly 300 is shown in FIG. 9. Assembly 300 is similar to assembly 100 of FIGS. 2 and 3, and assembly 200 of FIGS. 7 and 8, but specifically uses an array of waveguide antennas 302. The array of waveguide antennas 302 may surround a target in the same arrangement as assembly 100 of FIGS. 2 and 3, and assembly 200 of FIGS. 7 and 8. FIG. 9 only shows 2 waveguide antennas for clarity of assembly 300 and the components thereof, but any number of waveguide antennas may be implemented; moreover, other types of antennas may be implemented, including but not limited to monopole antennas (e.g., antenna 102', FIG. 5A), dipole antennas, spiral antennas, ridge waveguide antennas and patch antennas. In assembly 300, the arrangement of an actuator 314, a drive shaft 338 and a mounting platform 336 may be the same as in assembly 100 of FIGS. 2 and 3. Instead of antennas 102 extending through illumination tank base 108 into illumination tank 104, an array of support rods 369 extend through seals 332 disposed within bores 334 formed into an illumination tank base 308. Each support rod 369 has one waveguide antenna 302 mounted therewith on an upper end, and a mounting flange 370 formed at a lower end of the rod 369 to abut mounting platform 336. Support rods 369 may also be threadingly received into threaded bores of mounting platform 336 for mounting thereon.

Similar to assembly 200 of FIGS. 7 and 8, communications cables 328 connected with a connector 330 of each waveguide antenna 302 may be routed through liquid coupling medium 306 upward and out of an illumination tank 304 over one or more sidewalls 310 to system electronics 500. Alternatively, the bulkhead adapter arrangement shown in FIGS. 7 and 8 may be implemented as shown in FIG. 9 to communicatively couple waveguide antennas 302 with system electronics 500. Thus, a first communications cable section 366 may attached to connector 330 on one end and to bulkhead adapter 362 via male connector 363 disposed within illumination tank 304 on the opposing end, and a second communications cable section 368 may be attached to bulkhead adapter 362 via male connector 364 disposed outside of tank 304 on one end, and to system electronics 500 on the opposing end, bulkhead adapter 362 spanning between male connectors 363, 364. Similar to assembly 100 of FIGS. 2 and 3, actuator 314, and other components of assembly 300, including illumination tank 304, may be supported by a base support 315, and legs 313 may support tank 304 above base support 315.

In an alternative arrangement for assembly 300, mounting platform 336 and drive shaft 338 may be positioned in the same configuration as in assembly 200 of FIGS. 7 and 8, with drive shaft 338 extending through seals 332 into illumination tank base 308 through a single bore 334. The array of support rods 369 would then be fully positioned within illumination tank 304.

Figure 10:
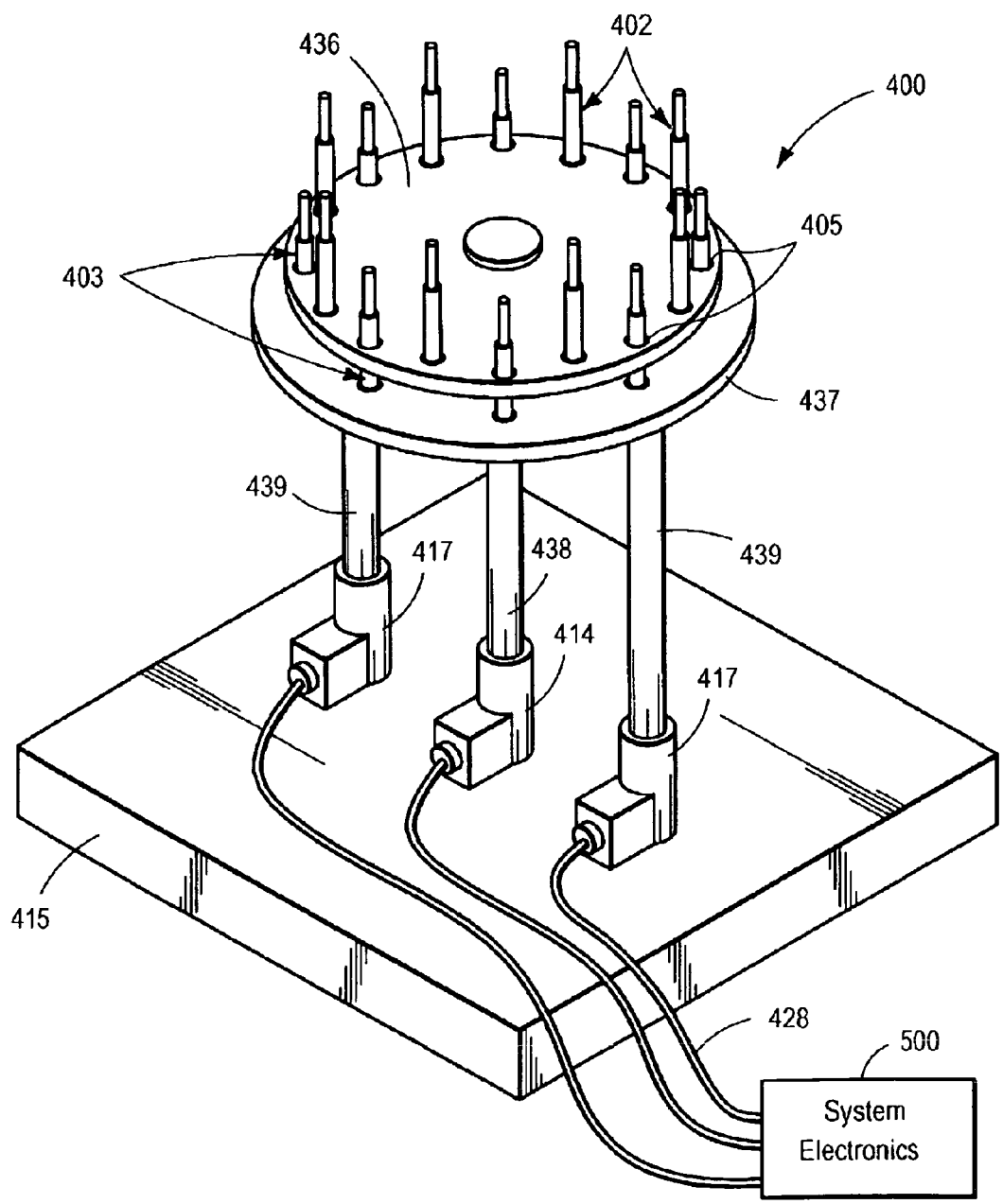
FIG. 10 is a perspective view of another illumination tank assembly with first and second arrays of antennas.
Figure 11:
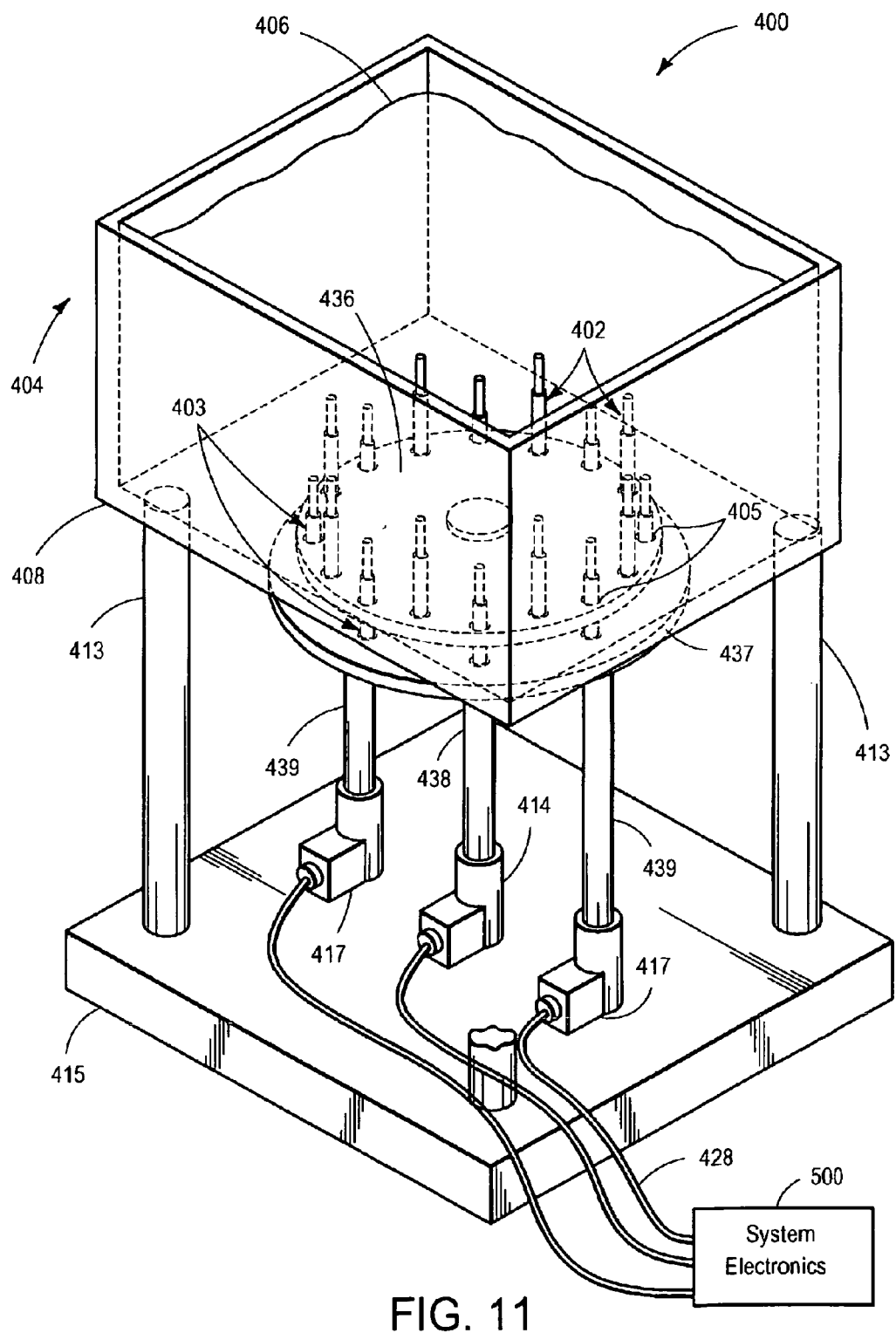
FIG. 11 is a perspective view of the illumination tank assembly of FIG. 10 showing the first and second arrays of antennas inside an illumination tank.
Figure 12:
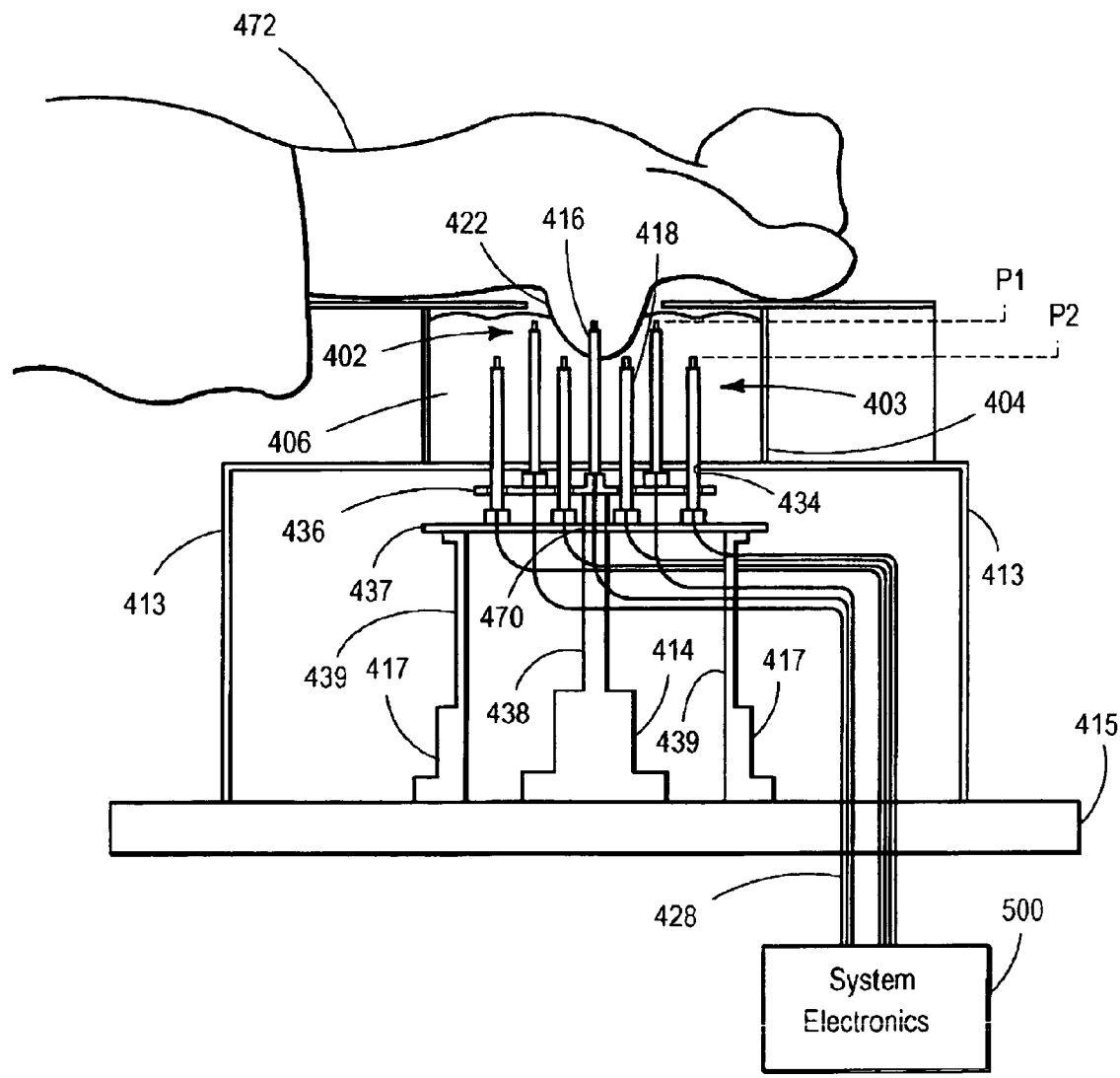
FIG. 12 is a schematic diagram of the illumination tank assembly of FIG. 10 showing application of the system for imaging in vivo tissue of a human.

FIGS. 10-12 show another illumination tank assembly 400 utilizing two different, independently controlled arrays of antennas to perform 3-D microwave imaging of a target that is, in this case, biological tissue. This arrangement goes beyond performing data acquisition in a series of transverse slices at various vertical elevations of the biological tissue being imaged, because microwave-frequency RF signals may be transmitted by an antenna array 402 at one vertical elevation, and received by an antenna arrays 403 at another vertical elevation. Thus, microwave-frequency RF signals propagating out of a transverse plane aligned with a transmitting antenna may be detected.

FIG. 10 shows assembly 400 without an illumination tank 404 and communications cables 428 that connected antenna array 402 to system electronics 500, for clarity of the assembly layout. A first array of antennas 402 may be vertically positionable by a first actuator 414 at a first transverse plane $P_1$, and a second array of antennas 403 may be vertically positionable by one or more second actuators 417 at a second transverse plane $P_2$. Actuators 414, 417 may be controlled by system electronics 500 coupled therewith by communications cables 428. First and second actuators 414, 417, as well as other components of assembly 400, may also be supported by a base support 415 in a similar fashion to assembly 100 of FIGS. 2 and 3.

In one embodiment, the arrays of antennas 402, 403 are disposed in an interleaved, circular arrangement with a common diameter. Each array of antennas 402, 403 may include, for example, 8 individual antennas, for a total of 16 antennas between the two antenna arrays; however, the number of antennas used may depend on the desired amount of imaging detail. The antenna arrays 402, 403 may comprise monopole antennas, waveguide antennas, or other antenna types that are compatible with the transmission and reception of microwave signals. By positioning a transmitting antenna 416 of one antenna array (e.g., first array 402) at a different vertical elevation with respect to biological tissue 422 than one or more receiving antennas 418 of the other array (e.g., second array 403), as shown in FIG. 12, data acquisition may take place for out-of-plane propagation. The vertical distance between the antenna arrays 402, 403, and the particular location of transmitting antenna 416 and each receiving antenna 418, will dictate the nature of the out-of-plane propagation. The transmission and reception of microwave-frequency RF signals may also take place with antennas in the same array of antennas, such that data collection is in a transverse plane (e.g., one of transverse planes $P_1$ or $P_2$), as is done by assembly 100 of FIGS. 2 and 3. Thus, the combination of data acquisition in selectable transverse planes and out-of-plane configurations, provides true 3-D data gathering of the microwave-frequency RF signals propagated through and/or around biological tissue 422 (i.e., in vivo breast tissue). An optical scanner (not shown) may be positioned to image the in vivo tissue within illumination tank 404, as done by optical scanner 139 of FIG. 3, for spatially co-registering reconstructed image data of the microwave-frequency RF signals with a 3-D rendering of object surface.

Dividing antennas into first and second arrays 402, 403 reduces the data acquisition times associated with collecting measurements for 3-D microwave tomographic imaging because the number of possible vertical antenna position permutations for signal detection is decreased compared to the case where a single actuator controlled each antenna. Additionally, the alternative of acquiring sufficient 3-D data using a fixed 3-D antenna array for microwave imaging requires a very large number of antennas, which significantly increases the expense of the assembly because of the associated complex circuitry that would be necessary.

One exemplary arrangement for assembly 400 provides a pair of second actuators 417 each having a drive shaft 439 for vertically moving second mounting platform 437 mounted therewith. Second array of antennas 403 are mounted upon second mounting platform 437, and surround a hole 470 through which a drive shaft 438, vertically movable by first actuator 414, extends. A first mounting platform 436 is mounted with drive shaft 438 and has first array of antennas 402 mounted thereon. First mounting platform 436 overlaps second mounting platform 437 vertically over second array of antennas 403 and has an array of holes 405 extending therethrough and disposed between first array of antennas 402. Holes 405 are configured such that second array of antennas 403 may be extended through first mounting platform to form first and second antenna arrays 402, 403 into an interleaved, circular group of antennas. Alternatively, another arrangement for first and second actuators 414, 417 of assembly 400 may include actuator 414 connected to first mounting platform 436 through drive shaft 438 and a single second actuator 417 centrally positioned on top of first mounting platform 436 and connected to second mounting platform through drive shaft 439.

FIG. 11 shows how first and second antenna arrays 402, 403 extend through an illumination tank base 408 into a liquid coupling medium 406 within illumination tank 404. Seals (e.g., seals 132 of FIG. 3) are positioned within bores 434 formed into illumination tank base 408 through which the antennas 402, 403 extend. Similar to assembly 100 of FIGS. 2 and 3, legs 413 may support illumination tank 404 above base support 415.

A schematic illustration of a patient 472 undergoing a microwave imaging procedure is shown in FIG. 12. Patient 472 lies prone on a support table with breast tissue 422 as the particular in vivo biological tissue that is to be imaged pendant in liquid coupling medium 406 of illumination tank 404. First and second actuators 414, 417 then selectively vertically position first and second antenna arrays 402, 403, respectively, to surround differing portions of breast tissue 422. Microwave-frequency RF signals may then be transmitted by transmitting antenna 416 and received by any number of receiving antennas 418 in either or both of the first and second antenna arrays 402, 403, depending on the particular microwave imaging scheme. Transmitting antenna 416 may, of course, be located on either of the antenna arrays 402, 403. Alternatively, illumination tank assembly 400 could be configured in a similar fashion to assembly 200 of FIGS. 7 and 8, where drive shafts 438, 439 extend through bores 434 into illumination tank 404 such that antennas arrays 402, 403 and mounting platforms 436, 437 are positioned fully within tank 404.

When utilizing system 10 of FIG. 1, assembly 100 of FIGS. 2 and 3, assembly 200 of FIGS. 7 and 8, assembly 300 of FIG. 9, and assembly 400 of FIGS. 10 and 11, as medical microwave imaging data acquisition systems, a permittivity-compatible liquid coupling medium is desired. Improved microwave imaging of the electrical properties (e.g., conductivity and permittivity) for certain types of targets (especially in vivo biological tissue, in one example, human breast tissue) are realized by the addition of glycerol to water, or glycerol to a saline solution, to form liquid coupling media 106, 206, 306 and 406 of microwave imaging systems 100, 200, 300 and 400, respectively. Glycerol may be referred to as "glycerine" herein, and the glycerine/water or glycerine/saline mixtures may be referred to generally as "glycerine mixtures". Reduction of the contrast between the particular liquid coupling medium and the imaged object, achieved by the glycerine mixtures, is one method for improving imaging performance. The low permittivity characteristics of the glycerine mixtures may provide the benefits of: (a) reduction of 3-D wave propagation image artifacts when imaging schemes assume a 2-D model, (b) reduction of the effective imaging slice thickness when imaging in a transverse plane through the imaged object, (c) improvement in property characterization for large, low permittivity scatters, and (d) improved inclusion detection within the imaged object and artifact reduction. 3-D wave propagation image artifacts are typically more problematic when using a relatively large diameter array of antennas, and when lower frequency microwaves are used for imaging; however, the glycerine mixtures minimize the effects regardless of array diameter and frequencies of microwave transmission.

Figure 13:
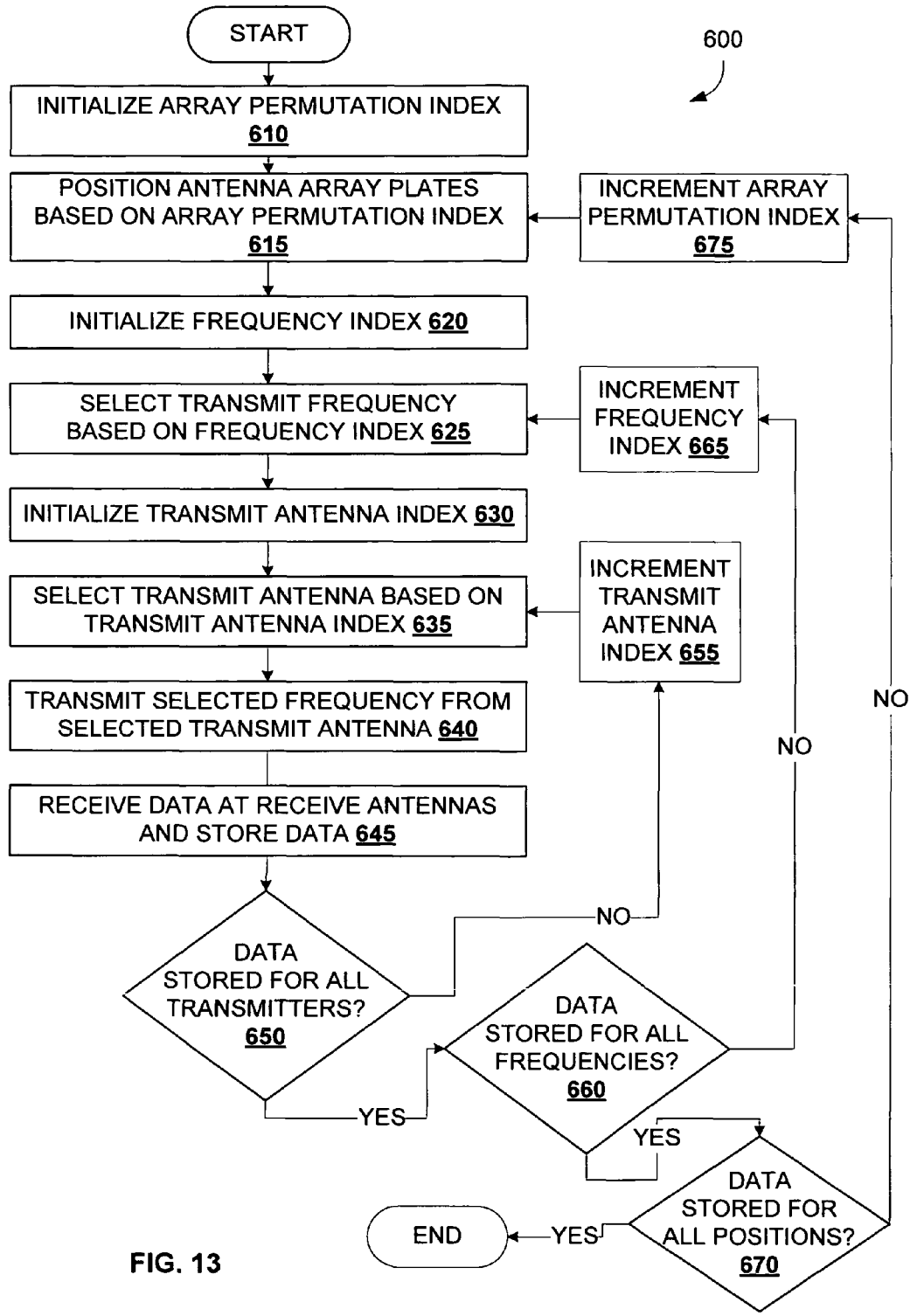
FIG. 13 is a flowchart illustrating exemplary steps of one microwave imaging process.

FIG. 13 is a flowchart illustrating exemplary steps of a microwave imaging process 600. Process 600 is for example implemented by microwave imaging system 10, with processor 36 executing software 35 (see FIG. 1). Process 600 generates and stores scattered microwave data at multiple microwave frequencies, and/or over multiple positions of transmit and receive antennas, for use in reconstructing images of a target.

Microwave imaging utilizing multiple microwave frequencies may be advantageous in that lower frequency data helps to stabilize convergence of iterative reconstruction calculations, while higher frequency (shorter wavelength) data provides images with higher resolution. Furthermore, in addition to images of permittivity and/or conductivity that are independent of frequency, images of parameters such as frequency dispersion coefficients can be reconstructed. Such images may yield new insights into the properties of the target (e.g., may supply different diagnostic information for breast cancer detection or localization) than is available with imaging that utilizes a single frequency. In the microwave frequency range, dielectric properties often vary in relatively predictable and smooth patterns with respect to frequency (in the microwave field such variations are called the dispersion of the electrical properties). For each pixel in an image, a frequency relationship may be assumed, wherein the coefficients in the relationship are unknown. For instance, the relationship:

$$\epsilon_r = A\omega + B \quad \text{(Eq. 1)}$$

where $\epsilon_r$ is the relative permittivity and $\omega$ is the frequency in radians, would imply that the permittivity varied linearly with the frequency and that the coefficients A and B are unknown. Other possibilities of frequency relationships (using permittivity relationships as examples) include:

a log-linear relationship:

$$\ln \epsilon_r = A\omega + B \quad \text{(Eq. 2)}$$

a linear-log relationship:

$$\epsilon_r = A \log \omega + B \quad \text{(Eq. 3)}$$

a log-log relationship:

$$\ln \epsilon_r = A \ln \omega + B \quad \text{(Eq. 4)}$$

and a polynomial expansion:

$$\varepsilon_r = \sum_{i=0}^{N} A_i \omega^i \quad \text{(Eq. 5)}$$

where $\epsilon_r$ is the relative permittivity, $\omega$ is the angular frequency, and A, $A_i$, and/or B are coefficients. The same types of relationships as shown above for $\epsilon_r$ could also be developed for the conductivity, $\sigma$.

Before process 600 executes, an array permutation index is assigned, in a permutation table, to each combination of transmit antenna array plate positions and receive antenna array plate positions to be used; a frequency index is assigned, in a frequency table, to each of a set of microwave frequencies to be used; and a transmit antenna number is assigned, in a transmit antenna table, to each transmit antenna to be used.

Step 610 of process 600 initializes the array permutation index. Step 615 positions the antenna array plates based on the array permutation index. Step 620 initializes a frequency index. Step 625 selects a transmit frequency based on the frequency index. Step 630 initializes a transmit antenna index. Step 635 selects a transmit antenna based on the transmit antenna index. Step 640 transmits the selected frequency from the selected transmit antenna. Step 645 receives scattered microwave data at each receive antenna and stores the microwave data. Step 650 determines whether scattered microwave data has been stored for each transmit antenna in the transmit antenna table; if not, step 655 increments the transmit antenna index and the method passes back to step 635. When data has been stored for each transmit antenna in the transmit antenna table, step 660 determines whether scattered microwave data has been stored for each frequency in the frequency table; if not, step 665 increments the frequency index and the method passes back to step 625. Step 670 determines whether data has been stored for each combination of transmit antenna array plate positions and receive antenna array plate positions in the permutation table. If so, process 600 terminates; otherwise step 675 increments the array permutation index and the method continues with step 615. Thus, process 600 loops over all combinations of the array permutation index (e.g., over all combinations of antenna positions defined in the permutation table), the frequency index and the transmit antenna index, until scattered microwave data has been acquired and stored for each combination of these indices.

An exemplary multiple frequency dispersion reconstruction ("MFDR") algorithm will now be derived. Assuming time dependence of exp(jωt), the complex wave number squared, $k^2$, for non-magnetic isotropic media can be written as $$k^2 = \omega^2 \mu_0 \varepsilon(\omega) \quad \text{(Eq. 6)}$$
$$= \omega^2 \mu_0 \left( \varepsilon_r(\omega)\varepsilon_0 - j\frac{\sigma(\omega)}{\omega} \right)$$
$$= k_R^2 - jk_I^2$$

where ω is the angular frequency, and $k_R^2 = \omega^2\mu_0\epsilon_0\epsilon_r(\omega))$ and $k_I^2 = \omega\mu_0\sigma(\omega w)$ are the real and imaginary constituents of $k^2$. One microwave frequency range of interest lies within the range between the dipolar and atomic relaxation frequencies, such that dielectric property variations with frequency are smooth and well-behaviored. Without loss of generality, we can express the dispersion relationships in terms of non-dispersive coefficients as $$\epsilon_r(\omega) = \epsilon_r(\omega, \lambda_1, \lambda_2, \ldots, \lambda_m) \quad \text{(Eq. 7a)}$$

$$\sigma(\omega) = \sigma(\omega, \gamma_1, \gamma_2, \ldots, \gamma_n) \quad \text{(Eq. 7b)}$$

where $\lambda_i$ (i=1, 2, ... M) and $\gamma_i$ (i=1, 2, ... N) are frequency independent dispersion coefficients for the M and N term relationships $\epsilon_r(\omega)$ and $\sigma(\omega)$, respectively.

The Gauss-Newton method assumes (from a truncated Taylor series with respect to $k_R^2$ and $k_I^2$):

$$\Delta E_R = \frac{\partial E_R}{\partial k_R^2}\Delta k_R^2 + \frac{\partial E_R}{\partial k_I^2}\Delta k_I^2 \qquad (Eq.\ 8)$$

$$\Delta E_I = \frac{\partial E_I}{\partial k_R^2}\Delta k_R^2 + \frac{\partial E_I}{\partial k_I^2}\Delta k_I^2 \qquad (Eq.\ 9)$$

where vectors $\Delta E_R$ and $\Delta E_I$ are real and imaginary parts of a difference between measured and calculated fields, respectively. The lengths of vectors $\Delta E_R$ and $\Delta E_I$ are equal to measured data TR=T×R, where T denotes a number of transmitters used in data gathering, and R denotes a number of receivers per transmitter. Vectors $k_R^2$ and $k_I^2$ are of length P, which is a number of unknown property parameters. The derivative terms in Eq. are therefore matrices of size TR×P.

Combining Eq. 6 through Eq. 9, applying the chain rule and assuming single frequency operation initially yields:

$$\Delta E_R = \sum_{i=1}^{M} \frac{\partial E_R}{\partial k_R^2}\frac{\partial k_R^2}{\partial \lambda_i}\Delta\lambda_i + \sum_{i=1}^{N} \frac{\partial E_R}{\partial k_I^2}\frac{\partial k_I^2}{\partial \gamma_i}\Delta\gamma_i \qquad (Eq.\ 10)$$

$$\Delta E_I = \sum_{i=1}^{M} \frac{\partial E_I}{\partial k_R^2}\frac{\partial k_R^2}{\partial \lambda_i}\Delta\lambda_i + \sum_{i=1}^{N} \frac{\partial E_I}{\partial k_I^2}\frac{\partial k_I^2}{\partial \gamma_i}\Delta\gamma_i \qquad (Eq.\ 11)$$

which can be rewritten in matrix form as:

$$\begin{pmatrix} J_R^R & J_I^R \\ J_R^I & J_I^I \end{pmatrix}\begin{pmatrix} \Delta l \\ \Delta g \end{pmatrix} = \begin{pmatrix} \Delta E_R \\ \Delta E_I \end{pmatrix} \qquad (Eq.\ 12)$$

The components of a Jacobian matrix J are:

$$J_R^R = \left(\frac{\partial E_R}{\partial k_R^2}\frac{\partial k_R^2}{\partial \lambda_1} \,\bigg|\, \frac{\partial E_R}{\partial k_R^2}\frac{\partial k_R^2}{\partial \lambda_2} \,\bigg|\, \cdots \,\bigg|\, \frac{\partial E_R}{\partial k_R^2}\frac{\partial k_R^2}{\partial \lambda_M}\right) \qquad (Eq.\ 13)$$

$$J_I^R = \left(\frac{\partial E_R}{\partial k_I^2}\frac{\partial k_I^2}{\partial \gamma_1} \,\bigg|\, \frac{\partial E_R}{\partial k_I^2}\frac{\partial k_I^2}{\partial \gamma_2} \,\bigg|\, \cdots \,\bigg|\, \frac{\partial E_R}{\partial k_I^2}\frac{\partial k_I^2}{\partial \gamma_N}\right) \qquad (Eq.\ 14)$$

with $J_R^I$ and $J_I^I$ having corresponding definitions. $J_R^R$ and $J_R^I$ are submatrices with dimensions (TR)×(P×M) whereas $J_I^R$ and $J_I^I$ have dimensions (TR)×(P×N). $\Delta l = (\Delta\lambda_1, \Delta\lambda_2, \ldots, \Delta\lambda_M)^T$ and $\Delta g = (\Delta\gamma_1, \Delta\gamma_2, \ldots, \Delta\gamma_N)^T$ are frequency independent updates that are solved for at each iteration. By solving Eq. 12 at each iteration, dispersion coefficient lists $(\lambda_1, \lambda_2, \ldots, \lambda_M)$ and $(\gamma_1, \gamma_2, \ldots, \gamma_N)$ can be updated by $$(\lambda_1, \lambda_2, \ldots, \lambda_M)_{s+1} = (\lambda_1, \lambda_2, \ldots, \lambda_M)_s + \Delta l_s^T \qquad (Eq.\ 15)$$

$$(\gamma_1, \gamma_2, \ldots, \gamma_N)_{s+1} = (\gamma_1, \gamma_2, \ldots, \gamma_N)_s + \Delta g_s^T \qquad (Eq.\ 16)$$

where s is an iteration index.

Images may be formed by assigning a gray scale to any of the dispersion coefficient distributions. As before, dielectric profiles at any specified frequency in a frequency range being investigated can be readily calculated from Eq. 7a and Eq. 7b. Additionally, reconstructed dispersion coefficients themselves (e.g., any of $(\lambda_1, \lambda_2, \ldots, \lambda_M)$ or $(\gamma_1, \gamma_2, \ldots, \gamma_N)$) may be used for imaging, and may provide diagnostic information by capturing a dispersion "signature" of the target over a range of frequencies.

For a given dispersion relationship, the terms $$\frac{\partial k^2}{\partial \lambda_i} \text{ and } \frac{\partial k^2}{\partial \gamma_i}$$

Eq. 10 and Eq. 11 can be computed analytically $$\frac{\partial E^2}{\partial k^2}$$

can be derived as discussed in Fang et al., "Microwave Image Reconstruction of Tissue Property Dispersion Characteristics Utilizing Multiple-Frequency Information," *IEEE Trans. Microwave Techniques and Technology*, 52:1866-1875, August 2004, which is incorporated herein by reference.

Since $\Delta l$ and $\Delta g$ are frequency independent, Eq. 12 can be generalized to F frequencies by expanding the Jacobian matrix on the left and electric field difference vector on the right:

$$\begin{pmatrix} J_R^R(\omega_1) & J_I^R(\omega_1) \\ J_R^I(\omega_1) & J_I^I(\omega_1) \\ J_R^R(\omega_2) & J_I^R(\omega_2) \\ J_R^I(\omega_2) & J_I^I(\omega_2) \\ \cdots & \cdots \\ J_R^R(\omega_F) & J_I^R(\omega_F) \\ J_R^I(\omega_F) & J_I^I(\omega_F) \end{pmatrix} \begin{pmatrix} \Delta l \\ \Delta g \end{pmatrix} = \begin{pmatrix} \Delta E_R(\omega_1) \\ \Delta E_I(\omega_1) \\ \Delta E_R(\omega_2) \\ \Delta E_I(\omega_2) \\ \cdots \\ \Delta E_R(\omega_F) \\ \Delta E_I(\omega_F) \end{pmatrix} \qquad (Eq.\ 17)$$

In Eq. 17, it can now be seen that the Jacobian matrix and $\Delta E$ terms are functions of frequency. Eq. 17 is a general form for MFDR and is valid for both 2D and 3D cases, since the dispersion characteristics for an isotropic medium are dimensionless. It is also valid for modeling dispersive or non-dispersive media in vector or scalar forward models.

Eq. 17 can also be combined without loss of generality with a log-magnitude phase form ("LMPF") approach as discussed in Paulsen et al., "Microwave Image Reconstruction utilizing log-magnitude and unwrapped phase to improve high-contrast object recovery," *IEEE Transactions on Medical Imaging*, 20:104-106, 2001, which is incorporated herein by reference. An LMPF expression for Eq. 17 is:

$$\begin{pmatrix} J_R^\Gamma(\omega_1) & J_I^\Gamma(\omega_1) \\ J_R^\Phi(\omega_1) & J_I^\Phi(\omega_1) \\ J_R^\Gamma(\omega_2) & J_I^\Gamma(\omega_2) \\ J_R^\Phi(\omega_2) & J_I^\Phi(\omega_2) \\ \cdots & \cdots \\ J_R^\Gamma(\omega_F) & J_I^\Gamma(\omega_F) \\ J_R^\Phi(\omega_F) & J_I^\Phi(\omega_F) \end{pmatrix} \begin{pmatrix} \Delta l \\ \Delta g \end{pmatrix} = \begin{pmatrix} \Delta\Gamma(E(\omega_1)) \\ \Delta\Phi(E(\omega_1)) \\ \Delta\Gamma(E(\omega_2)) \\ \Delta\Phi(E(\omega_2)) \\ \cdots \\ \Delta\Gamma(E(\omega_F)) \\ \Delta\Phi(E(\omega_F)) \end{pmatrix} \qquad (Eq.\ 18)$$

where $\Gamma$ and $\Phi$ symbolize the log-magnitude and unwrapped phase of electric fields, respectively. Accordingly, modified Jacobian terms can be expressed as:

$$J_R^\Gamma = \frac{E_R J_R^R + E_I J_R^I}{E_R^2 + E_I^2} \quad \text{(Eq. 19)}$$

$$J_I^\Gamma = \frac{E_R J_R^I + E_I J_R^I}{E_R^2 + E_I^2} \quad \text{(Eq. 20)}$$

$$J_R^\Phi = \frac{E_R J_I^I + E_I J_R^R}{E_R^2 + E_I^2} \quad \text{(Eq. 21)}$$

$$J_I^\Phi = \frac{E_R J_I^I + E_I J_I^R}{E_R^2 + E_I^2} \quad \text{(Eq. 22)}$$

where $J^\Gamma$ and $J^\Phi$ are Jacobian submatrices, $\Delta\Gamma(E(\omega))$, where $\Delta\Gamma(E(\omega))=\ln(E^{meas}(\omega))-\ln(E^{calc}(\omega))$ are the differences in log-amplitude between measured and calculated field values at receiver antennas, and $\Delta\Phi(E(\omega))$, where $\Delta\Phi(E(\omega))=\arg(E^{meas}(\omega))-\arg(E^{calc}(\omega))$, are the differences between measured and calculated unwrapped phases.

Figure 14:
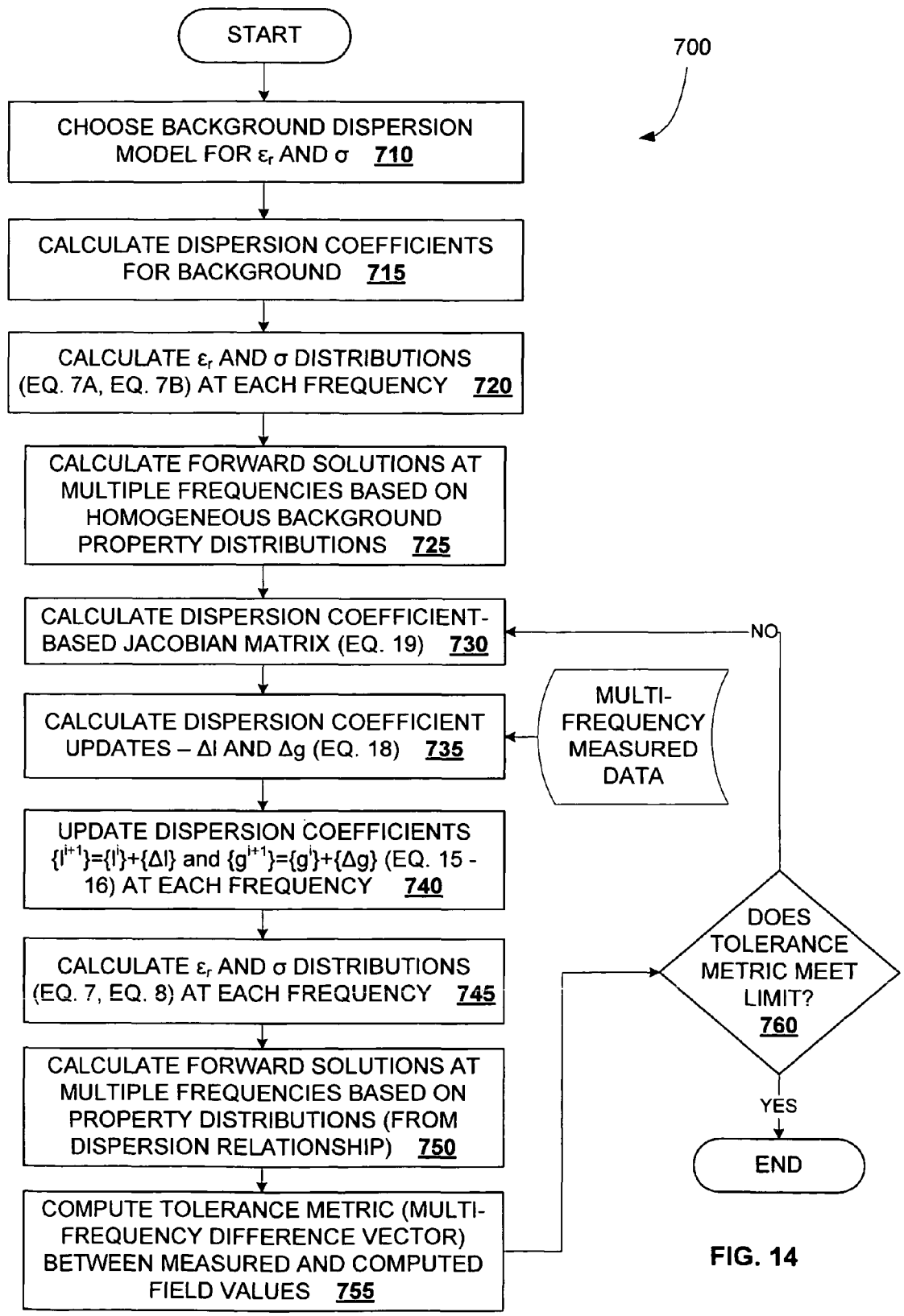
FIG. 14 is a flowchart illustrating exemplary steps of one microwave imaging process.

FIG. 14 is a flowchart illustrating exemplary steps of a microwave imaging process 700. Process 700 is for example implemented by microwave imaging system 10, with processor 36 executing software 35 (see FIG. 1). Process 700 processes scattered microwave data (e.g., data that is generated and stored by process 600) to reconstruct images of a target. An optional step 710 chooses a background dispersion model for $\epsilon_r$ and $\sigma$ from one of the forms shown in Eq. 1 through Eq. 5. In certain embodiments, dispersion models for $\epsilon_r$ and $\sigma$ will be preselected, or may be chosen by a human upon presentation of a set of choices by system 10. Step 715 calculates dispersion coefficients for background. Step 720 calculates homogeneous background $\epsilon_r$ and $\sigma$ distributions at each frequency based on the dispersion coefficients calculated in step 715 (e.g., each frequency in the frequency table of FIG. 1), using Eq. 7a and Eq. 7b. Step 725 calculates forward solutions at multiple frequencies based on homogeneous background property distributions. Step 730 calculates a dispersion coefficient based Jacobian matrix, using Eq. 19-Eq. 22. Step 735 uses the multi-frequency data (e.g., the data gathered by process 600) to calculate dispersion coefficient updates $\Delta l$ and $\Delta g$ using Eq. 18. Step 740 updates dispersion coefficients $\Delta l$ and $\Delta g$ using Eq. 15 and 16. Step 745 calculates $\epsilon_r$ and $\sigma$ distributions at each frequency using Eq. 7a and Eq. 7b, in the same manner as step 720. Step 750 calculates forward solutions at multiple frequencies based on property distributions, in the same manner as step 725. Step 755 computes a tolerance metric that may be, for example, a multi-frequency difference vector between measured and computed field values. Step 760 determines whether the tolerance metric meets a pre-defined limit. For example, an L2 norm of a multi-frequency difference vector (an L2 norm of a vector is defined as the square root of the sum of the squares of the terms in the vector) may be compared to the limit. Other calculations than the L2 norm based on the multi-frequency difference vector may be used to determine whether the limit is met. If the tolerance metric meets the pre-determined limit, process 700 ends, otherwise process 700 passes back to step 730.

Time required for calculation of a Jacobian matrix may be significantly reduced by utilizing a technique described herebelow and called a "nodal adjoint method" herein. An adjoint formula of the Jacobian matrix can be rewritten in terms of a summation over forward elements as $$J((s,r),\tau) = \sum_{e\in\Omega_\tau}(D_\tau^e E_s^e)^T E_r^e \quad \text{(Eq. 23)}$$

where $\Omega_\tau$ denotes a region within which $\phi_\tau \neq 0$, $\Sigma_{e\in\Omega_\tau}$ denotes a summation over forward elements which are located within $\Omega_\tau$, and the superscript T is standard notation for the transpose of a matrix. A weighting matrix $D_\tau^e$ is a square matrix with each element defined by $$d_{i_e,l_e}^\tau = \int_{\Omega_e}\phi_{i_e}(\vec{r})\phi_{l_e}(\vec{r})\varphi_\tau(\vec{r})d\vec{r} \quad \text{(Eq. 24)}$$

where $i_e=1,2,\ldots M$ and $l_e=1,2,\ldots M$ are local node indices, and M is the total node number for a single forward element (M=3 in 2D, and M=4 in 3D). $\phi$ and $\varphi$ represent the basis functions over the forward and parameter meshes, respectively. $\Omega_e$ is a spatial domain occupied by an e-th forward element. $E_s^e=\{E_s(P_\kappa^e)\}_{\kappa=1}^M$ and $E_r^e=\{E_r(P_\kappa^e)\}_{\kappa=1}^M$ are the fields at vertices $(P_\kappa^e)_{\kappa=1}^M$ of the element due to source antennas at s and r, respectively. Eq. 23 is referred to as the element-based form of the adjoint formula.

In certain cases, boundaries of forward elements may not precisely match those of parameter elements. FIG. 15 illustrates such a case. In FIG. 15, a forward mesh 280 including a $\tau$-th coarse node 285 is shown in solid lines, while a parameter mesh 290 is shown in dashed lines. Evaluation of Eq. 23 becomes much more difficult in a case like that shown in FIG. 15, since integrations may have to be evaluated over partial elements of the forward mesh. The nodal adjoint method simplifies the integration for a given dual mesh pair by assuming that an averaged size of forward elements is significantly smaller than that of parameter elements. Derivation of an expression for this method follows.

Within domain $\Omega_e$ where $e\in\Omega_\tau$, parameter basis function $\phi_\tau$ can be expanded as a linear combination of forward basis functions:

$$\varphi_\tau(\vec{r}) = \sum_{\kappa=1}^M \varphi_\tau(\vec{p}_\kappa)\phi_\kappa(\vec{r}) \quad \text{(Eq. 25)}$$

Inserting Eq. 25 into Eq. 23, we get:

$$J((s,r),\tau) = \sum_{e\in\Omega_\tau}\sum_{\kappa=1}^M \varphi_\kappa(\vec{p}_\kappa)(D_{\tau\kappa}^e E_s^e)^T E_r^e \quad \text{(Eq. 26)}$$

where $D_{\tau\kappa}^e$ is an M×M matrix defined as $$D_{\tau\kappa}^e = \begin{pmatrix} \langle\phi_1\phi_1\phi_\kappa\rangle & \langle\phi_1\phi_2\phi_\kappa\rangle & \cdots & \langle\phi_1\phi_M\phi_\kappa\rangle \\ \langle\phi_2\phi_1\phi_\kappa\rangle & \langle\phi_2\phi_2\phi_\kappa\rangle & \cdots & \langle\phi_2\phi_M\phi_\kappa\rangle \\ \vdots & \vdots & \ddots & \vdots \\ \langle\phi_M\phi_1\phi_\kappa\rangle & \langle\phi_M\phi_2\phi_\kappa\rangle & \cdots & \langle\phi_M\phi_M\phi_\kappa\rangle \end{pmatrix} \quad \text{(Eq. 27)}$$

where $\langle\rangle$ denotes volume integration over $\Omega_e$. Nonzero off-diagonal elements in Eq. 27 result in cross-multiplication terms of fields at different nodes in Eq. 26.

To simplify the analysis, we approximate weighting matrix $D_{\tau\kappa}^e$ by summing each column (or row), adding off-diagonal elements to diagonal elements, and simultaneously zeroing out all off-diagonal terms:

$$\tilde{D}_{\tau\kappa}^e = \begin{pmatrix} \sum_{i=1}^{M} \langle \phi_i \phi_1 \phi_\kappa \rangle & 0 & \cdots & 0 \\ 0 & \sum_{i=1}^{M} \langle \phi_i \phi_2 \phi_\kappa \rangle & \cdots & 0 \\ \vdots & \vdots & \ddots & \vdots \\ 0 & 0 & \cdots & \sum_{i=1}^{M} \langle \phi_i \phi_M \phi_\kappa \rangle \end{pmatrix} \quad \text{(Eq. 28)}$$

It can be proved (see, e.g., pages 187 and 188 of Appendix A of U.S. Provisional Patent Application 60/638,005) that $$\sum_{\kappa=1}^{M} \tilde{D}_{\tau\kappa}^e = \frac{V_e}{M} I \quad \text{(Eq. 29)}$$

where $V_e$ is a volume of an e-th forward element in a 3D case (or an area of an e-th forward element in a 2D case) and I is an M×M identity matrix. By substituting Eq. 29 back into Eq. 26 and expanding vector multiplications, the reorganized equation can be written as $$J((s,r),\tau) = \sum_{n \in \Omega_\tau} \left( \frac{\sum_{e \in \Omega_n} V_e}{M} \right) \varphi_\kappa(\vec{p}_n) E_s(\vec{p}_n) E_r(\vec{p}_n) \quad \text{(Eq. 30)}$$

where $\Sigma_{n \in \Omega_\tau}$ refers to a summation over forward nodes which fall inside $\Omega_\tau$, and $\Sigma_{e \in \Omega_n}$ refers to the summation over forward elements that share an n-th forward node. $\phi_\kappa(P_n)$ is the value of parameter mesh basis function at the set of forward nodes $P_n$ within $\Omega$ (the area or volume where the basis function is not zero). The term $$\frac{\sum_{e \in \Omega_n} V_e}{M}$$

is a scalar term associated with the n-th forward node; this term can be simplified as $V_n$, which can be calculated either in a pre-processing operation or on-the-fly, so that Eq. 30 may be rewritten as:

$$J((s,r),\tau) = \sum_{n \in \Omega_\tau} V_n \varphi_\kappa(\vec{p}_n) E_s(\vec{p}_n) E_r(\vec{p}_n) \quad \text{(Eq. 31)}$$

Eq. 30 and/or Eq. 31, called "nodal adjoint formulas" herein, allow simplified computation of a Jacobian matrix for conformal and nonconformal dual-meshes. $E_s(P_n)$ and $E_r(P_n)$ are nodal electrical field values computed directly from the forward problem. $V_n$ and $\phi_\tau(P_n)$ require only simple algebraic operations, so they can be built "on-the-fly," that is, they can be calculated on a point-by-point basis during matrix calculation. Calculation on-the-fly is advantageous when calculations utilize forward techniques that might generate meshes dynamically, such as in Finite Difference Time Domain ("FDTD") and certain adaptive methods. A reconfiguration of matrix $D_{\tau\kappa}^e$ may be valid when the forward element is substantially small with respect to the parameter mesh elements, so that the field values at its vertices are approximately equal.

The above derivation of Eq. 30 was validated by computing Jacobian matrices utilizing Eq. 30 over a series of refined dual meshes, utilizing a 40 by 40 node fine mesh grid. FIG. 16 shows plots of a segment of an original parameter mesh 292 superimposed on a refined forward mesh 294 (lines of mesh 292 hide certain lines of mesh 294). FIG. 17 shows a plot 296 of maximum relative error between a nodal adjoint calculation, using Eq. 30, and an adjoint calculation of the Jacobian matrix. Plot 296 shows that when the forward mesh size is small compared with the parameter mesh, the nodal adjoint calculation provides a good approximation to the adjoint calculation.

Figure 18:
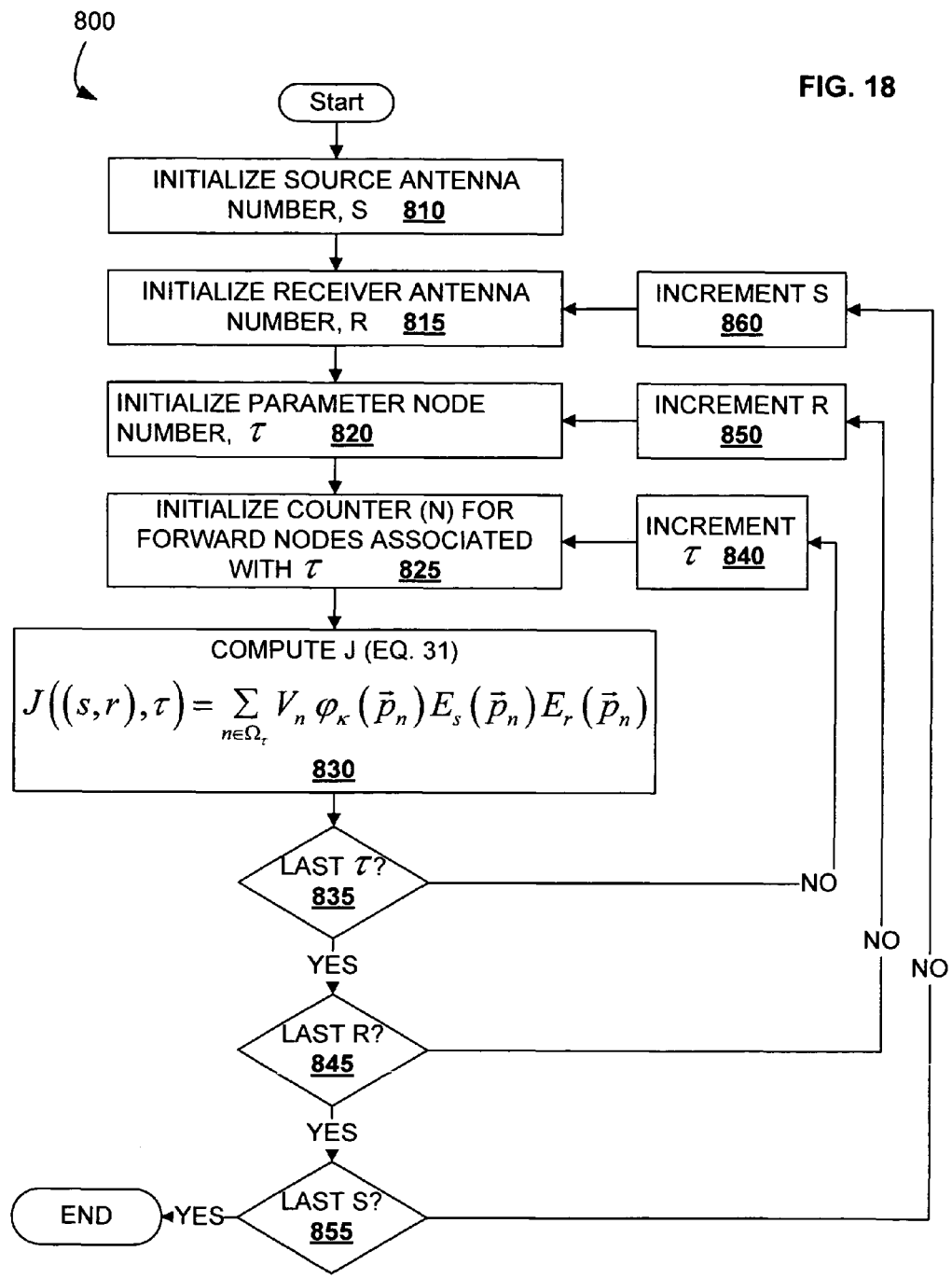
FIG. 18 is a flowchart illustrating exemplary steps of one microwave imaging process.

FIG. 18 is a flowchart illustrating exemplary steps of a microwave imaging process 800. Process 800 is for example implemented by microwave imaging system 10, with processor 36 executing software 35 (see FIG. 1). Process 800 utilizes a nodal adjoint method to construct a Jacobian matrix, and may execute more quickly than an otherwise equivalent method that explicitly calculates the Jacobian matrix utilizing an adjoint method (e.g., Eq. 23). Steps 810, 815, 820 and 825 initialize a source antenna number s, a receiver antenna number r, a parameter node number τ and a forward node number n respectively. Step 830 utilizes Eq. 31 to calculate each element J((s, r), τ) across all n forward nodes associated with each parameter node τ. Step 835 checks to see whether all τ nodes associated with a source and receiver combination (s, r) have been processed. If not, step 840 increments τ, and process 800 returns to step 825. If so, process 800 goes on to step 845. Step 845 checks to see whether data for all receiver antennas associated with a source antenna s has been processed. If not, step 850 increments r, and process 800 returns to step 820. Step 855 checks to see whether data for all source antennas has been processed. If not, step 860 increments s, and process 800 returns to step 815. If so, process 800 ends.

Table 1 shows how embodiments of 2D and 3D reconstruction processes may be classified depending on whether 2D or 3D reconstruction is implemented (e.g., values are computed for a 2D or 3D parameter mesh, respectively), whether a forward mesh is represented as a 2D or as a 3D mesh, and whether fields are represented as scalar or vector values.

TABLE 1

| | Forward mesh: | | | |
|---|---|---|---|---|
| | 2D | | 3D | |
| Field representation: | Scalar | Vector (TM) | Scalar | Vector |
| 2D parameter mesh | 2Ds/2D | 2Ds-FDTD/2D | 3Ds/2D | |
| 3D parameter mesh | | | 3Ds/3D | 3Dv/3D |

Figure 20A:
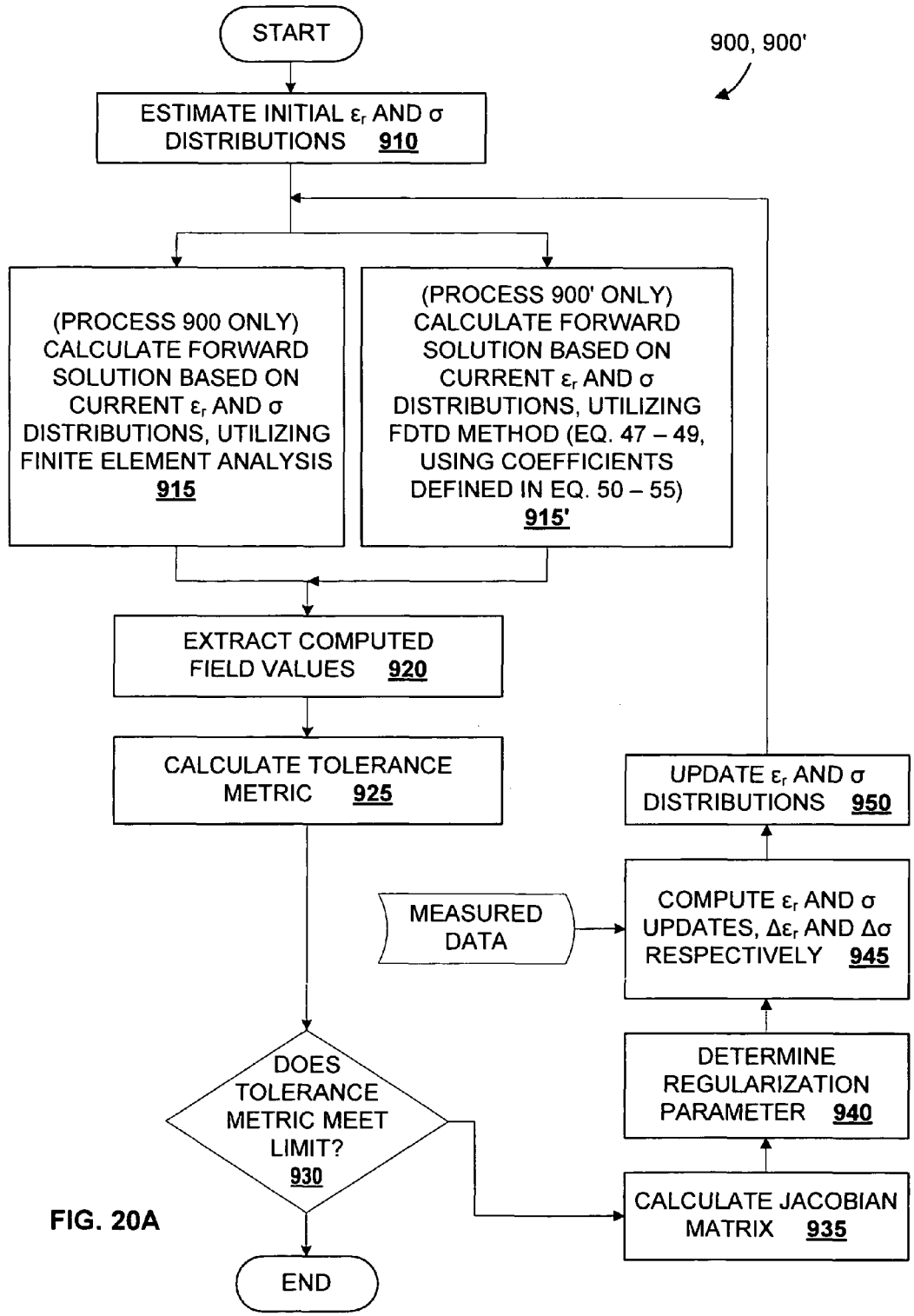
FIG. 20A is a flowchart illustrating a microwave imaging process that utilizes finite element analysis to perform a forward field calculation, and a microwave imaging process that utilizes a 2Ds-FDTD/2D forward field calculation, in accord with an embodiment.

For example, as classified in Table 1, a "2Ds/2D" process represents fields as scalar values, utilizes a 2D forward mesh, and performs a 2D reconstruction that iteratively computes forward solutions of a 2D forward mesh based on dielectric properties at each iteration of the reconstruction utilizing a finite element technique (see process 900, FIG. 20A). A "2Ds-FDTD/2D" process is similar in that it also represents electric fields as scalar values and performs an iterative 2D reconstruction; however, the 2Ds-FDTD/2D process utilizes a Finite Difference Time Domain ("FDTD") approach for the forward calculation (see process 900', FIG. 20A). A "3Ds/2D" process represents fields as scalar values, and utilizes a 3D forward mesh, but performs a 2D reconstruction (see process 1100, FIG. 24). A "3Ds/3D" process represents fields as scalar values, utilizes a 3D forward mesh, and performs a 3D reconstruction. A "3Dv/3D" process represents fields as vector values, and utilizes a 3D forward mesh, but performs a 3D reconstruction (see process 1200, FIG. 26).

FIG. 19A-19D illustrate layouts of an array of antennas in an illumination tank, a forward mesh and a parameter mesh for each of several microwave imaging processes, in accord with embodiments.

Figure 19A:
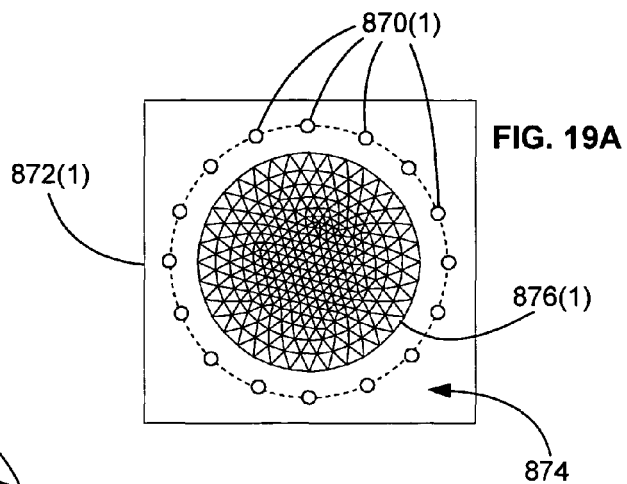
FIG. 19A-19D illustrate layouts of an array of antennas in an illumination tank, a forward mesh and a parameter mesh for each of several microwave imaging processes, in accord with embodiments.

FIG. 19A shows an array of antennas 870(1) (e.g., any of antennas 30, 31, 102, 102', 202, 202', 302, 402 or 403) in an illumination tank 872(1) (e.g., any of illumination tanks 32, 104, 204, 304 or 404). Area within illumination tank 872(1) is modeled as a forward mesh 874, and an area to be imaged is modeled as a parameter mesh 876(1), in 2Ds/2D reconstruction process 900 or 2Ds-FDTD/2D reconstruction process 900', as described below. Only a few of antennas 870(1) are labeled, and mesh lines of forward mesh 874 are not shown, for clarity of illustration in FIG. 19A.

Figure 19B:
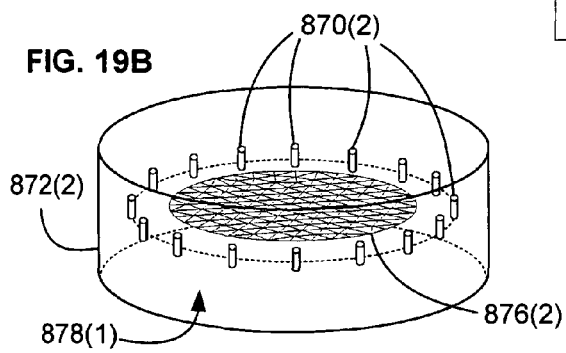

FIG. 19B shows an array of antennas 870(2) (e.g., any of antennas 30, 31, 102, 102', 202, 202', 302, 402 or 403) in an illumination tank 872(2) (e.g., any of illumination tanks 32, 104, 204, 304 or 404). Volume within illumination tank 872(2) is modeled as a forward mesh 878(1), and an area to be imaged is modeled as a parameter mesh 876(2), in a 3Ds/2D reconstruction process 1100 (see FIG. 24), as described below. Only a few of antennas 870(2) are labeled, and mesh lines of forward mesh 878(1) are not shown, for clarity of illustration in FIG. 19B.

Figure 19C:
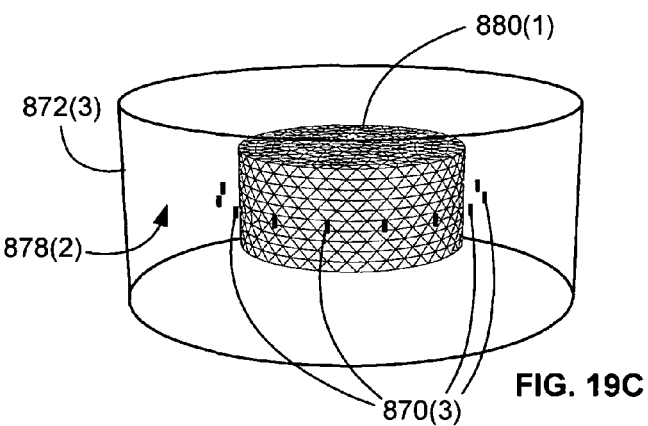

FIG. 19C shows an array of antennas 870(3) (e.g., any of antennas 30, 31, 102, 102', 202, 202', 302, 402 or 403) in an illumination tank 872(3) (e.g., any of illumination tanks 32, 104, 204, 304 or 404). Volume within illumination tank 872(3) is modeled as a forward mesh 878(2), and a volume to be imaged is modeled as a parameter mesh 880(1), in a 3Ds/3D reconstruction process. Only a few of antennas 870(3) are labeled, and mesh lines of forward mesh 878(2) are not shown, for clarity of illustration in FIG. 19C.

Figure 19D:
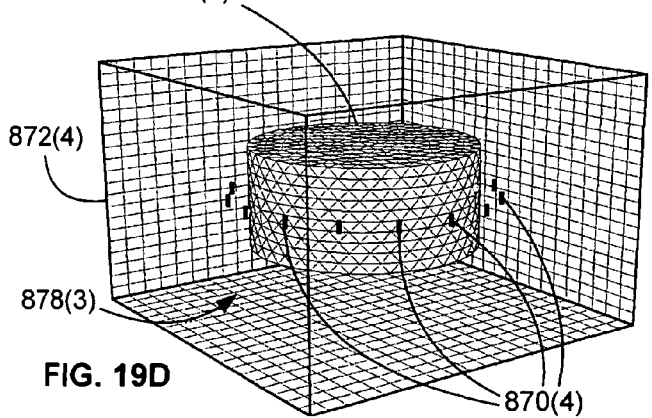

FIG. 19D shows an array of antennas 870(4) (e.g., any of antennas 30, 31, 102, 102', 202, 202', 302, 402 or 403) in an illumination tank 872(4) (e.g., any of illumination tanks 32, 104, 204, 304 or 404). Volume within illumination tank 872(4) is modeled as a forward mesh 878(3), and a volume to be imaged is modeled as a parameter mesh 880(2), in 3Dv/3D reconstruction process 1200 (see FIG. 26), as described below. Only a few of antennas 870(4) are labeled, and mesh lines of forward mesh 878(3) are not shown, for clarity of illustration in FIG. 19D.

The 2Ds/2D process formulates forward field distributions as a 2D problem, that is, it assumes that for a plane being imaged, if Cartesian coordinates x, y define coordinates within the plane and z defines an axis perpendicular to the plane, then (1) a scattering dielectric profile to be imaged is a 2D distribution with no variation in the z direction, or, $$\frac{dk^2(\vec{r})}{dz} = 0;$$

(2) sources (antennas) are line sources that are infinitely long in the z axis; and therefore, (3) a propagating wave is a transverse magnetic (TM) wave where the E vector is parallel to the z axis, i.e., $E_x(\vec{r}) = E_y(\vec{r}) = 0$. Measurement data including electric field values are generated (e.g., utilizing system 10), and permittivity and conductivity values are generated that form solutions that are consistent with the curl relationships of Maxwell's equations, i.e., $$\nabla \times \vec{E}(\vec{r}, t) = -\frac{\partial \vec{B}(\vec{r}, t)}{\partial t} - \vec{M}(\vec{r}, t) \qquad \text{(Eq. 32)}$$

$$\nabla \times \vec{H}(\vec{r}, t) = -\frac{\partial \vec{D}(\vec{r}, t)}{\partial t} + \vec{J}_i(\vec{r}, t) + \vec{J}(\vec{r}, t) \qquad \text{(Eq. 33)}$$

where $\vec{E}, \vec{H}, \vec{D}, \vec{B}, \vec{J}_i, \vec{J}$, and $\vec{M}$ are electric field, magnetic field, electric flux, magnetic flux, induced current density, source current density and magnetic current density, respectively (it is appreciated that magnetic current density is a fictitious term introduced for mathematical symmetry). For a target to be imaged (e.g., target 34) that are (1) isotropic, (2) nonmagnetic, (3) electrically lossy and (4) stationary, Eq. 32 and Eq. 33 can be written as $$\nabla \times \vec{E}(\vec{r}, t) = -\mu_0 \frac{\partial \vec{H}(\vec{r}, t)}{\partial t} \qquad \text{(Eq. 34)}$$

$$\nabla \times \vec{H}(\vec{r}, t) = \varepsilon(\vec{r}) \frac{\partial \vec{E}(\vec{r}, t)}{\partial t} + \sigma(\vec{r}) \vec{E}(\vec{r}, t) + \vec{J}(\vec{r}, t) \qquad \text{(Eq. 35)}$$

Assuming further that the fields are time-harmonic, that is, characterized by a frequency ω, and utilizing complex notation to simplify the notation, it can be shown that $$\nabla \times \nabla \times \vec{E}(\vec{r}) - \omega^2 \mu_0 \left( \varepsilon(\vec{r}) - j\frac{\sigma(\vec{r})}{\omega} \right) \vec{E}(\vec{r}) = -j\omega\mu_0 \vec{J}(\vec{r}) \qquad \text{(Eq. 36)}$$

If a squared complex wave number is defined as $$k^2(\vec{r}) = \omega^2 \mu_0 \left( \varepsilon(\vec{r}) - j\frac{\sigma(\vec{r})}{\omega} \right) \qquad \text{(Eq. 37)}$$

then by applying Gauss' law and charge conservation laws, it can be shown that $$\nabla^2 \vec{E}(\vec{r}) + k^2(\vec{r}) \vec{E}(\vec{r}) + \nabla \left( \frac{\vec{E}(\vec{r}) \cdot \nabla k^2(\vec{r})}{k^2(\vec{r})} \right) = -j\omega\mu_0 \vec{J}(\vec{r}). \qquad \text{(Eq. 38)}$$

Eq. 36 and Eq. 38 are vector form wave equations that define the relationship between a frequency domain electric field and dielectric properties (included in $k^2(\vec{r})$). In other words, Eq. 36 and Eq. 38 define the forward model for microwave imaging. $k^2(\vec{r})$ stores unknown permittivity and conductivity distributions in its real and imaginary parts, respectively. When $k^2(\vec{r})$ is reconstructed, the permittivity and conductivity distributions are obtained.

FIG. 20A is a flowchart illustrating a microwave imaging process 900 that utilizes finite element analysis to perform a forward field calculation, and a microwave imaging process 900' that utilizes a 2Ds-FDTD/2D forward field calculation process 915'. Processes 900 and 900' are for example implemented by microwave imaging system 10, with processor 36 executing software 35 (see FIG. 1). 2Ds-FDTD/2D reconstruction process 900' may be advantageous in that 2Ds-FDTD/2D forward field calculation process 915' updates the forward solution at each iteration, instead of utilizing a forward solution that remains static as dielectric properties iterate. In both processes 900 and 900', step 910 estimates initial $\epsilon_r$ and $\sigma$ distributions. In process 900, step 915 calculates forward solutions based on homogeneous background property distributions, while in process 900', step 915' calculates forward solutions based on current $\epsilon_r$ and $\sigma$ distributions utilizing an FDTD method (see FIG. 20B). In both processes 900 and 900', step 920 extracts computed field values. Step 925 calculates a tolerance metric. Step 930 determines whether the tolerance metric meets a predetermined limit. If not, step 935 calculates a Jacobian matrix, and step 940 determines a regularization parameter. Regularization adds terms to the main diagonal of a Hessian matrix (where the Hessian matrix H relates to the Jacobian matrix J as $H=J^T J$) to make it more diagonally dominant, so that it can be factored, to facilitate solving for property updates. The regularization parameter may be determined empirically, for example, in a combination of Marquardt and/or Tikhonov regularization schemes. Step 945 computes $\epsilon_r$ and $\sigma$ updates, $\Delta\epsilon_r$ and $\Delta\sigma$ respectively, utilizing measurement data, and step 950 updates the $\epsilon_r$ and $\sigma$ distributions as $\epsilon_r^{i+1}=\epsilon_r^i+\Delta\epsilon_r$ and $\sigma^{i+1}=\sigma^i+\Delta\sigma$, where i is an iteration index, returning to step 915 or 915' as applicable. If step 930 determines that the tolerance metric meets the predetermined limit, processes 900 and 900' end.

Figure 20B:
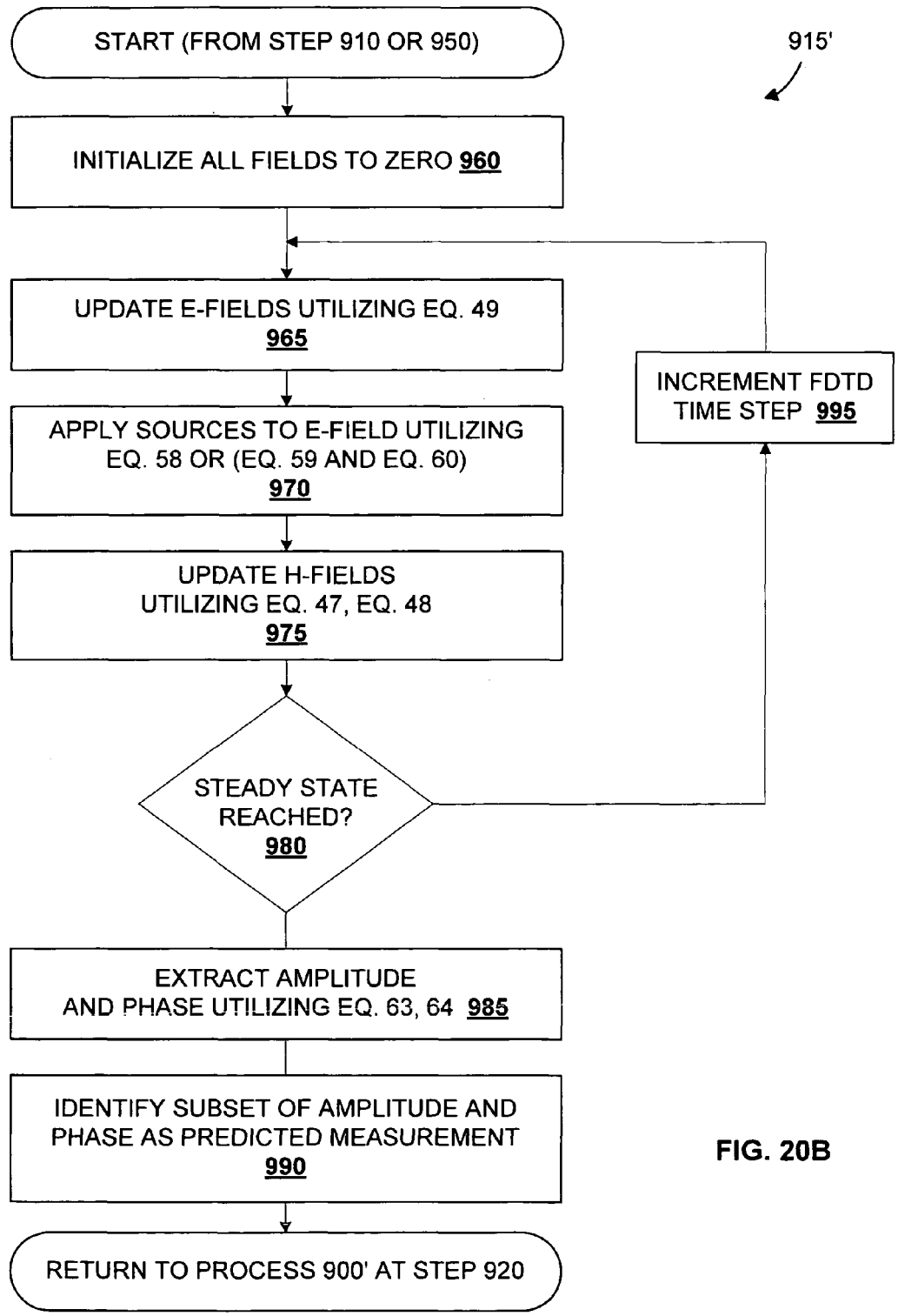
FIG. 20B shows intermediate steps of one process step shown in FIG. 20A.

2Ds-FDTD/2D process 900' may utilize the same assumptions as those used in 2Ds/2D process 900, but instead of step 915 of step 900, process 900' utilizes step 915' (see also the description of steps within step 915', given in FIG. 20B) to recalculate the forward solution at each calculation iteration of the Jacobian matrix. Eq. 32 and Eq. 33 can be expanded as $$\mu(x, y)\frac{\partial H_x(x, y)}{\partial t} = -\frac{\partial E_z(x, y)}{\partial y} \quad \text{(Eq. 39)}$$

$$\mu(x, y)\frac{\partial H_y(x, y)}{\partial t} = -\frac{\partial E_z(x, y)}{\partial x} \quad \text{(Eq. 40)}$$

$$\varepsilon(x, y)\frac{\partial E_z(x, y)}{\partial t} + \sigma(x, y)E_z(x, y) = \left(\frac{\partial H_y(x, y)}{\partial x} - \frac{\partial H_x(x, y)}{\partial y}\right) \quad \text{(Eq. 41)}$$

where $\mu(x, y)$, $\epsilon(x, y)$ and $\sigma(x, y)$ are 2D permeability, permittivity and electrical conductivity distributions, respectively. In the case of microwave imaging of a biological target, $\mu(x, y)=\mu_0$ (i.e., the permeability of free space) since the target is non-magnetic.

Figure 21A:
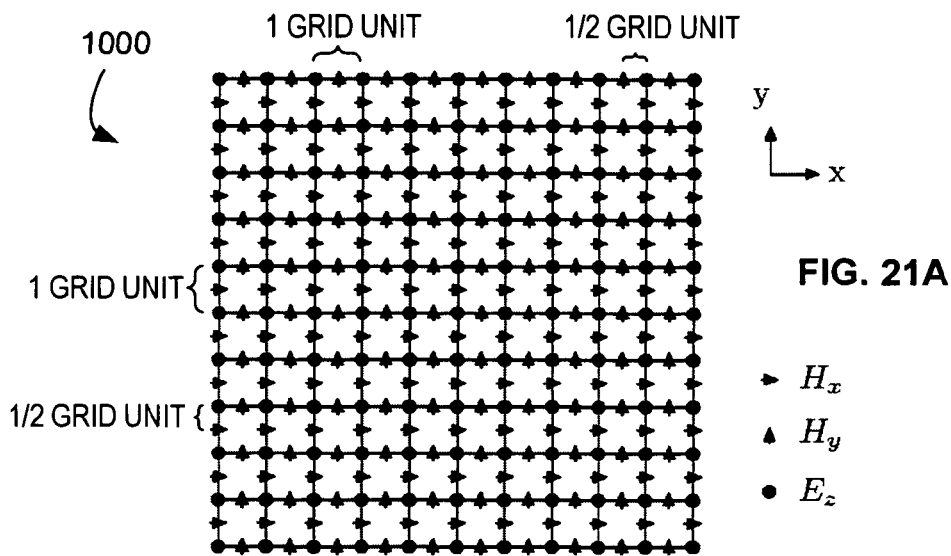
FIG. 21A and FIG. 21B illustrate staggered variants of a 2D grid that is used for discretizing Maxwell's equations.
Figure 21B:
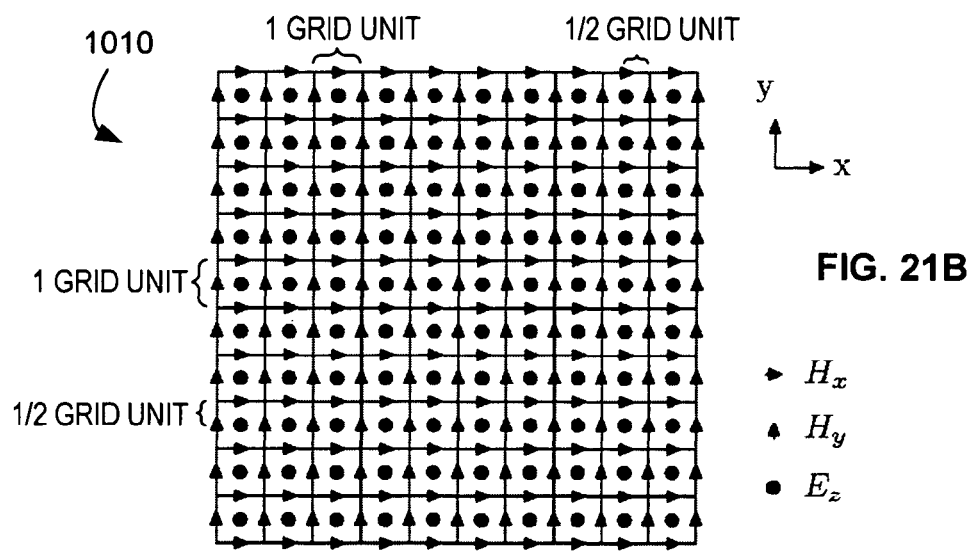

FIG. 21A and FIG. 21B illustrate staggered variants of a 2D grid, referred to herein as a 2D FDTD, grid that is used for discretizing Maxwell's equations (e.g., Eq. 32-33 or Eq. 39-41). FIG. 21A shows a grid 1000 that is referred to as the E-grid, and FIG. 21B shows a grid 1010 that is referred to as the H-grid. Each of grids 1000 and 1010 shows a plurality of electrical fields $E_z$ pointing outwards from the respective grids, at locations that are separated by a normalized grid unit length of 1 in each of the x and y directions, as shown. Grids 1000 and 1010 also show H vectors pointing in directions shown by arrows. Each H vector has an index located at half grid unit spacings denoted by $i\pm\frac{1}{2}$ or $j\pm\frac{1}{2}$, where i is the x index and j is the y index. Thus, grids 1000 and 1010 denote the same spatial arrangement, but each of grids 1000 and 1010 is centered ½ grid unit apart from the other, in each of the x and y dimensions. The following derivations refer to the coordinates of grid 1000. A difference representation can be applied to each of the temporal or spatial differential operators in each of Eq. 39-41, i.e., $$\frac{\partial f}{\partial \xi} = \frac{f_{\xi+\Delta\xi/2} - f_{\xi-\Delta\xi/2}}{\Delta\xi} \quad \text{(Eq. 42)}$$

where $\xi$ can be any of x, y or t, $\Delta x$ and $\Delta y$ represent the grid sizes in x and y directions respectively, and $\Delta t$ is a time increment. Difference form $$\frac{\partial}{\partial t}$$

involves half time steps, e.g., $(t+\Delta t/2)$ and $(t-\Delta t/2)$. Therefore, the terms in Eq. 39-41 that do not involve derivatives may replaced by averaged values on these two time steps, i.e., $$f(t) = \frac{f^{t+\Delta t/2} - f^{t-\Delta t/2}}{2}. \quad \text{(Eq. 43)}$$

Figure 22:
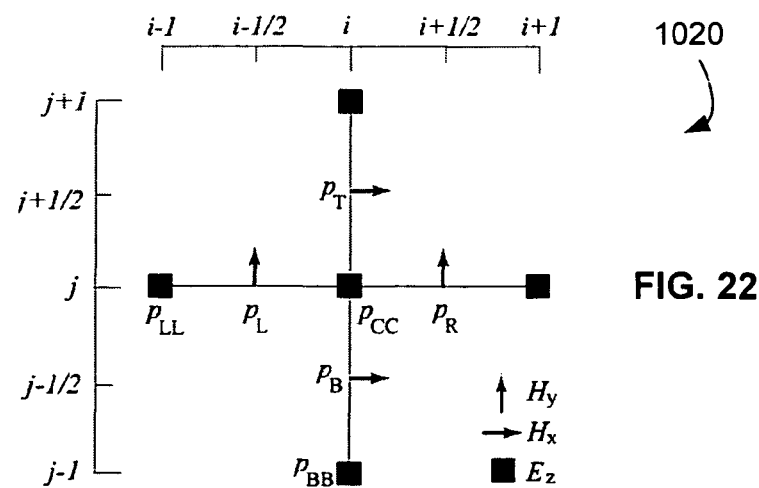
FIG. 22 shows a coordinate notation system for describing vectors about a point in grids used in 2D microwave imaging processes.

FIG. 22 shows a coordinate notation 1020 for describing vectors about a point (i,j) in each of grids 1000 and 1010. In FIG. 22, for a given $E_z$ at a point $p_{CC}$, points corresponding to locations of adjacent $H_y$ vectors at $i\pm\frac{1}{2}$ are named $p_L$ and $p_R$ respectively, and points corresponding to locations of adjacent $H_x$ vectors at $j\pm\frac{1}{2}$ are named $p_T$ and $p_B$ respectively. A point corresponding to the location of an adjacent $E_z$ at $i-1$ is named $p_{LL}$, and a point corresponding to the location of an adjacent $E_z$ at $j-1$ is named $p_{BB}$.

Converting Eq. 39-41 to utilize the difference representation of Eq. 42 and Eq. 43, and utilizing coordinate notation 1020, yields $$\mu(p_B)\frac{H_x^{n+\frac{1}{2}}(p_B) - H_x^{n-\frac{1}{2}}(p_B)}{\Delta t} = -\frac{E_z^n(p_{CC}) - E_z^n(p_{BB})}{\Delta y} \quad \text{(Eq. 44)}$$

$$\mu(p_L)\frac{H_y^{n+\frac{1}{2}}(p_L) - H_y^{n-\frac{1}{2}}(p_L)}{\Delta t} = -\frac{E_z^n(p_{CC}) - E_z^n(p_{LL})}{\Delta x} \quad \text{(Eq. 45)}$$

$$\varepsilon(p_{CC})\frac{E_z^{n+1}(p_{CC}) - E_z^n(p_{CC})}{\Delta t} + \quad \text{(Eq. 46)}$$
$$\sigma(p_{CC})\frac{E_z^{n+1}(p_{CC}) - E_z^n(p_{CC})}{2} =$$
$$\frac{H_y^{n+\frac{1}{2}}(p_R) - H_y^{n+\frac{1}{2}}(p_L)}{\Delta x} - \frac{H_x^{n+\frac{1}{2}}(p_T) - H_x^{n+\frac{1}{2}}(p_B)}{\Delta y}$$

where $p_L$, $p_R$, $p_T$, $p_B$, $p_{CC}$, $p_{LL}$ and $p_{BB}$ are as shown in FIG. 22.

To obtain explicit update equations for $H_x$, $H_y$ and $E_z$, terms from a given time step are moved to the left hand side of each of Eq. 44-46 (i.e., terms at time step $n+\frac{1}{2}$ for Eq. 44-45, and time step $n+1$ for Eq. 46) and the remainder is moved to the right hand side of each of the equations, yielding $$H_x^{n+\frac{1}{2}}(p_B) = cAHx(p_B)H_x^{n-\frac{1}{2}}(p_B) + \quad \text{(Eq. 47)}$$
$$cBHx(p_B)\left(\frac{E_z^n(p_{BB}) - E_z^n(p_{CC})}{\Delta y}\right)$$

$$H_y^{n+\frac{1}{2}}(p_L) = cAHy(p_L)H_y^{n-\frac{1}{2}}(p_L) + \quad \text{(Eq. 48)}$$
$$cBHy(p_L)\left(\frac{E_z^n(p_{CC}) - E_z^n(p_{LL})}{\Delta x}\right)$$

$$E_z^{n+1}(p_{CC}) = cAEz(p_{CC})E_z^n(p_{CC}) + \quad \text{(Eq. 49)}$$
$$cBEz(p_{CC})\left(\frac{H_y^{n+\frac{1}{2}}(p_R) - H_y^{n+\frac{1}{2}}(p_L)}{\Delta x} - \frac{H_x^{n+\frac{1}{2}}(p_T) - H_x^{n+\frac{1}{2}}(p_B)}{\Delta y}\right)$$

where cAHx, cBHx, cAHy, cBHy, cAEz and cBEz are coefficients defined by $$cAHx(p) = 1 \quad \text{(Eq. 50)}$$

$$cBHx(p) = \frac{\Delta t}{\mu(p)} \quad \text{(Eq. 51)}$$

$$cAHy(p) = 1 \quad \text{(Eq. 52)}$$

$$cBHy(p) = \frac{\Delta t}{\mu(p)} \quad \text{(Eq. 53)}$$

$$cAEz(p) = \frac{2\varepsilon(p) - \sigma(p)\Delta t}{2\varepsilon(p) + \sigma(p)\Delta t} \quad \text{(Eq. 54)}$$

$$cBEz(p) = \frac{2\Delta t}{2\varepsilon(p) + \sigma(p)\Delta t} \quad \text{(Eq. 55)}$$

and where $\epsilon(p)$ and $\sigma(p)$ are the permittivity and conductivity at point p.

Thus, given the field $E_z$ at t=0 for each point in a 2D FDTD mesh, Eq. 47-55 allow calculation of magnetic fields at t=$\Delta t/2$, and electric fields at t=$\Delta t$ for each point in the mesh. Repeating this update scheme provides a complete history for all field values for all time steps of interest.

Eq. 47-55, therefore, use an explicit "leap-frog" time stepping scheme. This scheme can be shown to be conditionally stable when the spatial and temporal step sizes $\Delta x$, $\Delta y$ and $\Delta t$ satisfy a stability criterion known as the Courant-Friedrichs-Lewy ("CFL") condition:

$$\Delta t \leq \frac{1}{c_{max}\sqrt{\frac{1}{\Delta x^2} + \frac{1}{\Delta y^2}}} \quad \text{(Eq. 56)}$$

where $c_{max}$ is a maximum wave speed throughout the 2D-FDTD grid. A related quantity (that will be used in the discussion below), the CFL number ("CFLN") is defined as $$CFLN = c_{max}\Delta t \sqrt{\frac{1}{\Delta x^2} + \frac{1}{\Delta y^2}} \quad \text{(Eq. 57)}$$

where the CFLN is a number that approaches 1 as the process iterates to steady state.

FIG. 20B shows intermediate steps of process step 915' of FIG. 20A. Step 960 initializes all fields to zero, e.g., $E_z^0=0$, $H_x^0=0$, $E_y^0=0$. Step 915 updates electric fields utilizing Eq. 49. Step 970 models effects induced by transmitting antennas (e.g., any of antennas or antenna arrays 30, 31, 102, 102', 202, 202', 302, 402 or 403) by means of describing initial values, electrical currents, voltages or magnetic currents. One method of modeling effects induced by an antenna is to model them as a z-oriented time-harmonic point current source, e.g., $$J_z(t, \vec{r}) = J_0 \cos(\omega t)\delta(\vec{r}-\vec{r}_s) \quad \text{(Eq. 58)}$$

where $J_0 = 1/(\omega\mu_0)$ is the amplitude and $\vec{r}_s$ is the spatial location of a point source, and $\delta$ is the Dirac delta function. It may also be advantageous to apply a low-pass filter to the source, to reduce steady-state numerical noise. For example, a filtered source may be described as $$J_z(t, \vec{r}) = w(t)J_0 \cos(\omega t)\delta(\vec{r}-\vec{r}_s) \quad \text{(Eq. 59)}$$

where $$w(t) = \begin{cases} 0.5 - 0.5 \cos(wt/\tau) & 0 \leq t \leq \tau \text{(Hamming)} \\ 0.54 - 0.46 \cos(wt/\tau) & 0 \leq t \leq \tau \text{(Hanning)} \\ 0.42 - 0.5 \cos(wt/\tau) + 0.08 \cos(wt/\tau), & 0 \leq t \leq \tau \text{(Blackman)} \\ 1 & t > \tau \end{cases} \quad \text{(Eq. 60)}$$

is the filter function, $\sigma$ being the length of the filter. A Hamming filter as described in Eq. 60 may be particularly useful for improving performance.

Step 975 updates magnetic fields utilizing Eq. 47 and Eq. 48. Step 980 determines whether a steady state has been reached. If not, step 995 increments the time step and process 915' returns to step 965. If step 980 determines that a steady state was reached, process 915' proceeds to step 985. In a time-harmonic imaging system, data required for imaging typically consists of amplitude and phase distributions, (i.e., a frequency domain solution). Since steps 965, 970 and 975 are time domain calculations, amplitude and phase information for the region being imaged must be extracted. In the steady state, all field components at all locations oscillate sinusoidally. One way to extract amplitude and phase of a sine curve is to record the values for one period and perform a fast Fourier transform ("FFT"). However, an analytical solution is also available. If field values at two consecutive time steps n and n+1 are recorded and can be expressed as $$f(n) = A \sin(n\Delta t + \phi_0) \quad \text{(Eq. 61)}$$

$$f(n+1) = A \sin(n\Delta t + \Delta t + \phi_0) \quad \text{(Eq. 62)}$$

and it can be shown that amplitude A and initial phase $\phi_0$ are equal to $$A = \csc(\Delta t)\sqrt{\frac{(\sin(\Delta t)f(n+1))^2 + }{(\cos(\Delta t)f(n+1) - f(n))^2}} \quad \text{(Eq. 63)}$$

$$\phi_0 = \tan^{-1}\left(\cot(\Delta t) - \frac{f(n)}{f(n+1)}\csc(\Delta t)\right) - n\Delta t \quad \text{(Eq. 64)}$$

where $\sin(\Delta t)$, $\cos(\Delta t)$, $\csc(\Delta t)$ and $\cot(\Delta t)$ can be pre-computed.

After step 985 extracts amplitude and phase for the entire region being imaged, step 990 identifies a subset of the amplitude and phase data that corresponds to locations of antennas (e.g., any of antennas or antenna arrays 30, 31, 102, 102', 202, 202', 302, 402 or 403) that receive microwave signals. The subset identified in step 990 may be used in step 925 of processes 900 and 900' to calculate a tolerance metric, to provide data for step 930 to determine whether the tolerance metric meets a pre-defined limit.

Computational efficiency of 2D-FDTD process 900' relative to 2Ds/2D process 900 was established by estimating a number of floating-point operations ("flops") required by processes 900 and 900' to reach steady state for simulated grids. Rectangular grids of size $N_x = N_y = N + 2N_{PML}$, where $N_x$ and $N_y$ were the number of grid elements in x and y directions respectively, and $N_{PML}$ was the thickness of a perfectly matching, absorbing boundary layer, were simulated. For simplicity, only the iterating steps (e.g., steps 920 and 930 for process 900, and steps 920, 930 and 935 for process 900') were counted.

For 2Ds/2D process 900, utilizing certain choices for the boundary layer and finite element modeling, one estimate of the total number of flops required for convergence was found to be $$F_{2Ds/2D} \approx \frac{\pi^3}{4}N^4 + \frac{7\pi^2}{4}N^3 + \frac{\pi}{2}N^2. \quad \text{(Eq. 65)}$$

For 2Ds-FDTD/2D process 900', a total number of flops required may be estimated by multiplying the flops per iteration by the number of iterations required:

$$F_{2Ds\text{-}FDTD/2D} = F_{steady} F_{iter}. \quad \text{(Eq. 66)}$$

Counting the algebraic operations required yields a result of $F_{iter} = 28(N + 2N_{PML})^2$ flops per iteration. If mesh resolution is given by R, wave speed in the coupling medium is given as $c_{bk}$, and maximum wave speed among all inhomogeneities in a target is given as $c_{max}$, the number of iterations (time steps) required to reach steady state can be shown to be $$F_{steady} = \frac{2\sqrt{2}\, N \times c_{max}}{CFLN \times c_{bk}} \quad \text{(Eq. 67)}$$

so that the total number of flops required by 2Ds-FDTD/2D process 900' is $$F_{2Ds\text{-}FDTD/2D} = F_{steady} F_{iter} \quad \text{(Eq. 68)}$$
$$= 56\sqrt{2}\, N(N + 2N_{PML})^2 \frac{c_{max}}{CFLN \times c_{bk}}$$

and since at stability, $CFLN \approx 1$, $$F_{2Ds\text{-}FDTD/2D} \approx 56\sqrt{2}\, N(N + 2N_{PML})^2 \frac{c_{max}}{c_{bk}}. \quad \text{(Eq. 69)}$$

$c_{max}/c_{bk}$ relates to the contrast of the target being imaged to the background medium in which it is immersed; it can be shown that $$\frac{c_{max}}{c_{bk}} \approx \sqrt{\frac{\varepsilon_{bk}}{\varepsilon_{min}}} \quad \text{(Eq. 70)}$$

which is the square root of the permittivity contrast. Utilizing a reasonably high assumption (for microwave imaging) of $\varepsilon_{bk}/\varepsilon_{max} = 10$ and $N_{PML} = 8$, the total number of flops required for 2Ds-FDTD/2D process 900' to reach steady state becomes a pure function of N.

Figure 23:
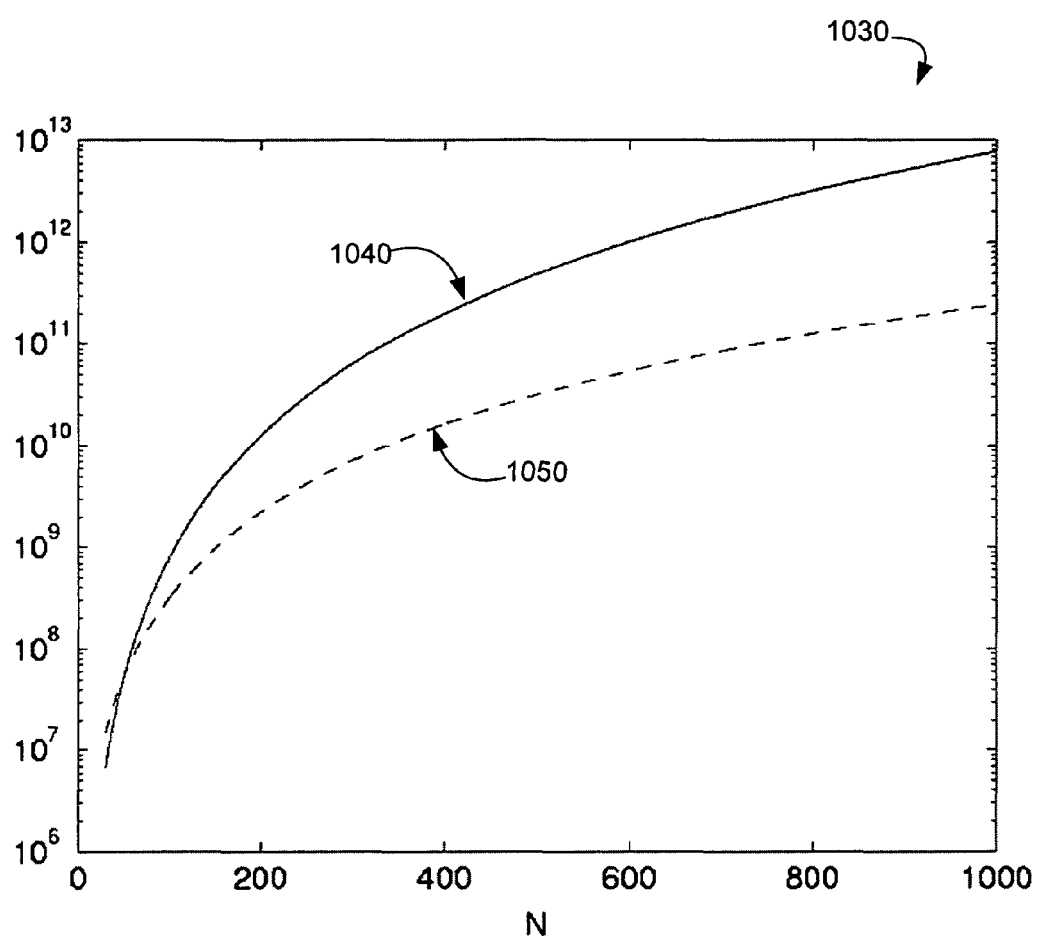
FIG. 23 shows a plot of floating point operations required to reach steady state for two 2D microwave imaging reconstruction processes.

FIG. 23 shows a plot 1030 of flops required to reach steady state for 2Ds/2D process 900 (indicated as line 1040) and 2Ds-FDTD/2D process 900' (indicated as dashed line 1050). It can be seen that as N increases (increasing the size of the forward problem), computation time for 2Ds/2D process 900 increases faster than computation time for 2Ds-FDTD/2D process 900'. When N exceeds about 300, flops required for process 900' to reach steady state exceed flops required for process 900 to reach steady state by about a factor of 10.

2D microwave imaging utilizing 2D forward methods may distort a final image due to mismatch in the forward model—e.g., the assumptions made in calculating 2D forward solutions in steps 915 and 915' may not be valid. For example, dielectric property variations may have variation in the z axis; antennas may not be infinite line sources, and propagating waves may not always be pure TM waves. A useful technique to improve on 2D microwave imaging is a 3Ds/2D model that may be considered an intermediate step between 2D and full 3D modeling. In 3Ds/2D modeling, a forward solution is modeled as a 3D scalar model while images are reconstructed in a 2D plane, therefore 3Ds/2D modeling represents a direct extension of 2Ds/2D process 900 and 2Ds-FDTD/2D process 900'. The assumption that dielectric property variations do not vary in the z-axis is retained from the 2D models, since only 2D images are reconstructed. However, antennas are modeled as finite-length or point sources. 3Ds/2D modeling demonstrates high efficiency for modeling 3D wave propagation, and limited reduction in accuracy, as compared with full 3D vector forward modeling.

In a 3D analogue to Eq. 38, a finite element technique is an attractive choice because of sparseness of a matrix system associated therewith, and its capability for modeling curved boundaries. If a forward domain $\Omega$ is a 3D volume (e.g., volume (e.g., volume of forward mesh 878(1), FIG. 19B) and basis/weighting functions are defined over 3D elements, a system of equations can be constructed utilizing a Galerkin method:

$$\langle \nabla E_z(\vec{r}), \nabla \phi_l \rangle - \langle k^2 E_z(\vec{r}), \nabla \phi_l \rangle - \oiint_{\partial \Omega} \nabla \phi_l E_z(\vec{r}) \cdot \hat{n}\, ds = \quad \text{(Eq. 71)}$$
$$-j\omega\mu_0 \langle J_z(\vec{r}), \phi_l \rangle$$

where $(\cdot, \cdot)$ denotes integration of the product of the two terms over forward domain $\Omega$, $\partial\Omega$ is the surface of domain $\Omega$, $\phi_l$ is a weighting function, $\hat{n}$ is a unit vector normal to a volume surface. By satisfying Eq. 71 for weighting functions associated with all nodes in $\Omega$, a system of N equations in N unknowns—the electric field values at all of the nodes—can be constructed in matrix form as $$AE = b, \quad \text{(Eq. 72)}$$

where the (i, l)-th element of A is $$a_{i,l} = (\nabla \phi_i, \Delta \phi_l) - (k^2 \phi_i, \phi_l) \qquad \text{(Eq. 73)}$$

and the l-th element of b is $$b_l = -j\omega\mu_0 (J_z(\vec{r}), \phi_l). \qquad \text{(Eq. 74)}$$

Note that A contains all of the information pertaining to electrical property distributions within a parameter mesh (e.g., parameter mesh 876(2), FIG. 19B) while b contains all of the source antenna data.

With the choice of a first order Bayliss-Turkel radiation boundary condition, a continuous equation can be produced that can be discretized and solved with linear matrix solvers, producing $$\langle \nabla E_z(\vec{r}), \nabla \phi_l \rangle - \langle k^2 E_z(\vec{r}), \phi_l \rangle - \qquad \text{(Eq. 75)}$$

$$\oint_{\partial\Omega} \left( jk E_z(\vec{r}) - \frac{E_z(\vec{r})}{2r} \right) \phi_l \hat{r} \cdot \hat{n} \, ds = -j\omega\mu_0 \langle J_z(\vec{r}), \phi_l \rangle$$

where $\hat{r}$ is a radial vector.

When antennas are of finite length (such as, e.g., any of antennas or antenna arrays 30, 31, 102, 102', 202, 202', 302, 402 or 403), direction of $\hat{r}$ at $\partial\Omega$ changes as a function of a section of an antenna that is referenced. To account for this variation in the direction of $\hat{r}$, its direction may be integrated along an antenna length to produce an effective $\hat{r}$. When sources are not at a center of a volume being imaged, an immediate impact is produced on the surface integral term in Eq. 75: if $\hat{r}$ is taken as a unit vector from each individual source corresponding to $J_z(\hat{r})$, matrix A will vary for each transmitter. This would have significant computational consequences in that Eq. 72 would then have to be solved independently for each source. However, an alternative approach constructs a $\hat{r} \cdot d\hat{s}$ product utilizing a weighted sum of $\hat{r}$s from all source antennas in an array—even if only one is active at a time. In this way, the contribution from the surface integral in Eq. 75 becomes independent of the active antenna, so that A is identical for all sources.

Figure 24:
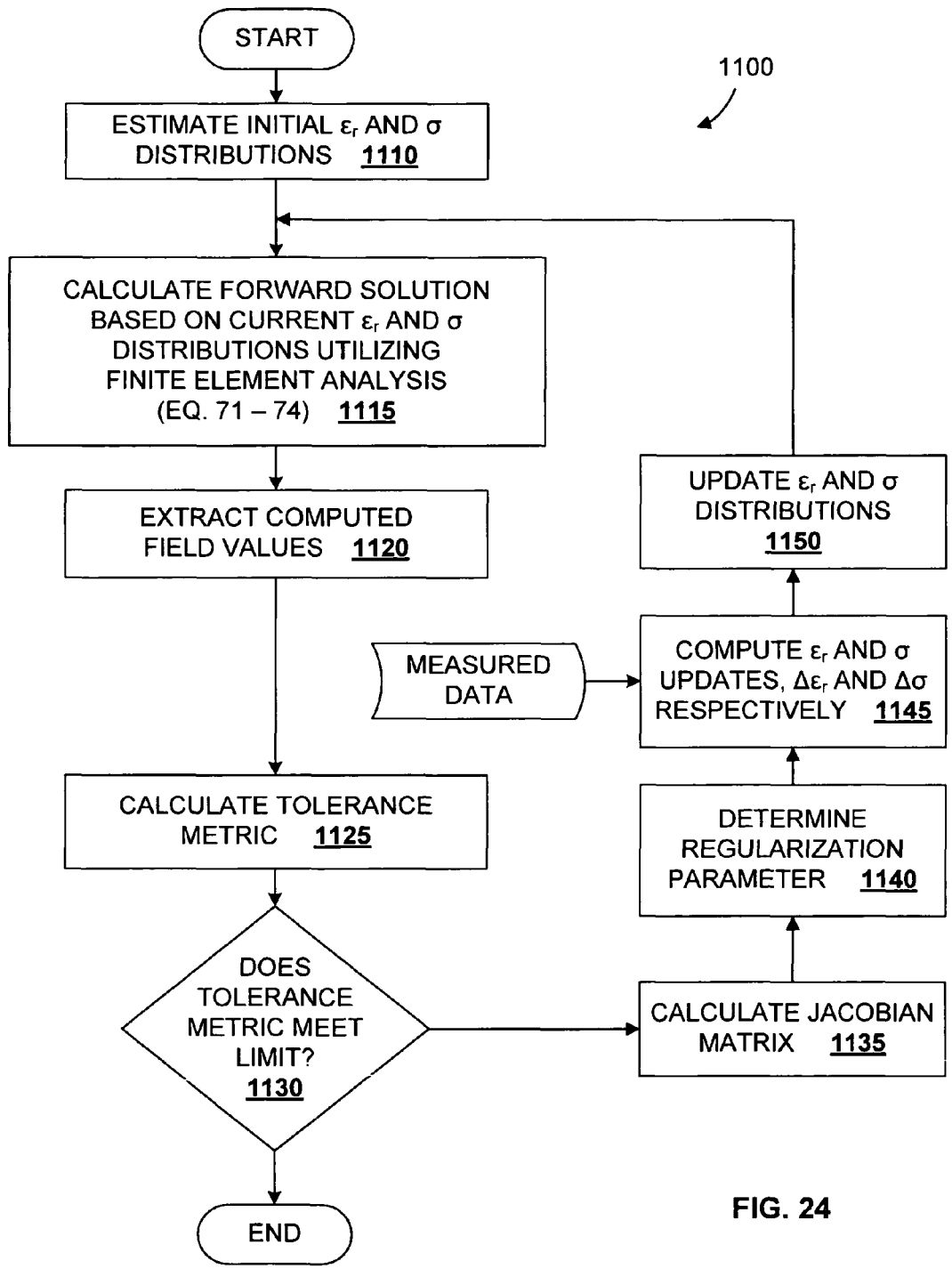
FIG. 24 is a flowchart illustrating a 3Ds/2D microwave imaging process 1100 in accord with an embodiment.

FIG. 24 is a flowchart illustrating a 3Ds/2D microwave imaging process 1100. Process 1100 is for example implemented by microwave imaging system 10, with processor 36 executing software 35 (see FIG. 1). 3Ds/2D reconstruction process 1100 may provide advantages in that it creates microwave images that do not have certain artifacts that may arise in 2D images, but process 1100 may calculate images faster than full 3D microwave imaging processes. In process 1100, step 1110 estimates initial $\epsilon_r$ and $\sigma$ distributions. Step 1115 calculates forward solutions based on current $\epsilon_r$ and $\sigma$ distributions (e.g., in the first iteration, step 1115 utilizes the initial $\epsilon_r$ and $\sigma$ distributions from step 1110, and in subsequent iterations step 1115 utilizes the updated $\epsilon_r$ and $\sigma$ distributions from step 1150). Step 1120 extracts computed field values. Step 1125 calculates a tolerance metric. Step 1130 determines whether the tolerance metric meets a pre-determined limit. If not, step 1135 calculates a Jacobian matrix, step 1140 determines a regularization parameter, step 1145 computes $\epsilon_r$ and $\sigma$ updates, $\Delta\epsilon_r$ and $\Delta\sigma$ respectively, utilizing measurement data, and step 1150 updates the $\epsilon_r$ and $\sigma$ distributions as $\epsilon_r^{i+1} = \epsilon_r^i + \Delta\epsilon_r$ and $\sigma^{i+1} = \sigma^i + \Delta\sigma$, where i is an iteration index, returning to step 1115. If step 1130 determines that the tolerance metric meets the pre-determined limit, process 1100 ends.

In 3Ds/3D and 3Dv/3D microwave imaging processes, a parameter mesh (e.g., parameter mesh 880(1), FIG. 19C or 880(2), FIG. 19D) is created over a volume, as opposed to an area, so that dielectric property distributions are 3D distributions, and 2D images may be constructed by sampling the property distributions over arbitrary planes within the imaged volume. A forward mesh in a 3Ds/3D process may be a cylindrical mesh concentrically aligned with a circular antenna array, as shown in FIG. 19C. A forward mesh in a 3Dv/3D process may be a rectangular mesh about an antenna array, as shown in FIG. 19D, and may be visualized as a 3D analogue of grids 1000 and 1010, with 3D E-grids and H-grids offset from one another by one-half of a grid unit in each of the x-, y-, and z-directions.

Figure 25:
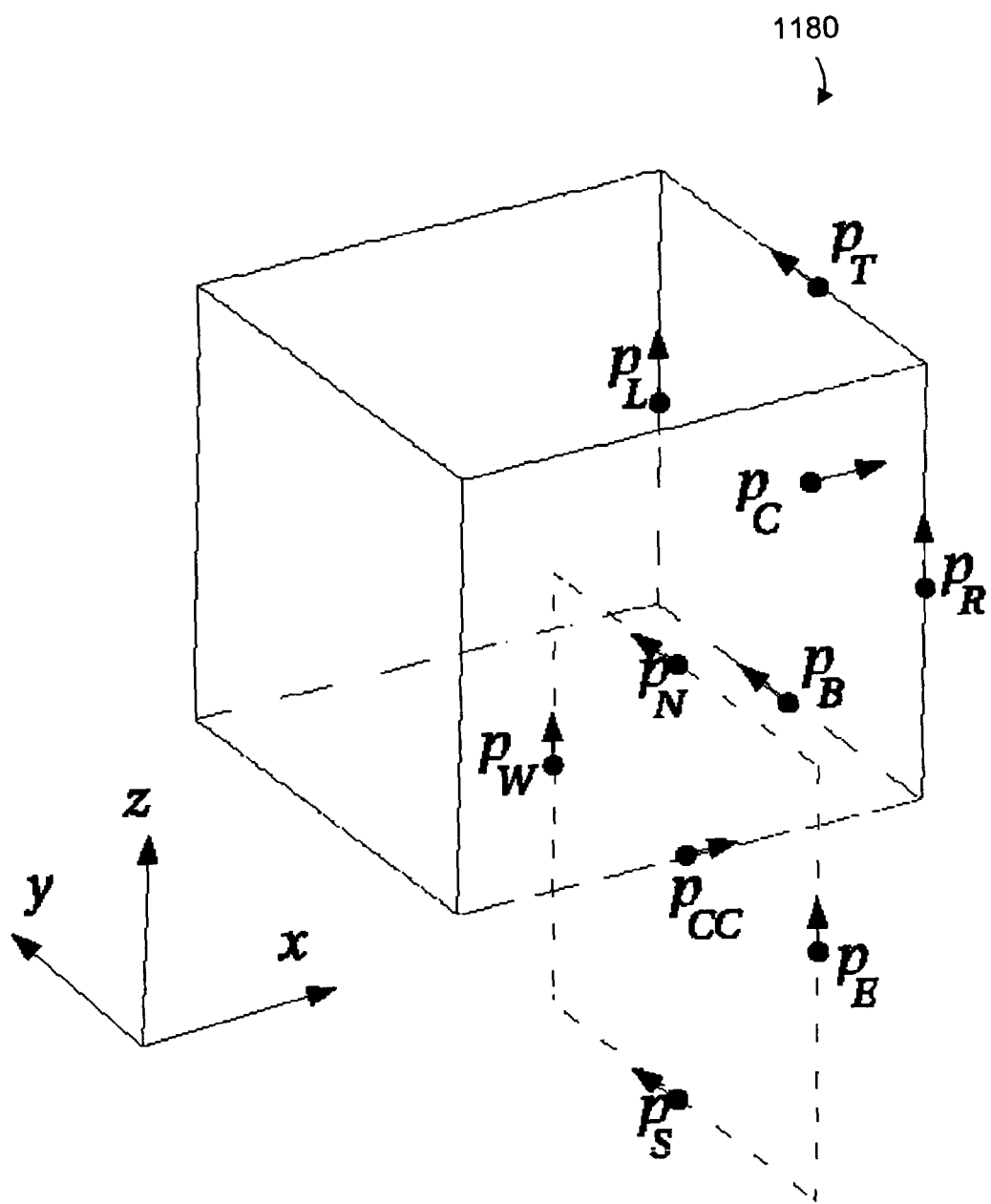
FIG. 25 shows a 3D coordinate notation 1180 for describing vectors about a point.

FIG. 25 shows a 3D coordinate notation 1180 for describing vectors about a point. In FIG. 25, for a given point $p_{CC}$, points at the same x value but at $\pm\frac{1}{2}$ grid spacing in z and y respectively are named $p_N$, $p_S$, $p_E$ and $p_W$. A point at $+\frac{1}{2}$ grid spacing in each of the x and z directions is named $p_C$. Points at the same x value as $p_C$ but at $\pm\frac{1}{2}$ grid spacing in z and y respectively are named $p_T$, $p_B$, $p_L$ and $p_R$.

Equations that may be used to implement a 3Dv/3D microwave imaging process are derived as follows. Coordinate stretching coefficients may be defined as $$s_\xi(\xi) = \kappa_\xi(\xi) + \frac{\sigma_\xi(\xi)}{j\omega\varepsilon} \qquad \text{(Eq. 76)}$$

where $\xi = x, y$ or $z$, and $\kappa_{\xi 0}(\xi)$ and $\sigma_\xi(\xi)$ are defined by $$\kappa_{\xi 0}(\xi) = 1 + \kappa_{max}\left(\frac{\xi}{\Delta\xi}\right)^m \qquad \text{(Eq. 77)}$$

$$\sigma_\xi(\xi) = \sigma_{max}\left(\frac{\xi}{\Delta\xi}\right)^m \qquad \text{(Eq. 78)}$$

with $\kappa_{max}$, $\sigma_{max}$, and m being parameters. With these terms defined, a stretching tensor s may be written as $$\bar{\bar{s}} = \begin{pmatrix} \frac{s_y s_z}{s_x} & 0 & 0 \\ 0 & \frac{s_z s_x}{s_y} & 0 \\ 0 & 0 & \frac{s_x s_y}{s_z} \end{pmatrix} \qquad \text{(Eq. 79)}$$

and then Maxwell's equations (Eq. 32, 33) may be rewritten, using this notation, as $$\nabla \times \vec{E}(\vec{r}) = -j\omega\mu\bar{\bar{s}}\vec{H}(\vec{r}) \qquad \text{(Eq. 80)}$$

$$\nabla \times \vec{H}(\vec{r}) = j\omega\varepsilon\bar{\bar{s}}\vec{E}(\vec{r}). \qquad \text{(Eq. 81)}$$

If magnetic and electric fields are defined as $$B_x = \mu\frac{s_z}{s_x}H_x \qquad \text{(Eq. 82)}$$

$$B_y = \mu\frac{s_x}{s_y}H_y \qquad \text{(Eq. 83)}$$

$$B_z = \mu\frac{s_y}{s_z}H_z \qquad \text{(Eq. 84)}$$

-continued $$P_x = s_y E_x \quad \text{(Eq. 85)}$$

$$P_y = s_z E_y \quad \text{(Eq. 86)}$$

$$P_z = s_x E_z \quad \text{(Eq. 87)}$$

$$Q_x = \frac{s_z}{s_x} E_x \quad \text{(Eq. 88)}$$

$$Q_y = \frac{s_x}{s_y} E_y \quad \text{(Eq. 89)}$$

$$Q_z = \frac{s_y}{s_z} E_z \quad \text{(Eq. 90)}$$

then upon applying central differences in both time and space, a discretized update scheme for $H_x$ can be shown as a two step process:

$$B_x^{n+1/2}(p_C) = cABy(p_C) B_x^{n-1/2}(p_C) - \quad \text{(Eq. 91)}$$
$$cBBy(p_C) \left( \frac{E_z^n(p_R) - E_z^n(p_L)}{\Delta y} - \frac{E_y^n(p_r) - E_y^n(p_B)}{\Delta z} \right)$$

$$H_x^{n+1/2}(p_C) = cAHz(p_C) H_x^{n-1/2}(p_C) - \quad \text{(Eq. 92)}$$
$$cBHz(p_C)(cCHx(p_C) B_x^{n+1/2}(p_C) - cDHx(p_C) B_x^{n+1/2}(p_C))$$

where $$cCH\xi(p) = \kappa_\xi(p) - \frac{\sigma_\xi^*(p)\Delta t}{2\epsilon_0} \quad \text{(Eq. 93)}$$

$$cDH\xi(p) = \kappa_\xi(p) + \frac{\sigma_\xi^*(p)\Delta t}{2\epsilon_0} \quad \text{(Eq. 94)}$$

$$cAB\xi(p) = \frac{cCH\xi(p)}{cDH\xi(p)} \quad \text{(Eq. 95)}$$

$$cBB\xi(p) = \frac{1}{cDH\xi(p)} \quad \text{(Eq. 96)}$$

$$cAH\xi(p) = cAB\xi(p) \quad \text{(Eq. 97)}$$

$$cBH\xi(p) = \frac{1}{\mu(p)\Delta t} cBB\xi(p) \quad \text{(Eq. 98)}$$

are coefficients with $\xi$-=x, y or z, and spatial points $p_C$, $p_L$ etc. are as shown in FIG. 25. Update equations may also be derived as:

$$P_x^{n+1/2}(p_{CC}) = cAP(p_{CC}) P_x^{n-1/2}(p_{CC}) - cBP(p_{CC}) \quad \text{(Eq. 99)}$$
$$\left( \frac{H_z^{n+1/2}(p_N) - H_z^{n+1/2}(p_S)}{\Delta y} - \frac{H_y^{n+1/2}(p_W) - H_y^{n+1/2}(p_E)}{\Delta z} \right)$$

$$Q_x^{n+1/2}(p_{CC}) = cAEy(p_{CC}) Q_x^{n-1/2}(p_{CC}) - \quad \text{(Eq. 100)}$$
$$cBEy(p_{CC})(P_x^{n+1/2}(p_{CC}) - P_x^{n+1/2}(p_{CC}))$$

$$E_x^{n+1/2}(pcc) = cAEz(p_{CC}) E_x^{n-1/2}(p_{CC}) - \quad \text{(Eq. 101)}$$
$$cBEz(p_{CC})(cCEx(p_{CC}) Q_x^{n+1/2}(p_{CC}) - cDEx(p_{CC}) Q_x^{n+1/2}(p_{CC}))$$

where $$cAP(p) = \frac{\epsilon(p)/\Delta t - \sigma/2}{\epsilon(p)/\Delta t + \sigma/2} \quad \text{(Eq. 102)}$$

$$cBP(p) = \frac{1}{\epsilon(p)/\Delta t + \sigma/2} \quad \text{(Eq. 103)}$$

$$cCE\xi(p) = \kappa_\xi(p) - \frac{\sigma_\xi(p)\Delta t}{2\epsilon_0} \quad \text{(Eq. 104)}$$

$$cDE\xi(p) = \kappa_\xi(p) + \frac{\sigma_\xi(p)\Delta t}{2\epsilon_0} \quad \text{(Eq. 105)}$$

$$cAE\xi(p) = \frac{cCEx(p)}{cDE\xi(p)} \quad \text{(Eq. 106)}$$

$$cBE\xi(p) = \frac{1}{cDE\xi(p)} \quad \text{(Eq. 107)}$$

are update coefficients. Analogously to the derivations of the equation for $H_x$ and $E_x$ in Eq. 91-92 and Eq. 99-101 respectively, the corresponding y and z components of the fields can be obtained by rotating the subscripts, i.e., x to y to z to x, along with the relative positions of the points shown in coordinate notation 1180, FIG. 25.

Figure 26:
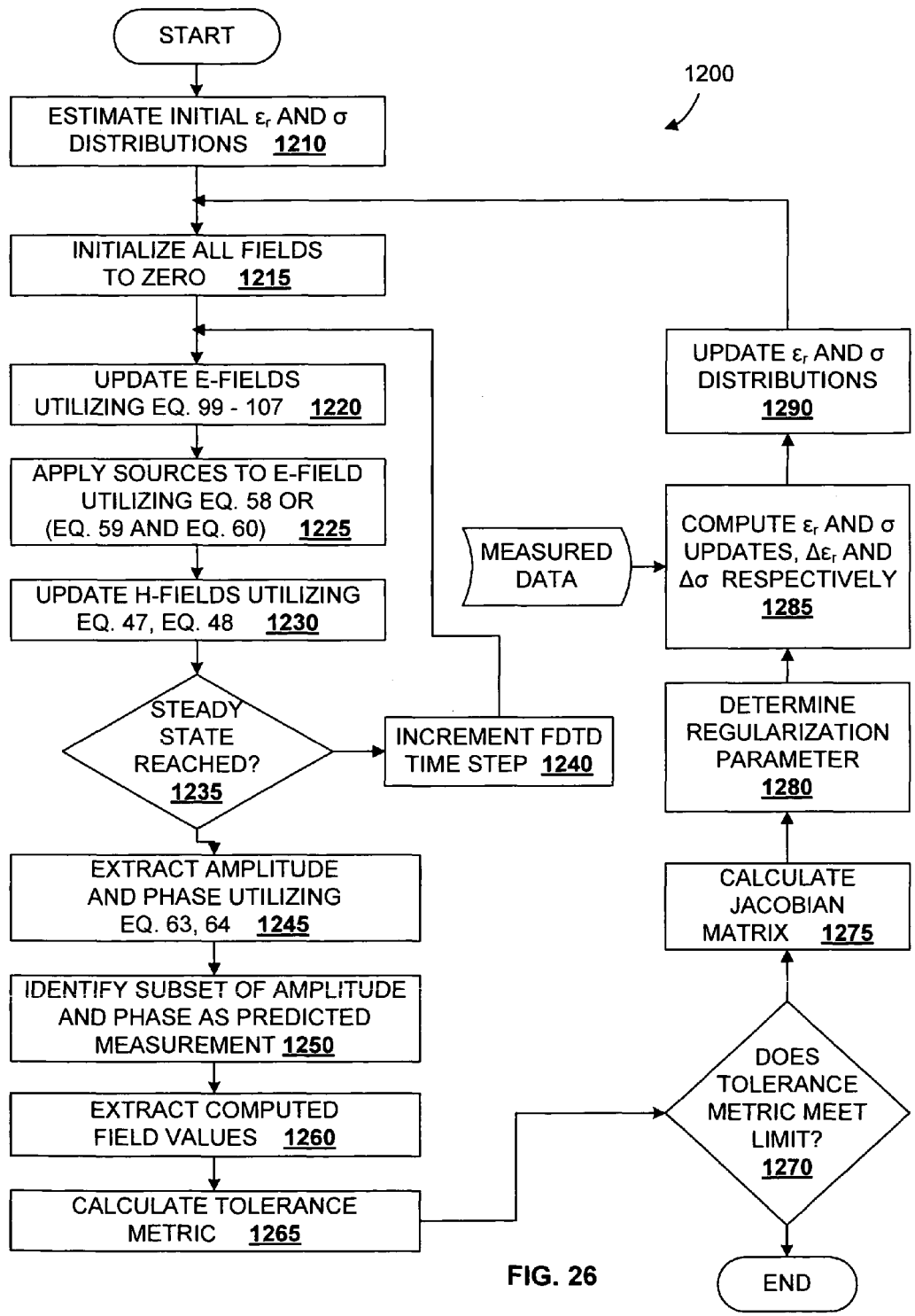
FIG. 26 is a flowchart illustrating a 3Dv/3D microwave imaging process 1200, in accord with an embodiment.

FIG. 26 is a flowchart illustrating a 3Dv/3D microwave imaging process 1200. Process 1200 is for example implemented by microwave imaging system 10, with processor 36 executing software 35 (see FIG. 1). 3Dv/3D reconstruction process 1200 may provide the advantages of providing 3D images with reduced calculations as compared to existing 3D microwave imaging techniques, due in part to process 1200 updating a forward solution at each iteration, instead of utilizing a forward solution that remains static as dielectric properties iterate.

In process 1200, step 1210 estimates initial $\epsilon_r$ and $\sigma$ distributions. Steps 1215 through 1250 provide an FDTD forward field calculation, as presently described. Step 1215 initializes all fields to zero. Step 1220 updates electric fields utilizing Eq. 99-107. Step 1225 models effects induced by transmitting antennas (e.g., any of antennas or antenna arrays 30, 31, 102, 102', 202, 202', 302, 402 or 403), utilizing Eq. 58 or (Eq. 59 and 60). Like step 970 of process 915', step 1225 may utilize low pass filtering; a Hamming filter may be particularly useful for improving performance. Step 1230 updates magnetic fields utilizing Eq. 91-98. Step 1235 determines whether a steady state has been reached. If not, step 1240 increments the time step and process 1200 returns to step 1220. If step 1235 determines that a steady state was reached, process 1200 proceeds to step 1245. Step 1250 extracts amplitude and phase for the entire region being imaged. Step 1260 identifies a subset of the amplitude and phase data that corresponds to locations of antennas (e.g., any of antennas or antenna arrays 30, 31, 102, 102', 202, 202', 302, 402 or 403) that receive microwave signals.

Step 1265 calculates a tolerance metric. Step 1270 determines whether the tolerance metric meets a predetermined limit. If not, step 1275 calculates a Jacobian matrix, and step 1280 determines a regularization parameter. Step 1285 computes $\epsilon_r$ and $\sigma$ updates, $\Delta\epsilon_r$ and $\Delta\sigma$ respectively. utilizing measurement data, and step 1290 updates the $\epsilon_r$ and $\sigma$ distributions as $\epsilon_r^{i+1} = \epsilon_r^i + \Delta\epsilon_r$ and $\sigma^{i+1} = \sigma^i + \Delta\sigma$, where i is an iteration index, after which process 1200 returns to step 1215. If step 1270 determines that the tolerance metric meets the predetermined limit, process 1200 ends.

The nodal adjoint method described in microwave imaging process 800 (FIG. 18) may be an advantageous technique for a 3Dv/3D imaging process. Another advantageous technique may be achieved by storing field values from a given forward solution iteration and supplying these field values as a starting point for the next iteration; this is denoted a "fast-FDTD" technique herein. In the iterative reconstruction process, since dielectric property distributions converge from an initial estimate to a final set of values, the forward solutions likewise converge; thus supplying initial data that closely resembles final data (instead of, for example, initializing all fields to zero at the start of each forward iteration) makes the calculation converge much more quickly. The fast-FDTD technique may reduce the number of time steps in an FDTD calculation to ½ to ⅓ the number of time steps required for convergence when each forward solution begins with fields initialized to zero. From a wave point of view, when a source is located close to boundaries of a forward domain, a time required to reach steady state takes approximately twice as long as when the source is located at the center of the domain, because the average distance between the source and receivers increases. When a microwave imaging system is configured such that a target is located at the approximate center of an illumination tank (e.g., any of illumination tanks 32, 104, 204, 304 or 404), a modeled electromagnetic wave propagates to a receiver in less time than from sources near borders of an associated parameter mesh.

Since values for permittivity, conductivity and/or dispersion coefficients thereof are obtained for each parameter mesh location in 3D image reconstruction process 1200 described above, images may be reconstructed from the values in a variety of ways. For example, 3D images may be viewed as a sequence of 2D images, such as a vertical stack of images of a horizontal plane. Alternatively, a plane may be chosen that is not necessarily horizontal or vertical, and values that intersect the chosen plane may be displayed. In another alternative, a viewing utility may display all of the values of the reconstructed image simultaneously, from a particular point of view, with certain values displayed as less dense or transparent, and other values displayed as more dense or opaque, so that a viewer's attention is directed to the regions with more dense or opaque values. A viewing utility may include controls that allow a viewer to move or rotate the displayed values relative to the point of view, so that the viewer may appreciate the structure of the imaged subject from different angles.

The changes described above, and others, may be made in the microwave imaging system and processes described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A microwave imaging process, comprising:
   illuminating a target with microwaves from a transmitting antenna,
   receiving microwaves scattered by the target at a plurality of receiving antennas to form microwave data,
   repeating the illuminating and receiving steps for a plurality of transmitting antennas,
   repeating the illuminating, receiving, and repeating steps for a plurality of microwave frequencies; and
   processing the microwave data to form permittivity and conductivity images by:
   (a) selecting a frequency relationship for each of permittivity and conductivity,
   (b) determining permittivity and conductivity dispersion coefficients for the permittivity and conductivity frequency relationships,
   (c) calculating permittivity and conductivity distributions for each frequency of the plurality of frequencies,
   (d) determining forward solutions at multiple frequencies from initial estimates of permittivity and conductivity distributions,
   (e) determining a dispersion coefficient based Jacobian matrix,
   (f) determining dispersion coefficient updates using the microwave data,
   (g) updating the dispersion coefficients,
   (h) recalculating current permittivity and conductivity distributions for each frequency of the plurality of frequencies, and
   (i) determining the forward solutions at multiple frequencies from the current permittivity and conductivity distributions.

2. The process of claim 1, further comprising:
   (j) calculating a multi-frequency difference vector between measured and computed electric field values,
   (k) computing a tolerance metric, and
   repeating steps (e), (f), (g), (h), (i), (j) and (k) until the tolerance metric meets a pre-defined limit.

3. The process of claim 1, wherein selecting the frequency relationship for each of permittivity and conductivity comprises selecting a permittivity relationship equation from the group consisting of $$\varepsilon_r = A\omega + B,$$
$$\ln(\varepsilon_r) = A\omega + B,$$
$$\varepsilon_r = A\ln(\omega) + B,$$
$$\ln(\varepsilon_r) = A\ln(\omega) + B \text{ and}$$
$$\varepsilon_r = \sum_{i=0}^{N} A_i \omega^i;$$

where $\varepsilon_r$ denotes relative permittivity, $\omega$ denotes angular frequency, i is a summation index, N is a polynomial order, and A and B are the permittivity dispersion coefficients.

4. The process of claim 1, further comprising utilizing the permittivity dispersion coefficients to form an image.

5. The process of claim 1, wherein selecting the frequency relationship for each of permittivity and conductivity comprises selecting a conductivity relationship equation from the group consisting of $$\sigma = A\omega + B,$$
$$\ln(\sigma) = A\omega + B,$$

-continued $$\sigma = A\ln(\omega) + B,$$
$$\ln(\sigma) = A\ln(\omega) + B \text{ and}$$
$$\sigma = \sum_{i=0}^{N} A_i \omega^i;$$

where σ denotes conductivity, ω denotes angular frequency, i is a summation index, N is a polynomial order, and A and B are the conductivity dispersion coefficients.

6. The process of claim 1, further comprising utilizing the conductivity dispersion coefficients to form an image.

7. The process of claim 1, wherein the step of determining the forward solutions at multiple frequencies comprises utilizing electric field values from a previous step of recalculating the forward solutions as a starting point.

8. The process of claim 1, wherein the step of determining the dispersion coefficient based Jacobian matrix comprises constructing a Jacobian matrix J, wherein elements J((s,r),τ) are defined by the relationship $$J((s,r),\tau) = \sum_{e \in \Omega_\tau} (D_\tau^e E_s^e)^T E_r^e;$$

where $\Omega_\tau$ denotes a region within which a basis function $\phi_\tau \neq 0$, $\Sigma_{e \in \Omega_\tau}$ denotes a summation over forward elements which are located within $\Omega_\tau$, $E_s^e \{E_s(\vec{p}_\kappa^e)\}_{\kappa=1}^M$ and $E_r^e = \{E_r(\vec{p}_\kappa^e)\}_{\kappa=1}^M$ model electric field values at vertices $(\vec{p}_\kappa^e)_{\kappa=1}^M$ of an e-th forward element due to ones of the transmitting antennas at s and r, respectively, T indicates the transpose of a matrix, $D_\tau^e$ is a weighting matrix with each element defined by $$d_{i_e,l_e}^\tau = \int_{\Omega_e} \phi_{i_e}(\vec{r}) \phi_{l_e}(\vec{r}) \varphi_\tau(\vec{r}) d\vec{r},$$

where $\phi_{i_e}(\vec{r})$, $\phi_{l_e}(\vec{r})$ and $\phi(\vec{r})$ represent basis functions over forward and parameter meshes, respectively, $i_e=1, 2, \ldots M$ and $l_e=1, 2, \ldots M$ are local node indices, M is a total node number for a single forward element, and $\Omega_e$ is a spatial domain occupied by the e-th forward element.

9. The process of claim 1, the images being three-dimensional images.

10. The process of claim 1, wherein the receiving step comprises receiving microwaves scattered by the target at a plurality of receiving antennas, the receiving antennas and the transmitting antenna forming a plane, to form the microwave data.

11. The process of claim 1, wherein the step of determining the dispersion coefficient based Jacobian matrix comprises constructing a Jacobian matrix J, wherein elements J((s,r),τ) are defined by the relationship $$J((s,r),\tau) = \sum_{n \in \Omega_\tau} \left( \frac{\sum_{e \in \Omega_n} V_e}{M} \right) \varphi_\kappa(\vec{p}_n) E_s(\vec{p}_n) E_r(\vec{p}_n),$$

where $\Omega_\tau$ denotes a region within which a basis function $\phi_\tau \neq 0$, $\Sigma_{n \in \Omega_\tau}$ refers to a summation over forward nodes which fall inside $\Omega_\tau$, $\Sigma_{e \in \Omega_n}$ refers to a summation over forward elements that share an n-th forward node within $\Omega_n$, $\phi_\kappa(\vec{p}_n)$ is the value of parameter mesh basis function at the set of forward nodes $\vec{p}_n$ within $\Omega_\tau$, $E_s(\vec{p}_n)$ and $E_r(\vec{p}_n)$ are nodal electrical field values computed directly from a forward problem, and $V_e$ is a volume of an e-th forward element within $\Omega_n$.

12. The process of claim 11, wherein the step of constructing comprises utilizing a log magnitude phase format algorithm.

13. The process of claim 11, further comprising
constructing a weighting matrix $D_\tau$ for each element of the Jacobian matrix, wherein
$d_{i,l}$ are the Elements of Matrix $D_\tau$, and
$d_{i,l} = \int_\Omega \phi_i(\vec{r}) \phi_l(\vec{r}) \phi_\tau(\vec{r}) d\vec{r}$; and
integrating over an area Ω where a basis function $\phi_\tau(\vec{r})$ for a $\tau^{th}$ node is non-zero.

14. A microwave imaging process, comprising:
generating microwave data,
illuminating a target with microwaves from a transmitting antenna,
receiving microwaves scattered by the target at a plurality of receiving antennas to form microwave data,
repeating the illuminating and receiving steps for a plurality of transmitting antennas, and
processing the microwave data to form permittivity and conductivity images by:
estimating initial permittivity ($\epsilon_r$) and conductivity (σ) distributions to form current $\epsilon_r$ and σ distributions,
determining a forward solution that is based on the current $\epsilon_r$ and σ distributions and utilizes a finite difference time domain method,
extracting computed electric field values, and
determining a tolerance metric based on the forward solution and the microwave data, and if the tolerance metric does not meet a preselected limit:
calculating a Jacobian matrix,
recalculating $\epsilon_r$ and σ distributions to form current $\epsilon_r$ and σ distributions, and
repeating the steps of determining the forward solution, extracting, determining the tolerance metric, calculating the Jacobian matrix, and recalculating until the tolerance metric meets the preselected limit.

15. The process of claim 14, wherein the $\epsilon_r$ and σ distributions form a two dimensional parameter mesh.

16. The process of claim 15, wherein the step of determining the forward solution comprises utilizing a forward solution obtained in one reconstruction iteration as a starting point for the finite difference time domain method in a subsequent iteration.

17. The process of claim 15, wherein the Jacobian matrix is computed utilizing a nodal adjoint method.

18. The process of claim 14, wherein the step of determining the forward solution includes
updating electric fields utilizing the equation $$E_z^{n+1}(p_{CC}) = cAEz(p_{CC})E_z^n(p_{CC}) + cBEz(p_{CC})$$
$$\left(\frac{H_y^{n+\frac{1}{2}}(p_R) - H_y^{n+\frac{1}{2}}(p_L)}{\Delta x} - \frac{H_x^{n+\frac{1}{2}}(p_T) - H_x^{n+\frac{1}{2}}(p_B)}{\Delta y}\right)$$

and updating magnetic fields utilizing the equations $$H_x^{n+\frac{1}{2}}(p_B) = cAHx(p_B)H_x^{n-\frac{1}{2}}(p_B) + cBHx(p_B)\left(\frac{E_z^n(p_{BB}) - E_z^n(p_{CC})}{\Delta y}\right)$$

and $$H_y^{n+\frac{1}{2}}(p_L) = cAHy(p_L)H_y^{n-\frac{1}{2}}(p_L) + cBHy(p_L)\left(\frac{E_z^n(p_{CC}) - E_z^n(p_{LL})}{\Delta x}\right)$$

where $E_z^n(p)$ is an electric field in a z-axis direction at location p at time n, $E_z^{n+1}(p)$ is an electric field in a z-axis direction at location p at time n plus a time step $\Delta t$, $$H_x^{n+\frac{1}{2}}(p)$$

is a magnetic field in an x-axis direction at location p at a time n plus one-half of $\Delta t$, $$H_x^{n-\frac{1}{2}}(p)$$

is a magnetic field in the x-axis direction at location p at a time n minus one-half of $\Delta t$, $$H_y^{n+\frac{1}{2}}(p)$$

is a magnetic field in a y-axis direction at location p at a time n plus one-half of $\Delta t$, $$H_y^{n-\frac{1}{2}}(p)$$

is a magnetic field in a y-axis direction at location p at a time n minus one-half of $\Delta t$, $$cAHx(p) = 1,$$
$$cBHx(p) = \frac{\Delta t}{\mu(p)},$$
$$cAHy(p) = 1,$$
$$cBHy(p) = \frac{\Delta t}{\mu(p)},$$

-continued $$cAEz(p) = \frac{2\varepsilon(p) - \sigma(p)\Delta t}{2\varepsilon(p) + \sigma(p)\Delta t},$$

$$cBEz(p) = \frac{2\Delta t}{2\varepsilon(p) + \sigma(p)\Delta t},$$

$$\mu(p_B)\frac{H_x^{n+\frac{1}{2}}(p_B) - H_x^{n-\frac{1}{2}}(p_B)}{\Delta t} = -\frac{E_z^n(p_{CC}) - E_z^n(p_{BB})}{\Delta y},$$

$$\mu(p_L)\frac{H_y^{n+\frac{1}{2}}(p_L) - H_y^{n-\frac{1}{2}}(p_L)}{\Delta t} = -\frac{E_z^n(p_{CC}) - E_z^n(p_{LL})}{\Delta x},$$

$$\varepsilon(p_{CC})\frac{E_z^{n+1}(p_{CC}) - E_z^n(p_{CC})}{\Delta t} + \sigma(p_{CC})\frac{E_z^{n+1}(p_{CC}) + E_z^n(p_{CC})}{2} =$$
$$\frac{H_y^{n+\frac{1}{2}}(p_R) - H_y^{n+\frac{1}{2}}(p_L)}{\Delta x} - \frac{H_x^{n+\frac{1}{2}}(p_T) - H_x^{n+\frac{1}{2}}(p_B)}{\Delta y},$$

$\epsilon(p)$ and $\sigma(p)$ are permittivity and conductivity, respectively, at point p, and $\Delta x$ and $\Delta y$ are grid lengths of a forward grid for which the forward solution is calculated.

19. The process of claim 14, wherein the $\epsilon_r$ and $\sigma$ distributions form a three dimensional parameter mesh.

20. The process of claim 19, wherein the step of determining the forward solution comprises utilizing a forward solution obtained in one reconstruction iteration as a starting point for the finite difference time domain technique in a subsequent iteration.

21. The process of claim 19, wherein the Jacobian matrix is computed utilizing a nodal adjoint method.

22. A microwave imaging process for reconstructing a permittivity and conductivity image utilizing microwave data of a target, comprising:
illuminating the target with microwaves from a transmitting antenna,
receiving microwaves scattered by the target at a plurality of receiving antennas to form the microwave data,
repeating the illuminating and receiving steps for a plurality of transmitting antennas, and
processing the microwave data to form permittivity and conductivity images by:
(a) estimating initial permittivity and conductivity distributions,
(b) determining forward solutions from the initial permittivity and conductivity distributions,
(c) determining a Jacobian matrix,
(d) determining dispersion coefficient updates using the microwave data and the Jacobian matrix,
(e) updating the permittivity and conductivity distributions to form current permittivity and conductivity distributions, and
(f) iteratively recalculating the forward solutions from the current permittivity and conductivity distributions, utilizing forward field solutions from one iteration as a starting point for a subsequent iteration.

23. A system for microwave imaging of a target, comprising:
a microwave frequency signal source that generates microwaves of multiple frequencies;
at least one transmitting antenna for transmitting microwaves from the signal source into an illumination tank, the target disposed in the illumination tank;
a plurality of receiving antennas in the illumination tank for receiving microwaves scattered from the target as microwave data;

a signal processor configured to process the microwave data into images of the target, including dispersion coefficient images from the microwave data; and wherein the signal processor
(a) determines a forward solution from permittivity and conductivity distributions,
(b) determines a Jacobian matrix, and
(c) determines dispersion coefficient updates using the microwave data, and repeats steps (a), (b) and (c) iteratively until the image converges, utilizing forward field solutions from one iteration as a starting point for a subsequent iteration.

24. A software product, comprising instructions stored on non-transitory computer-readable media, wherein the instructions, when executed by a processor, generate an image of a target using microwaves, comprising:

instructions for controlling illumination of the target with microwaves sequentially from a plurality of transmitting antennas and over a plurality of frequencies, instructions for storing microwave data from microwaves scattered by the target and received at a plurality of receiving antennas, instructions for selecting a frequency relationship for each of permittivity and conductivity, instructions for determining dispersion coefficients for the permittivity and conductivity frequency relationships, instructions for calculating permittivity and conductivity distributions for each frequency of the plurality of frequencies, instructions for determining forward solutions at multiple frequencies from initial estimates of permittivity and conductivity distributions, instructions for determining a dispersion coefficient based Jacobian matrix, instructions for determining dispersion coefficient updates using the microwave data, instructions for updating the dispersion coefficients, instructions for recalculating current permittivity and conductivity distributions for each frequency of the plurality of frequencies, and instructions for determining the forward solutions at multiple frequencies from the current permittivity and conductivity distributions.

25. Software product of claim 24, wherein the instructions for selecting the frequency relationship for each of permittivity and conductivity comprises instructions for selecting a permittivity relationship equation from the group consisting of $$\varepsilon_r = A\omega + B,$$

$$\ln(\varepsilon_r) = A\omega + B,$$

$$\varepsilon_r = A\ln(\omega) + B,$$

$$\ln(\varepsilon_r) = A\ln(\omega) + B \text{ and}$$

$$\varepsilon_r = \sum_{i=0}^{N} A_i \omega^i;$$

where $\varepsilon_r$ denotes relative permittivity, $\omega$ denotes angular frequency, i is a summation index, N is a polynomial order, and A and B are permittivity dispersion coefficients.

26. Software product of claim 25, further comprising instructions for utilizing the permittivity dispersion coefficients to form an image.

27. Software product of claim 24, wherein the instructions for selecting the frequency relationship for each of permittivity and conductivity comprises instructions for selecting a conductivity relationship equation from the group consisting of $$\sigma = A\omega + B,$$

$$\ln(\sigma) = A\omega + B,$$

$$\sigma = A\ln(\omega) + B,$$

$$\ln(\sigma) = A\ln(\omega) + B \text{ and}$$

$$\sigma = \sum_{i=0}^{N} A_i \omega^i;$$

where $\sigma$ denotes conductivity, $\omega$ denotes angular frequency, i is a summation index, N is a polynomial order, and A and B are conductivity dispersion coefficients.

28. Software product of claim 27, further comprising instructions for utilizing the conductivity dispersion coefficients to form an image.

29. Software product of claim 24, wherein the instructions for determining the forward solutions at multiple frequencies comprise instructions for utilizing electric field values from a previous step of recalculating the forward solutions as a starting point.

30. Software product of claim 24, wherein the instructions for determining the dispersion coefficient based Jacobian matrix comprises instructions for constructing a Jacobian matrix J, wherein elements $J((s,r), \tau)$ are defined by the relationship $$J((s, r), \tau) = \sum_{e \in \Omega_\tau} (D_\tau^e E_s^e)^T E_r^e; \text{ where}$$

$\Omega_\tau$ denotes a region within which a basis function $\phi_\tau \neq 0$, $\Sigma_{e \in \Omega_\tau}$ denotes a summation over forward elements which are located within $\Omega_\tau$, $E_s^e = \{E_s(\vec{p}_\kappa^e)\}_{\kappa=1}^{M}$ model electric field values at vertices ($\vec{p}_\kappa^e)_{\kappa=1}^{M}$ of an e-th forward element due to ones of the transmitting antennas at s and r, respectively, T indicates the transpose of a matrix, $D_\tau^e$ is a weighting matrix with each element defined by $$d_{i_e,l_e}^\tau = \int_{\Omega_e} \phi_{i_e}(\vec{r})\phi_{l_e}(\vec{r})\varphi_\tau(\vec{r})d\vec{r},$$

where $\phi_{i_e}(\vec{r})$, $\phi_{l_e}(\vec{r})$ and $\phi(\vec{r})$ represent basis functions over forward and parameter meshes, respectively, $i_e = 1, 2, \ldots M$ and $l_e = 1, 2, \ldots M$ are local node indices, M is a total node number for a single forward element, and $\Omega_e$ is a spatial domain occupied by the e-th forward element.

31. The software product of claim 24, wherein the instructions for determining the Jacobian matrix J comprise instructions for constructing Jacobian matrix elements $J((s,r), \tau)$ defined by the relationship $$J((s,r),\tau) = \sum_{n\in\Omega_\tau} \left(\frac{\sum_{e\in\Omega_n} V_e}{M}\right) \varphi_\kappa(\vec{p}_n) E_s(\vec{p}_n) E_r(\vec{p}_n),$$

where
- $\Omega_\tau$ denotes a region within which a basis function $\phi_\tau \neq 0$,
- $\Sigma_{n\in\Omega_\tau}$ refers to a summation over forward nodes which fall inside $\Omega_\tau$,
- $\Sigma_{e\in\Omega_n}$ refers to a summation over forward elements that share an n-th forward node within $\Omega_n$,
- $\phi_\kappa(\vec{p}_n)$ is the value of parameter mesh basis function at the set of forward nodes $\vec{p}_n$ within $\Omega_\tau$,
- $E_s(\vec{p}_n)$ and $E_r(\vec{p}_n)$ are nodal electrical field values computed directly from a forward problem, and
- $V_e$ is a volume of an e-th forward element within $\Omega_n$.

32. Software product of claim 31, wherein the instructions for constructing the Jacobian matrix comprise instructions for utilizing a log magnitude phase format algorithm.

33. Software product of claim 31, further comprising
instructions for constructing a weighting matrix $D_\tau$ for each element of the Jacobian matrix, wherein $d_{i,j}$ are the Elements of Matrix $D_\tau$, and $d_{i,j} = \int_\Omega \phi_i(\vec{r})\phi_j(\vec{r})\phi_\tau(\vec{r})d\vec{r}$; and
instructions for integrating over an area $\Omega$ where a basis function $\phi_\tau(\vec{r})$ for a $\tau^{th}$ node is non-zero.

34. A software product, comprising instructions stored on non-transitory computer-readable media, wherein the instructions, when executed by a processor operatively coupled with a microwave imaging apparatus, perform steps for reconstructing images of a target, comprising:
instructions for sequentially controlling illumination of the target with microwaves from each of a plurality of transmitting antennas of the imaging apparatus,
instructions for storing microwave data from microwaves scattered by the target and received at a plurality of receiving antennas of the imaging apparatus,
instructions for estimating initial permittivity ($\epsilon_r$) and conductivity ($\sigma$) distributions to form current $\epsilon_r$ and $\sigma$ distributions,
instructions for determining a forward solution that is based on the current $\epsilon_r$ and $\sigma$ distributions and utilizes a finite difference time domain method,
instructions for extracting computed electric field values,
instructions for determining a tolerance metric based on the forward solution and the microwave data,
instructions for calculating a Jacobian matrix,
instructions for recalculating $\epsilon_r$ and $\sigma$ distributions to form current $\epsilon_r$ and $\sigma$ distributions, and
instructions for repeating the steps of determining the forward solution, extracting, determining the tolerance metric, calculating the Jacobian matrix, and recalculating until the tolerance metric meets a preselected limit.

35. Software product of claim 34, wherein
the instructions for estimating initial $\epsilon_r$ and $\sigma$ distributions comprise instructions for estimating the initial $\epsilon_r$ and $\sigma$ distributions that form a two dimensional parameter mesh, and
the instructions for recalculating $\epsilon_r$ and $\sigma$ distributions to form current $\epsilon_r$ and $\sigma$ distributions comprise instructions for recalculating $\epsilon_r$ and $\sigma$ distributions to form current $\epsilon_r$ and $\sigma$ distributions over the two dimensional parameter mesh.

36. Software product of claim 35, wherein the instructions for determining the forward solution comprise instructions for utilizing a forward solution obtained in one reconstruction iteration as a starting point for the finite difference time domain method in a subsequent iteration.

37. Software product of claim 35, wherein the instructions for calculating the Jacobian matrix comprise instructions for utilizing a nodal adjoint method.

38. Software product of claim 34, wherein
the instructions for estimating initial $\epsilon_r$ and $\sigma$ distributions comprise instructions for estimating the initial $\epsilon_r$ and $\sigma$ distributions that form a three dimensional parameter mesh, and
the instructions for recalculating $\epsilon_r$ and $\sigma$ distributions to form current $\epsilon_r$ and $\sigma$ distributions comprise instructions for recalculating $\epsilon_r$ and $\sigma$ distributions to form current $\epsilon_r$ and $\sigma$ distributions over the three dimensional parameter mesh.

39. Software product of claim 38, wherein the instructions for determining the forward solution comprise instructions for utilizing a forward solution obtained in one reconstruction iteration as a starting point for the finite difference time domain technique in a subsequent iteration.

40. Software product of claim 38, wherein the instructions for calculating the Jacobian matrix comprise instructions for utilizing a nodal adjoint method.

* * * * *

UNITED STATES PATENT AND TRADEMARK OFFICE
CERTIFICATE OF CORRECTION

PATENT NO. : 7,825,667 B2
APPLICATION NO. : 11/316641
DATED : November 2, 2010
INVENTOR(S) : Fang et al.

It is certified that error appears in the above-identified patent and that said Letters Patent is hereby corrected as shown below:

Column 11, line 41, "planes $P_{10}rP_2$" should read --planes $P_1$ or $P_2$--;

Column 14, line 50, "($\omega$))" should read --($\omega$)--; line 51, "($\omega$w)" should read --($\omega$)--;

Column 16, line 8, "Eq. 10 and" should read --of Eq. 10 and--;

Column 18, line 19, "and ɸ" should read --and $\varphi$--;

Line 23, "$E_s^e = \{E_s(P_\kappa^e)\}_{\kappa=1}^M$ and $E_r^e = \{E_r(P_\kappa^e)\}_{\kappa=1}^M$,"

should read -- $\mathbf{E}_r^e = \{E_r(\vec{p}_\kappa^e)\}_{\kappa=1}^M$ -- and -- $\mathbf{E}_s^e = \{E_s(\vec{p}_\kappa^e)\}_{\kappa=1}^M$ --;

Signed and Sealed this
Third Day of May, 2011

David J. Kappos
*Director of the United States Patent and Trademark Office*